(12) United States Patent
Stasi et al.

(10) Patent No.: US 8,859,608 B2
(45) Date of Patent: Oct. 14, 2014

(54) SPIRO AMINO COMPOUNDS SUITABLE FOR THE TREATMENT OF INTER ALIA SLEEP DISORDERS AND DRUG ADDICTION

(75) Inventors: Luigi Piero Stasi, Monza (IT); Lucio Rovati, Monza (IT)

(73) Assignee: Rottapharm Biotech S.R.L., Monza (IT)

( * ) Notice: Subject to any disclaimer, the term of this patent is extended or adjusted under 35 U.S.C. 154(b) by 317 days.

(21) Appl. No.: 13/384,166

(22) PCT Filed: Jul. 15, 2010

(86) PCT No.: PCT/EP2010/060206
§ 371 (c)(1),
(2), (4) Date: Jan. 13, 2012

(87) PCT Pub. No.: WO2011/006960
PCT Pub. Date: Jan. 20, 2011

(65) Prior Publication Data
US 2012/0115882 A1    May 10, 2012

(30) Foreign Application Priority Data
Jul. 15, 2009 (EP) .................................... 09425285

(51) Int. Cl.
| | | |
|---|---|---|
| *A61K 31/40* | (2006.01) | |
| *A61K 31/44* | (2006.01) | |
| *C07D 221/00* | (2006.01) | |
| *C07D 209/54* | (2006.01) | |
| *C07D 417/14* | (2006.01) | |
| *C07D 417/06* | (2006.01) | |
| *C07D 401/14* | (2006.01) | |
| *C07D 401/12* | (2006.01) | |

(52) U.S. Cl.
CPC ............ *C07D 417/14* (2013.01); *C07D 417/06* (2013.01); *C07D 401/14* (2013.01); *C07D 401/12* (2013.01)
USPC .............. 514/409; 514/278; 546/16; 548/408

(58) Field of Classification Search
USPC ....................... 546/16; 514/278, 409; 548/408
See application file for complete search history.

(56) References Cited

FOREIGN PATENT DOCUMENTS

| WO | WO 2008/038251 A2 | 4/2008 |
|---|---|---|
| WO | WO 2008/139416 A1 | 11/2008 |

OTHER PUBLICATIONS

International Search Report and Written Opinion dated Dec. 21, 2010 for corresponding International Patent Application No. PCT/EP2010/060206.

*Primary Examiner* — Rita Desai
(74) *Attorney, Agent, or Firm* — Ohlandt Greeley Ruggiero & Perle L.L.P.

(57) ABSTRACT

A spiro-amino compound of Formula (VI) wherein m is 1 or 2 or 3, n is 1 or 2, R is selected from a 5- or 6-membered aromatic ring and a 5- or 6-membered heteroaromatic ring comprising 1 to 3 heteroatoms selected from S, O and N, such ring being substituted with one or two substituents selected from the group consisting of $(C_1-C_3)$alkyl, halogen, $(C_3-C_5)$ cycloalkyloxy, $(C_1-C_3)$alkylcarbonyl, phenyl optionally substituted with one or more halogen atoms, a 5- or 6-membered heterocycle comprising at least one nitrogen atom; P is a substituent Q or COQ, wherein Q is selected from the group consisting of phenyl, pyridyl, pyrimidyl, quinolyl, isoquinolyl, quinoxalyl, benzofuranyl, imidazotriazolyl, being such Q optionally substituted with one or more substituents selected from the group consisting of $(C_1-C_3)$alkyl, halogen, trifluoromethyl, carbammido, methylcarbammido, carboxy, methylcarboxy or a pharmaceutically acceptable salt thereof.

17 Claims, No Drawings

SPIRO AMINO COMPOUNDS SUITABLE FOR THE TREATMENT OF INTER ALIA SLEEP DISORDERS AND DRUG ADDICTION

BACKGROUND

1. Field of the Disclosure

The disclosure relates to novel spiro aminic compounds with Orexin 1 antagonist activity.

The disclosure also concerns a process for the preparation of those compounds, pharmaceutical compositions containing one or more compounds of Formula (VI) and their use as antagonists of the orexin 1 receptor.

2. Discussion of the Background Art

The orexins are neuropeptides discovered in 1998 from two research groups. Orexin A is a 33 aminic acid peptide while orexin B is a 28 aminic acid peptide. The orexins are secreted from a discrete group of neurons in the lateral hypothalamus and they bind to G-coupled receptors, namely OX1 and OX2. The orexin 1 receptor (OX1) binds selectively the orexin A, while the orexin 2 receptor (OX2) binds both orexin A and orexin B.

Orexins are known to stimulate food consumption in rats, thus suggesting their role as modulators in food intake mechanisms.

Moreover it has been shown that orexins regulate the sleep architecture, thus making them a novel therapeutic approach to narcolepsy, as a treatment for insomnia and other sleep disorders. It has been recently shown that orexins are involved in addiction mechanisms, thus their modulations will make possible the treatment of compulsive disorders and drug addictions. Orexin receptors are located in mammals brain and they are involved in several pathologies.

In the international patent application WO2009/016560 trans-3-aza-bicyclo[3.1.0]exane derivatives have been disclosed as a series of orexin antagonists.

Novel pyrrolidine and piperidine derivatives have been disclosed in WO2009/040730, N-aroil cyclic amine derivatives were disclosed in the international patent application WO02/090355 and piperazine compounds in WO03/051873, being all those novel structures proposed as antagonists of the orexin receptors.

A series of cyclic N-aroylamine derivatives has been disclosed in the international patent application WO2004/026866 as non-peptidic antagonists of the human orexin receptors. In particular 43 piperidine compounds, where the position beta to the nitrogen was substituted with hydrogen or methyl groups, have been tested for their activities against OX1 and OX2 receptors.

Those documents describe compounds with activity at both receptors.

The object of the present disclosure is to provide compounds with selective antagonist activity at the orexin 1 receptor.

SUMMARY OF THE DISCLOSURE

The object of the disclosure has been achieved by a spiro-amino compound of Formula (VI):

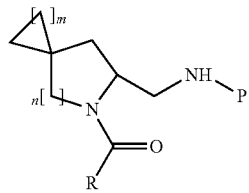

(VI)

where
  m is 1 or 2 or 3
  n is 1 or 2,
  R is selected from a 5- or 6-membered aromatic ring and a 5- or 6-membered heteroaromatic ring containing 1 to 3 heteroatoms selected from S, O and N, such ring being substituted with one or two substituents selected from the group consisting of ($C_1$-$C_3$)alkyl, halogen, ($C_3$-$C_5$)cycloalkyloxy, ($C_1$-$C_3$)alkylcarbonyl, phenyl optionally substituted with one or more halogen atoms, a 5- or 6-membered heterocycle containing at least one nitrogen atom;
  P is a substituent Q or COQ, where Q is a group chosen from phenyl, pyridyl, pyrimidyl, quinolyl, isoquinolyl, quinoxalyl, benzofuranyl, imidazotriazolyl, being such Q optionally substituted with one or more substituents selected from the group consisting of ($C_1$-$C_3$)alkyl, halogen, trifluoromethyl, carbammido, methylcarbammido, carboxy; methylcarboxy
  or a pharmaceutically acceptable salt thereof.

In this disclosure compounds of Formula (VI) may exist as R and S enantiomers and as racemic mixture. This disclosure includes in its scope of protection all the possible isomers and racemic mixtures. Wherever should be present further symmetry centers, this disclosure includes all the possible diastereoisomers and relative mixtures as well.

In a first embodiment, in the spiro-amino compound of Formula (VI), P is Q. This is a compound of Formula (VIa):

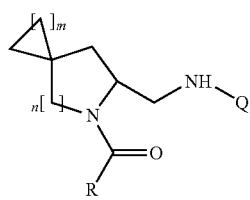

VIa

In a second embodiment, in the spiro-amino compound of Formula (VI), P is COQ. This is a compound of Formula (VIb):

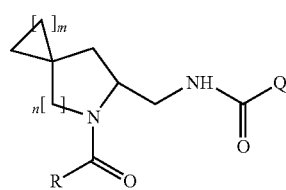

VIb

A further aspect of this disclosure concerns a process for the preparation of a compound of Formula (VIa) comprising the following steps represented in the scheme below:

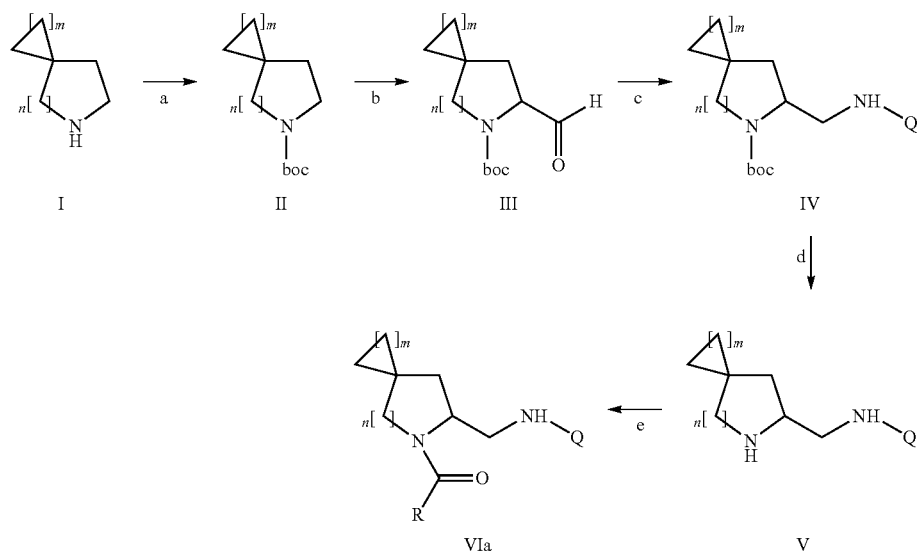

a) protecting a compound of Formula (I) with a BOC protecting group to obtain a compound of Formula (II);

b) reacting a compound of Formula (II) with strong bases and dimethylformamide, thus obtaining a compound of Formula (III);

c) adding an amine of Formula Q-NH$_2$, where Q is selected from the group consisting of phenyl, pyridyl, pyrimidyl, quinolyl, isoquinolyl, quinoxalyl, benzofuranyl, imidazotriazolyl, being such Q optionally substituted with one or more substituents selected from the group consisting of (C$_1$-C$_3$) alkyl, halogen, trifluoromethyl, carbammido, methylcarbammido, carboxy, methylcarboxy in the presence of a reducing agent to obtain a compound of Formula (IV);

d) cleaving the BOC group from the compound of Formula (IV) to obtain a compound of Formula (V);

e) reacting a compound of Formula (V) with RCOOH in the presence of coupling reagents or with the corresponding acyl chlorides RCOCl in the presence of a base, where R is selected from a 5- or 6-membered aromatic ring and a 5- or 6-membered heteroaromatic ring containing 1 to 3 heteroatoms selected from S, O and N, such ring being substituted with one or two substituents selected from the group consisting of (C$_1$-C$_3$)alkyl, halogen, (C$_3$-C$_5$)cycloalkoxy, (C$_1$-C$_3$) alkylcarbonyl, phenyl optionally substituted with one or more halogen atoms, a 5- or 6-membered heterocycle containing at least one nitrogen atom.

In a further aspect, the disclosure concerns a process for the preparation of a compound of Formula (VIb) which comprises the following steps represented in the scheme below:

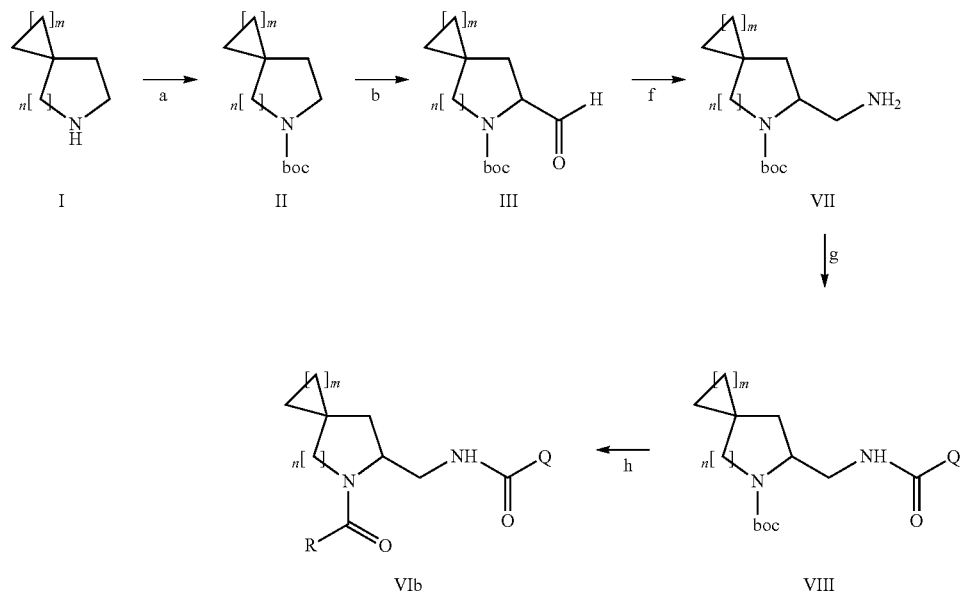

a) protecting a compound of Formula (I) with a BOC protecting group to obtain a compound of Formula (II);

b) reacting a compound of Formula (II) with strong bases and dimethylformamide, thus obtaining a compound of Formula (III);

f) making a reductive amination of the compound of Formula (III) to obtain an amine of Formula (VII);

g) reacting a compound of Formula (VII) with QCOOH in the presence of coupling reagents or with the corresponding acyl chlorides QCOCl in the presence of a base to obtain the amide of Formula (VIII), wherein Q is a group chosen from phenyl, pyridyl, pyrimidyl, quinolyl, isoquinolyl, quinoxalyl, benzofuranyl, imidazotriazolyl, being such Q optionally substituted with one or more substituents selected from the group consisting of $(C_1-C_3)$alkyl, halogen, trifluoromethyl, carbammido, methylcarbammido, carboxy, methylcarboxy;

h) cleaving the BOC group from the compound of Formula (VIII) and reacting with RCOOH in the presence of coupling reagents or with the corresponding acyl chlorides RCOCl in the presence of a base to give a compound of Formula VIb, wherein R is selected from a 5- or 6-membered aromatic ring and a 5- or 6-membered heteroaromatic ring containing 1 to 3 heteroatoms selected from S, O and N, such ring being substituted with one or two substituents selected from the group consisting of $(C_1-C_3)$alkyl, halogen, $(C_3-C_5)$cycloalkyloxy, $(C_1-C_3)$alkylcarbonyl, phenyl optionally substituted with one or more halogen atoms, a 5- or 6-membered heterocycle comprising at least one nitrogen atom.

In another aspect the disclosure concerns pharmaceutical compositions comprising a compound of Formula (VI), preferably (VIa), and a pharmaceutically acceptable carrier.

In another aspect the disclosure concerns a compound of Formula (VI) as medicament, in particular it concerns its use for the manufacturing of a medicament for the treatment of pathologies where an antagonist of the OX1 antagonist is needed, such as the treatment of obesity, sleep disorders, compulsive disorders, drug dependency, schizophrenia.

DETAILED DESCRIPTION OF THE DISCLOSURE

The disclosure thus concerns a spiro-amino compound of Formula (VI):

(VI)

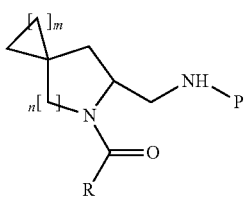

wherein
m is 1 or 2 or 3
n is 1 or 2,
R is selected from a 5- or 6-membered aromatic ring and a 5- or 6-membered heteroaromatic ring comprising 1 to 3 heteroatoms selected from S, O and N, such ring being substituted with one or two substituents selected from the group consisting of $(C_1-C_3)$alkyl, halogen, $(C_3-C_5)$cycloalkyloxy, $(C_1-C_3)$alkylcarbonyl, phenyl optionally substituted with one or more halogen atoms, a 5- or 6-membered heterocycle comprising at least one nitrogen atom;

P is a substituent Q or COQ, wherein Q is a group selected from phenyl, pyridyl, pyrimidyl, quinolyl, isoquinolyl, quinoxalyl, benzofuranyl, imidazotriazolyl, being such Q optionally substituted with one or more substituents selected from $(C_1-C_3)$alkyl, halogen, trifluoromethyl, carbammido, methylcarbammido, carboxy, methylcarboxy;

or a pharmaceutically acceptable salt thereof.

In a first embodiment, in spiro-amino compound of Formula (VI), P is Q. This is a compound of Formula (VIa):

VIa

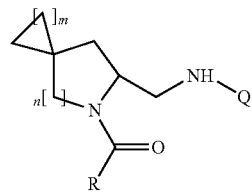

In this embodiment, preferably n is 2 and m is 1.

A preferred embodiment of the first embodiment of the disclosure concerns a piperidine ring compound with a spiro 3 carbon-atoms ring gamma to the nitrogen atom. R is preferably a phenyl or an heterocyclic ring.

More preferably when R is an heterocyclic ring, this is a thiazole ring, even more preferably a thiazole ring substituted with at least one substituent selected from the group consisting of methyl, phenyl, phenyl substituted with one or more halogens.

More preferably, when R is phenyl, it is a phenyl substituted with a group chosen from cyclopropil$(C_1-C_3)$alkyloxy, triazolil, pyrimidyl.

Preferably Q is a pyridyl ring, even more preferably a pyridyl substituted with one or more substituents selected from the group consisting of trifluoromethyl, carboxy, methylcarboxy methyl and halogen.

The preferred compounds of the disclosure are selected from the group consisting of:
methyl 5-chloro-2-(((6-(5-(4-fluorophenyl)-2-methylthiazole-4-carbonyl)-6-azaspiro[2.5]octan-5-yl)methyl)amino)benzoate
(2-methyl-5-phenylthiazol-4-yl)(5-(((5-(trifluoromethyl)pyridin-2-yl)amino)methyl)-6-azaspiro[2.5]octan-6-yl)methanone
(2-methyl-5-phenylthiazol-4-yl)(5-(((6-methylpyridin-2-yl)amino)methyl)-6-azaspiro[2.5]octan-6-yl)methanone
(2-methyl-5-phenylthiazol-4-yl)(7-(((6-methylpyridin-2-yl)amino)methyl)-8-azaspiro[4.5]decan-8-yl)methanone
(5-(((5-chloropyridin-2-yl)amino)methyl)-6-azaspiro[2.5]octan-6-yl)(2-(cyclopropylmethoxy)phenyl)methanone
(5-(((5-chloropyridin-2-yl)amino)methyl)-6-azaspiro[2.5]octan-6-yl)(2-(pyrimidin-2-yl)phenyl)methanone
(5-(((5-chloropyridin-2-yl)amino)methyl)-6-azaspiro[2.5]octan-6-yl)(2-methyl-5-phenylthiazol-4-yl)methanone
(5-(((5-chloropyridin-2-yl)amino)methyl)-6-azaspiro[2.5]octan-6-yl)(5-(4-fluorophenyl)-2-methylthiazol-4-yl)methanone
(5-(((5-chloropyridin-2-yl)amino)methyl)-6-azaspiro[2.5]octan-6-yl)(5-methyl-2-(2H-1,2,3-triazol-2-yl)phenyl)methanone
(5-(((5-chloropyridin-2-yl)amino)methyl)-6-azaspiro[2.5]octan-6-yl)(5-methyl-2-(pyrimidin-2-yl)phenyl)methanone
(5-(((5-fluoropyridin-2-yl)amino)methyl)-6-azaspiro[2.5]octan-6-yl)(2-methyl-5-phenylthiazol-4-yl)methanone (7-(((5-chloropyridin-2-yl)amino)methyl)-8-azaspiro[4.5]decan-8-yl)(2-methyl-5-phenylthiazol-4-yl)methanone (R)-(2-methyl-5-phenylthiazol-4-yl)(5-(((6-methylpyridin-2-yl)amino)methyl)-6-azaspiro[2.5]octan-6-yl)methanone (R)-(5-(((5-chloropyridin-2-yl)amino)methyl)-6-azaspiro[2.5]octan-6-yl)(2-methyl-5-phenylthiazol-4-yl)methanone (R)-(5-(((5-chloropyridin-2-yl)amino)methyl)-6-azaspiro[2.5]octan-6-yl)(5-fluoro-2-(pyrimidin-2-yl)phenyl)methanone (R)-(5-methyl-2-(pyrazin-2-yl)phenyl)(5-(((6-(trifluoromethyl)pyridin-2-yl)amino)methyl)-6-azaspiro[2.5]octan-6-yl)methanone (S)-(2,5-dichlorophenyl)(5-(((4,6-dimethylpyrimidin-2-yl)amino)methyl)-6-azaspiro[2.5]octan-6-yl)methanone (S)-(2-(2H-1,2,3-triazol-2-yl)phenyl)(5-(((5-chloropyridin-2-yl)amino)methyl)-6-azaspiro[2.5]octan-6-yl)methanone (S)-(2-methyl-5-phenylthiazol-4-yl)(5-(((4-methylpyrimidin-2-yl)amino)methyl)-6-azaspiro[2.5]octan-6-yl)methanone (S)-(2-methyl-5-phenylthiazol-4-yl)(5-(((5-(trifluoromethyl)pyridin-2-yl)amino)methyl)-6-azaspiro[2.5]octan-6-yl)methanone (S)-(2-methyl-5-phenylthiazol-4-yl)(5-(((5-methylpyrimidin-2-yl)amino)methyl)-6-azaspiro[2.5]octan-6-yl)methanone (S)-(2-methyl-5-phenylthiazol-4-yl)(5-(((6-(trifluoromethyl)pyridin-2-yl)amino)methyl)-6-azaspiro[2.5]octan-6-yl)methanone (S)-(2-methyl-5-phenylthiazol-4-yl)(5-(((6-methylpyridin-2-yl)amino)methyl)-6-azaspiro[2.5]octan-6-yl)methanone (S)-(5-(((4,6-difluoropyrimidin-2-yl)amino)methyl)-6-azaspiro[2.5]octan-6-yl)(2-methyl-5-phenylthiazol-4-yl)methanone (S)-(5-(((4,6-dimethylpyrimidin-2-yl)amino)methyl)-6-azaspiro[2.5]octan-6-yl)(2-methyl-5-phenylthiazol-4-yl)methanone (S)-(5-(((5-chloropyridin-2-yl)amino)methyl)-6-azaspiro[2.5]octan-6-yl)(2-(pyrazin-2-yl)phenyl)methanone (S)-(5-(((5-chloropyridin-2-yl)amino)methyl)-6-azaspiro[2.5]octan-6-yl)(2-(pyrimidin-2-yl)phenyl)methanone (S)-(5-(((5-chloropyridin-2-yl)amino)methyl)-6-azaspiro[2.5]octan-6-yl)(2-fluoro-6-(2H-1,2,3-triazol-2-yl)phenyl)methanone (S)-(5-(((5-chloropyridin-2-yl)amino)methyl)-6-azaspiro[2.5]octan-6-yl)(2-fluoro-6-(pyridin-2-yl)phenyl)methanone (S)-(5-(((5-chloropyridin-2-yl)amino)methyl)-6-azaspiro[2.5]octan-6-yl)(2-fluoro-6-(pyrimidin-2-yl)phenyl)methanone (S)-(5-(((5-chloropyridin-2-yl)amino)methyl)-6-azaspiro[2.5]octan-6-yl)(2-methyl-5-phenylthiazol-4-yl)methanone (S)-(5-(((5-chloropyridin-2-yl)amino)methyl)-6-azaspiro[2.5]octan-6-yl)(5-fluoro-2-(2H-1,2,3-triazol-2-yl)phenyl)methanone (S)-(5-(((5-chloropyridin-2-yl)amino)methyl)-6-azaspiro[2.5]octan-6-yl)(5-fluoro-2-(pyrazin-2-yl)phenyl)methanone (S)-(5-(((5-chloropyridin-2-yl)amino)methyl)-6-azaspiro[2.5]octan-6-yl)(5-fluoro-2-(pyridin-2-yl)phenyl)methanone (S)-(5-(((5-chloropyridin-2-yl)amino)methyl)-6-azaspiro[2.5]octan-6-yl)(5-fluoro-2-(pyrimidin-2-yl)phenyl)methanone (S)-(5-(((5-chloropyridin-2-yl)amino)methyl)-6-azaspiro[2.5]octan-6-yl)(5-methyl-2-(pyridin-2-yl)phenyl)methanone (S)-(5-(((5-chloropyridin-2-yl)amino)methyl)-6-azaspiro[2.5]octan-6-yl)(5-methyl-2-(pyrimidin-2-yl)phenyl)methanone (S)-(5-(((5-fluoropyridin-2-yl)amino)methyl)-6-azaspiro[2.5]octan-6-yl)(2-methyl-5-phenylthiazol-4-yl)methanone (S)-(5-(((6-chloropyridin-2-yl)amino)methyl)-6-azaspiro[2.5]octan-6-yl)(2-methyl-5-phenylthiazol-4-yl)methanone (S)-(5-(((6-chloropyridin-2-yl)amino)methyl)-6-azaspiro[2.5]octan-6-yl)(5-methyl-2-(2H-1,2,3-triazol-2-yl)phenyl)methanone (S)-(5-(((6-chloropyridin-2-yl)amino)methyl)-6-azaspiro[2.5]octan-6-yl)(5-methyl-2-(pyrazin-2-yl)phenyl)methanone (S)-(5-(((6-chloropyridin-2-yl)amino)methyl)-6-azaspiro[2.5]octan-6-yl)(5-methyl-2-(pyrimidin-2-yl)phenyl)methanone (S)-(5-(((6-fluoropyridin-2-yl)amino)methyl)-6-azaspiro[2.5]octan-6-yl)(2-methyl-5-phenylthiazol-4-yl)methanone (S)-(5-methyl-2-(2H-1,2,3-triazol-2-yl)phenyl)(5-(((5-(trifluoromethyl)pyridin-2-yl)amino)methyl)-6-azaspiro[2.5]octan-6-yl)methanone (S)-(5-methyl-2-(2H-1,2,3-triazol-2-yl)phenyl)(5-(((6-(trifluoromethyl)pyridin-2-yl)amino)methyl)-6-azaspiro[2.5]octan-6-yl)methanone (S)-(5-methyl-2-(pyrazin-2-yl)phenyl)(5-(((6-(trifluoromethyl)pyridin-2-yl)amino)methyl)-6-azaspiro[2.5]octan-6-yl)methanone (S)-(5-methyl-2-(pyrimidin-2-yl)phenyl)(5-(((5-(trifluoromethyl)pyridin-2-yl)amino)methyl)-6-azaspiro[2.5]octan-6-yl)methanone (S)-(5-methyl-2-(pyrimidin-2-yl)phenyl)(5-(((6-(trifluoromethyl)pyridin-2-yl)amino)methyl)-6-azaspiro[2.5]octan-6-yl)methanone (S)-[1,1-biphenyl]-2-yl(5-(((4,6-dimethylpyrimidin-2-yl)amino)methyl)-6-azaspiro[2.5]octan-6-yl)methanone (7-(((5-chloropyridin-2-yl)amino)methyl)-8-azaspiro[4.5]decan-8-yl)(2-methyl-5-phenylthiazol-4-yl)methanone (2-methyl-5-phenylthiazol-4-yl)(7-(((6-methylpyridin-2-yl)amino)methyl)-8-azaspiro[4.5]decan-8-yl)methanone (S)-(6-(((5-chloropyridin-2-yl)amino)methyl)-5-azaspiro[2.4]heptan-5-yl)(5-methyl-2-(2H-1,2,3-triazol-2-yl)phenyl)methanone (S)-(5-methyl-2-(2H-1,2,3-triazol-2-yl)phenyl)(6-(((6-methylpyridin-2-yl)amino)methyl)-5-azaspiro[2.4]heptan-5-yl)methanone (S)-(6-(((5-chloropyridin-2-yl)amino)methyl)-5-azaspiro[2.4]heptan-5-yl)(5-methyl-2-(pyrimidin-2-yl)phenyl)methanone In a first embodiment of the disclosure when m=2, n is preferably equal to 2.

In this embodiment:

Q is preferably selected from pyridyl, pyridyl substituted with one or more substituents selected from $(C_1-C_3)$alkyl, trifluoromethyl, halogen; and R is selected from phenyl and a 5-membered heteroaromatic ring comprising two heteroatoms selected from S, O and N, such ring being substituted with one substituent selected from $(C_1-C_3)$alkyl, pyrimidyl, thiazolil, phenyl optionally substituted with one or more halogen atoms.

Preferred compounds when m=2 are:

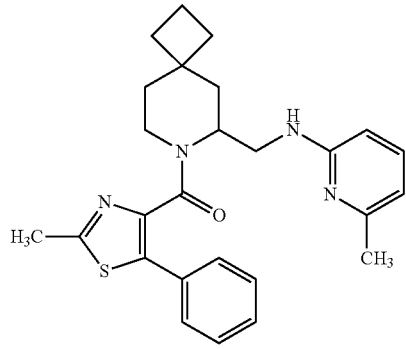 [SMILES: Cc1cccc(NCC2CC3(CCC3)CCN2C(=O)c2nc(C)sc2-c2ccccc2)n1]

(2-methyl-5-phenylthiazol-4-yl)(6-(((6-methylpyridin-2-ylamino)methyl)-7-azaspiro[3.5]nonan-7-yl)methanone

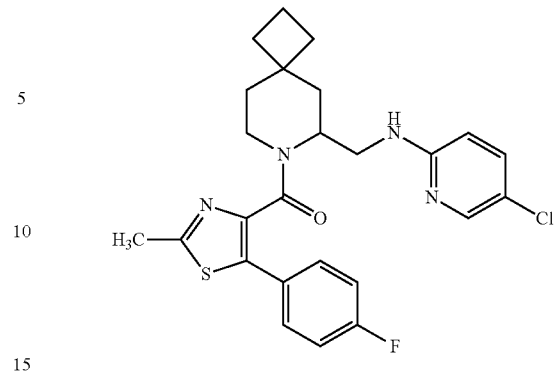

(6-((5-chloropyridin-2-ylamino)methyl)-7-azaspiro[3.5]nonan-7-yl)(5-(4-fluorophenyl)-2-methylthiazol-4-yl)methanone

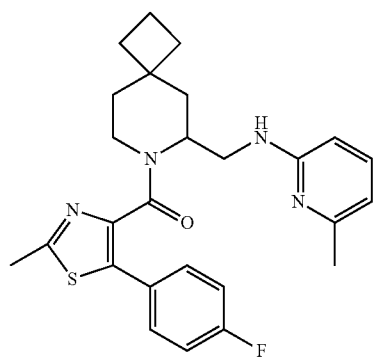 [SMILES: Cc1cccc(NCC2CC3(CCC3)CCN2C(=O)c2nc(C)sc2-c2ccc(F)cc2)n1]

(5-(4-fluorophenyl)-2-methylthiazol-4-yl)(6-(((6-methylpyridin-2-ylamino)methyl)-7-azaspiro[3.5]nonan-7-yl)methanone

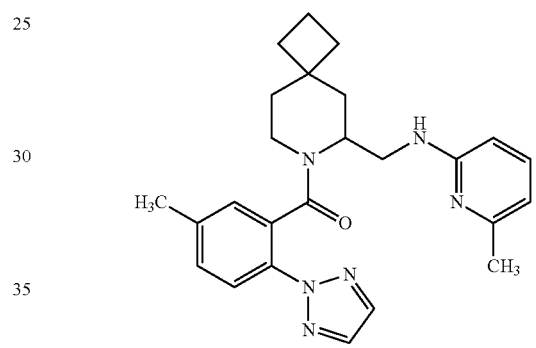

(5-methyl-2-(2H-1,2,3-triazol-2-yl)phenyl)(6-(((6-methylpyridin-2-ylamino)methyl)-7-azaspiro[3.5]nonan-7-yl)methanone

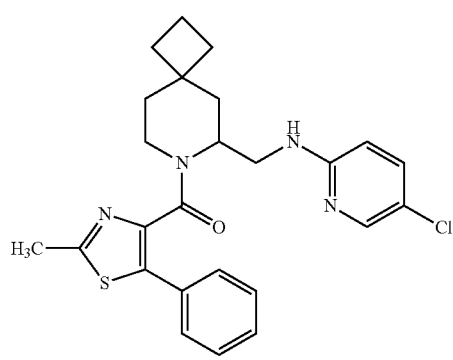 [SMILES: Cc1nc(C(=O)N2CCC3(CCC3)CC2CNc2ccc(Cl)cn2)c(-c2ccccc2)s1]

(6-((5-chloropyridin-2-ylamino)methyl)-7-azaspiro[3.5]nonan-7-yl)(2-methyl-5-phenylthiazol-4-yl)methanone

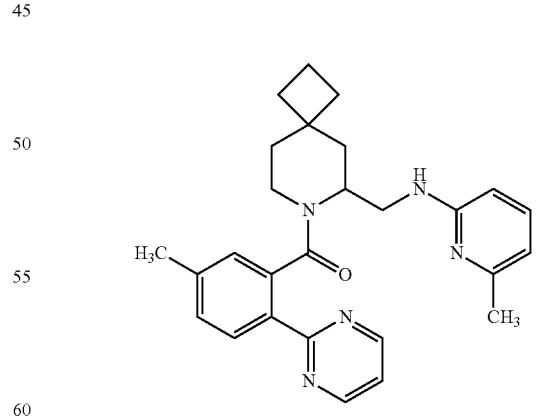

(5-methyl-2-(pyrimidin-2-yl)phenyl)(6-(((6-methylpyridin-2-ylamino)methyl)-7-azaspiro[3.5]nonan-7-yl)methanone

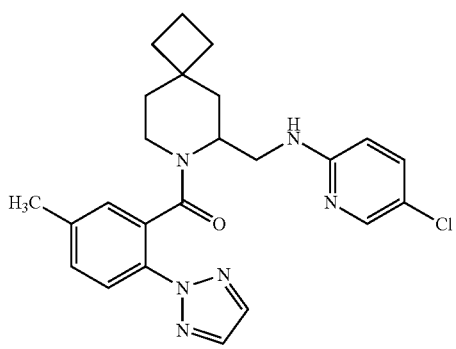 [SMILES: Cc1ccc(-n2nccn2)c(C(=O)N2CCC3(CCC3)CC2CNc2ccc(Cl)cn2)c1]

(6-((5-chloropyridin-2-ylamino)methyl)-7-azaspiro[3.5]
nonan-7-yl)(5-methyl-2-(2H-1,2,3-triazol-2-yl)phenyl)
methanone

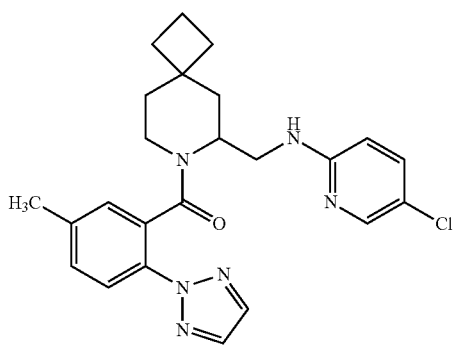 [SMILES: Cc1ccc(-n2nccn2)c(C(=O)N2CCC3(CCC3)CC2CNc2ccc(Cl)cn2)c1]

(6-((5-chloropyridin-2-ylamino)methyl)-7-azaspiro[3.5]
nonan-7-yl)(5-methyl-2-(pyrimidin-2-yl)phenyl)metha-
none

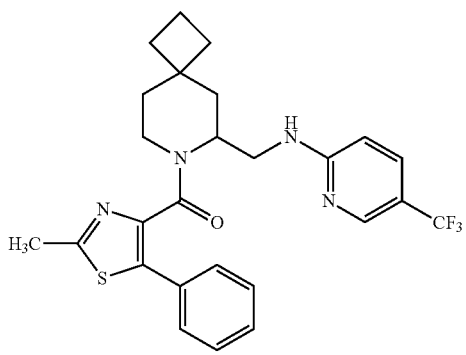 [SMILES: Cc1nc(C(=O)N2CCC3(CCC3)CC2CNc2ccc(C(F)(F)F)cn2)c(-c2ccccc2)s1]

(2-methyl-5-phenylthiazol-4-yl)(6-((5-(trifluoromethyl)py-
ridin-2-ylamino)methyl)-7-azaspiro[3.5]nonan-7-yl)
methanone

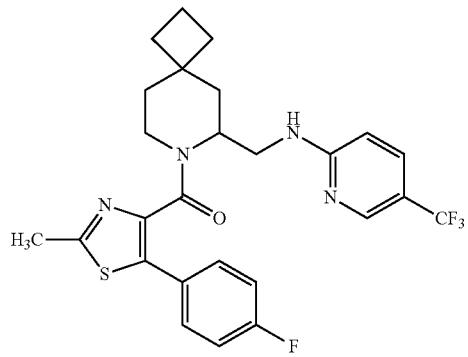 [SMILES: Cc1nc(C(=O)N2CCC3(CCC3)CC2CNc2ccc(C(F)(F)F)cn2)c(-c2ccc(F)cc2)s1]

(5-(4-fluorophenyl)-2-methylthiazol-4-yl)(6-((5-(trifluo-
romethyl)pyridin-2-ylamino)methyl)-7-azaspiro[3.5]
nonan-7-yl)methanone

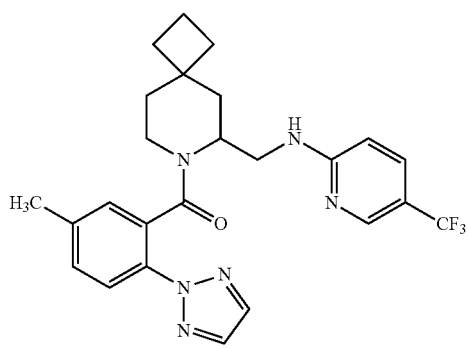 [SMILES: Cc1ccc(-n2nccn2)c(C(=O)N2CCC3(CCC3)CC2CNc2ccc(C(F)(F)F)cn2)c1]

(5-methyl-2-(2H-1,2,3-triazol-2-yl)phenyl)(6-((5-(trifluo-
romethyl)pyridin-2-ylamino)methyl)-7-azaspiro[3.5]
nonan-7-yl)methanone

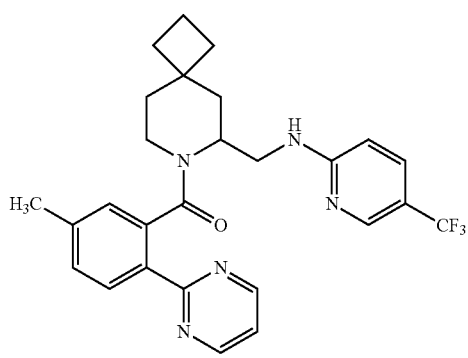 [SMILES: Cc1ccc(-c2ncccn2)c(C(=O)N2CCC3(CCC3)CC2CNc2ccc(C(F)(F)F)cn2)c1]

(5-methyl-2-(pyrimidin-2-yl)phenyl)(6-((5-(trifluorom-
ethyl)pyridin-2-ylamino)methyl)-7-azaspiro[3.5]nonan-
7-yl)methanone When m=3, n is preferably equal to 2.

In this embodiment:

Q is preferably selected from pyridyl, pyridyl substituted
with trifluoromethyl; pyridyl substituted with $(C_1-C_3)$
alkyl R is preferably selected from phenyl and a 5-membered
heteroaromatic ring comprising two heteroatoms
selected from S, O and N, such R being substituted with
one or two substituents selected from $(C_1-C_3)$alkyl, halogen, pyrimidyl, thiazolil, phenyl optionally substituted with one or more halogen atoms.

More preferably, Q is pyridyl substituted with trifluoromethyl or pyridyl substituted with $(C_1-C_3)$alkyl and R is 5-membered heteroaromatic ring comprising two heteroatoms selected from S, O and N, still more preferably thiazolil, such R being substituted with one or two substituents selected from $(C_1-C_3)$alkyl and halogen.

Preferred compounds when m=3 are:

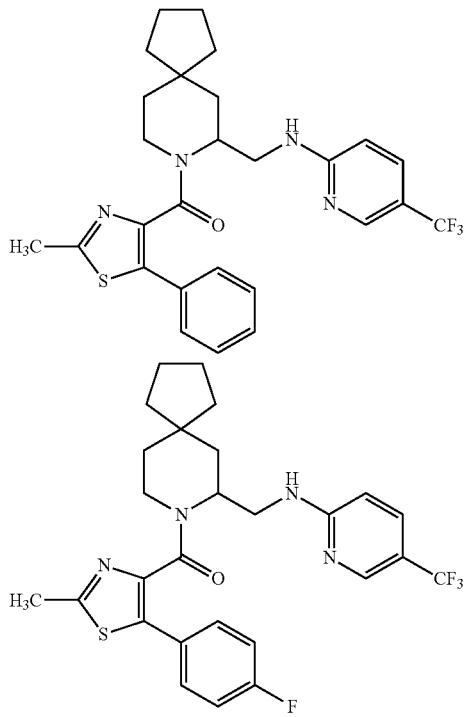

(2-methyl-5-p-tolylthiazol-4-yl)(7-((5-(trifluoromethyl)pyridin-2-ylamino)methyl)-8-azaspiro[4.5]decan-8-yl)methanone (5-(4-fluorophenyl)-2-methylthiazol-4-yl)(7-((5-(trifluoromethyl)pyridin-2-ylamino)methyl)-8-azaspiro[4.5]decan-8-yl)methanone

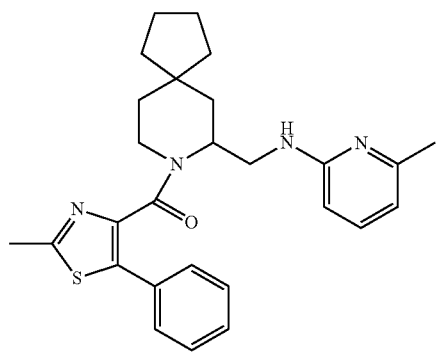

(±)(2-methyl-5-phenylthiazol-4-yl)(7-(((6-methylpyridin-2-yl)amino)methyl)-8-azaspiro[4.5]decan-8-yl)methanone

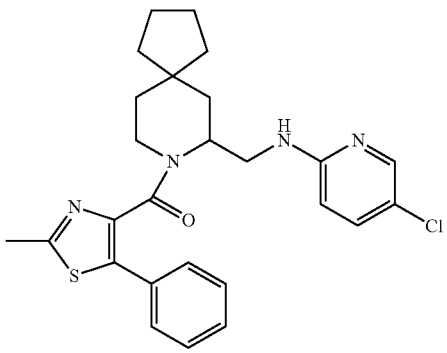 [SMILES: Cc1nc(C(=O)N2CCC3(CCCC3)CC2CNc2ccc(Cl)cn2)c(-c2ccccc2)s1]

(±)(7-(((5-chloropyridin-2-yl)amino)methyl)-8-azaspiro[4.5]decan-8-yl)(2-methyl-5-phenylthiazol-4-yl)methanone

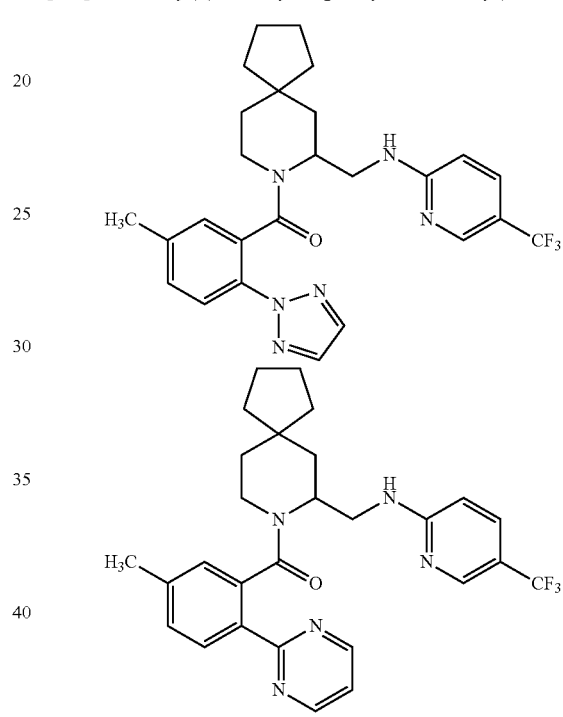

(5-methyl-2-(2H-1,2,3-triazol-2-yl)phenyl)(7-((5-(trifluoromethyl)pyridin-2-ylamino)methyl)-8-azaspiro[4.5]decan-8-yl)methanone (5-methyl-2-(pyrimidin-2-yl)phenyl)(7-((5-(trifluoromethyl)pyridin-2-ylamino)methyl)-8-azaspiro[4.5]decan-8-yl)methanone When n=1, m is preferably equal to 1.

In this embodiment:
Q is preferably selected from pyridyl, pyridyl substituted with one or more halogens; pyridyl substituted with $(C_1-C_3)$alkyl;
R is preferably selected from phenyl and a 5-membered heteroaromatic ring comprising two or three heteroatoms selected from S, O and N, such R being substituted with one or two substituent selected from $(C_1-C_3)$alkyl, halogen, pyrimidyl, thiazolil, phenyl optionally substituted with one or more halogen atoms, a 5- or 6-membered heterocycle comprising at least one nitrogen atom.

More preferably, Q is pyridyl substituted with one or more halogens; pyridyl substituted with $(C_1-C_3)$alkyl and R is phenyl substituted with one or two substituent selected from $(C_1-C_3)$alkyl and a 5- or 6-membered heterocycle comprising at least one nitrogen atom.

Preferred compounds when m=1 are:

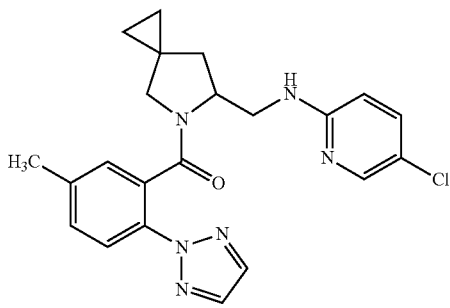

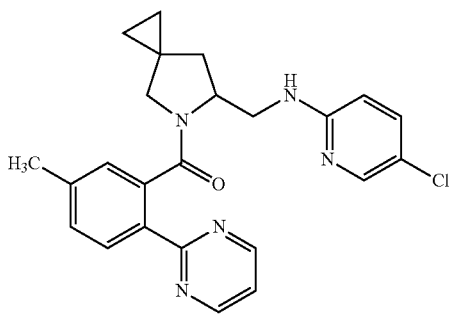

(6-((5-chloropyridin-2-ylamino)methyl)-5-azaspiro[2.4]eptan-5-yl)(5-methyl-2-(2H-1,2,3-triazol-2-yl)phenyl)methanone (6-((5-chloropyridin-2-ylamino)methyl)-5-azaspiro[2.4]eptan-5-yl)(5-methyl-2-(pyrimidin-2-yl)phenyl)methanone;

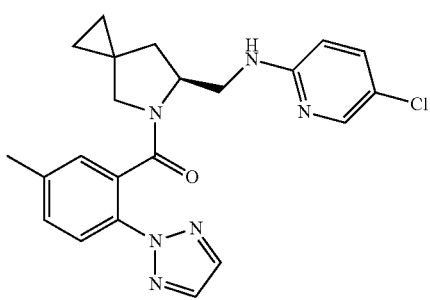 [SMILES: Cc1ccc(-n2nccn2)c(C(=O)N2CC3(CC3)C[C@H]2CNc2ccc(Cl)cn2)c1]

S)-(6-(((5-chloropyridin-2-yl)amino)methyl)-5-azaspiro[2.4]heptan-5-yl)(5-methyl-2-(2H-1,2,3-triazol-2-yl)phenyl)methanone

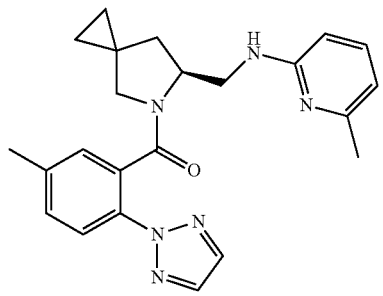 [SMILES: Cc1ccc(-n2nccn2)c(C(=O)N2CC3(CC3)C[C@H]2CNc2cccc(C)n2)c1]

S)-(5-methyl-2-(2H-1,2,3-triazol-2-yl)phenyl)(6-(((6-methylpyridin-2-yl)amino)methyl)-5-azaspiro[2.4]heptan-5-yl)methanone

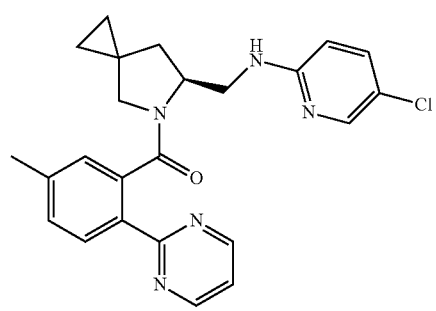 [SMILES: Cc1ccc(-c2ncccn2)c(C(=O)N2CC3(CC3)C[C@H]2CNc2ccc(Cl)cn2)c1]

S)-(6-(((5-chloropyridin-2-yl)amino)methyl)-5-azaspiro[2.4]heptan-5-yl)(5-methyl-2-(pyrimidin-2-yl)phenyl)methanone In a second embodiment, in the spiro-amino compound of Formula (VI), P is COQ. This is a compound of Formula (VIb):

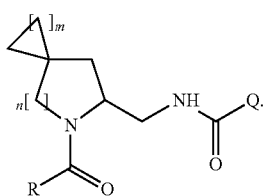

VIb

The disclosure also concerns a process for the preparation of a compound of Formula (VIa) comprising the following steps represented in the below scheme:

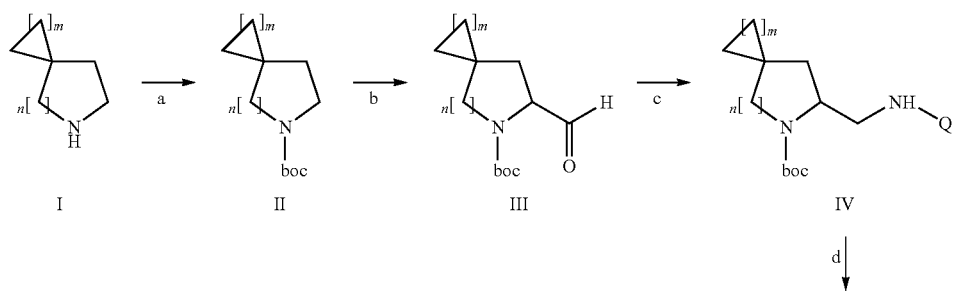

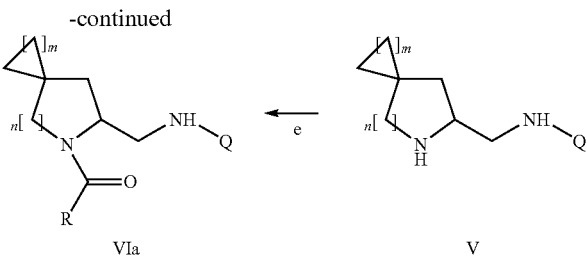

a) protecting a compound of Formula (I) with a BOC protecting group to obtain a compound of Formula (II);

b) reacting a compound of Formula (II) with strong bases and dimethylformamide, thus obtaining a compound of Formula (III);

c) adding an amine of Formula Q-NH$_2$, where Q is selected from the group consisting of phenyl, pyridyl, pyrimidyl, quinolyl, isoquinolyl, quinoxalyl, benzofuranyl, imidazotriazolyl, being such Q optionally substituted with one or more substituents selected from the group consisting of (C$_1$-C$_3$)alkyl, halogen, trifluoromethyl, carbammido, methylcarbammido, carboxy, methylcarboxy, in the presence of a reducing agent to obtain a compound of Formula (IV);

d) cleaving the BOC group from the compound of Formula (IV) to obtain a compound of Formula (V);

e) reacting a compound of Formula (V) with RCOOH in the presence of coupling reagents or with the corresponding acyl chlorides RCOCl in the presence of a base, wherein R is selected between a 5- or 6-membered aromatic ring and a 5- or 6-membered heteroaromatic ring comprising from 1 to 3 heteroatoms selected from S, O and N, such ring being substituted with one or two substituents selected from the group consisting of (C$_1$-C$_3$)alkyl, halogen, (C$_3$-C$_5$)cycloalkyloxy, (C$_1$-C$_3$)alkylcarbonyl, phenyl optionally substituted with one or more halogen atoms, a 5- or 6-membered heterocycle comprising at least one nitrogen atom.

Furthermore the disclosure concerns a process for the preparation of a compound of Formula (VIb) which comprises the following steps represented in the scheme below:

a) protecting a compound of Formula (I) with a BOC protecting group to obtain a compound of Formula (II);

b) reacting a compound of Formula (II) with strong bases and dimethylformamide, thus obtaining a compound of Formula (III);

f) making a reductive amination of the compound of Formula (III) to obtain an amine of Formula (VII);

g) reacting a compound of Formula (VII) with QCOOH in the presence of coupling reagents or with the corresponding acyl chlorides QCOCl in the presence of a base to obtain the amide of Formula (VIII), wherein Q is selected from the group consisting of phenyl, pyridyl, pyrimidyl, quinolyl, isoquinolyl, quinoxalyl, benzofuranyl, imidazotriazolyl, being such Q optionally substituted with one or more substituents selected from the group consisting of (C$_1$-C$_3$)alkyl, halogen, trifluoromethyl, carbammido, methylcarbammido, carboxy, methylcarboxy;

h) cleaving the BOO group from the compound of Formula (VIII) and reacting with RCOOH in the presence of coupling reagents or with the corresponding acyl chlorides RCOCl in the presence of a base to give a compound of Formula VIb, wherein R is selected between a 5- or 6-membered aromatic ring and a 5- or 6-membered heteroaromatic ring comprising 1 to 3 heteroatoms selected from S, O and N, such ring being substituted with one or two substituents selected from the group consisting of (C$_1$-C$_3$)alkyl, halogen, (C$_3$-C$_5$)cycloalkyloxy, (C$_1$-C$_3$)alkylcarbonyl, phenyl optionally substituted with one or more halogen atoms, a 5- or 6-membered heterocycle comprising at least one nitrogen atom.

Compounds of Formula (I) of step a) are either commercially available and/or described in literature. In step b), sec-BuLi could be used among strong bases.

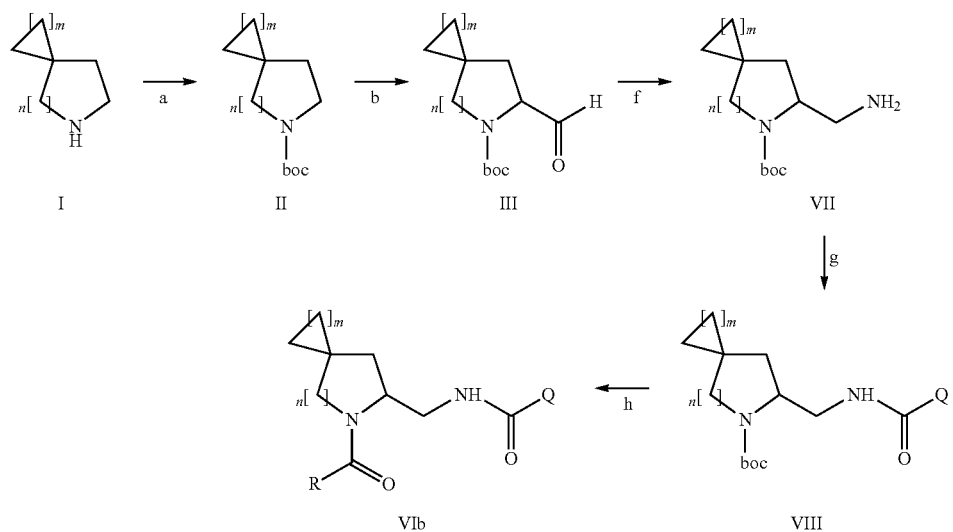

In the most preferred embodiment the disclosure concerns piperidine compounds with a Spiro ring of three carbon atoms.

A further subject of the disclosure is also the preparation of compounds of Formula VIa wherein m=1 and n=2, comprising the following steps:

a) reacting a compound of formula (I) with tertbutyl dicarbonate in an organic solvent to obtain a compound of Formula (II);

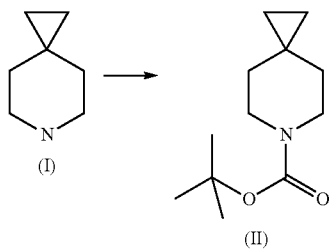

b) reacting compounds of Formula (II) with a strong base and dimethylformamide; to give a compound of Formula (III)

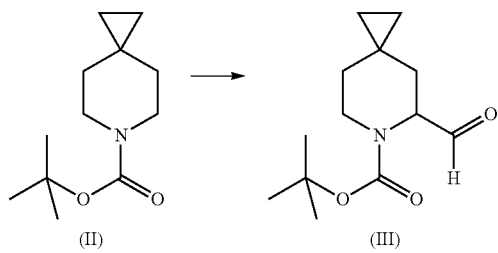

or reacting compounds of Formula (II) with a base and N,N, N'N'-tetramethyl ethylendiammine at −60° C. in an organic solvent and then with dimethylformamide at −78° C.;

c) reacting compounds of Formula (III) with compounds of Formula Q-NH$_2$, by using a reducing agent in an organic solvent for about 18 hours at room temperature to give compounds of Formula (IV), wherein Q is selected from the group consisting of phenyl, pyridyl, pyrimidyl, quinolyl, isoquinolyl, quinoxalyl, benzofuranyl, imidazotriazolyl, being such Q optionally substituted with one or more substituents selected from the group consisting of (C$_1$-C$_3$)alkyl, halogen, trifluoromethyl, carbammido, methylcarbammido, carboxy, methylcarboxy;

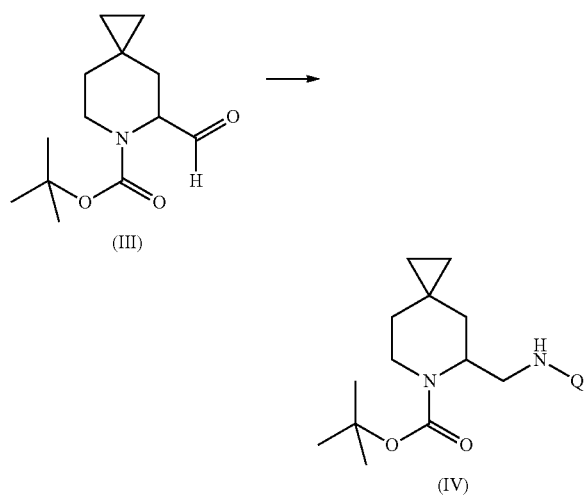

d) reacting compounds of Formula (IV) with trifluoroacetic acid in a suitable organic for about 4 hours to give compounds of Formula (V);

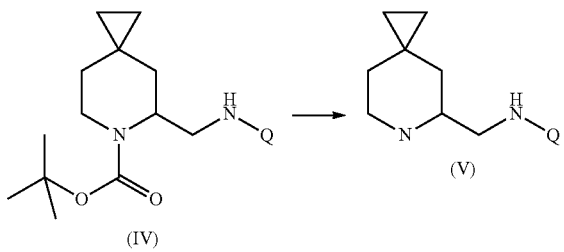

e) reacting compounds of Formula (V) with compounds of formula RCOOH by using a suitable condensing agent and a base in an organic solvent for about 18 hours to give compounds of Formula (VIa), wherein R is selected from a 5- or 6-membered aromatic ring and a 5- or 6-membered heteroaromatic ring comprising 1 to 3 heteroatoms selected from S, O and N, such ring being substituted with one or two substituents selected from the group consisting of (C$_1$-C$_3$) alkyl, halogen, (C$_3$-C$_5$)cycloalkyloxy, (C$_1$-C$_3$)alkylcarbonyl, phenyl optionally substituted with one or more halogen atoms, a 5- or 6-membered heterocycle comprising at least one nitrogen atom

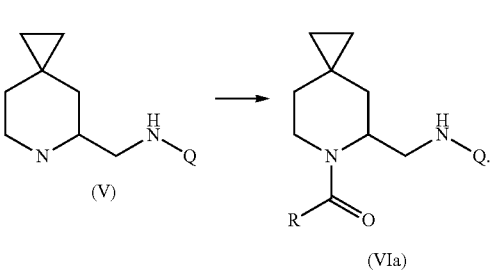

The process for the preparation of compounds of Formula VIa where m=1 and n=2 provides for preferably the use of dichloromethane as organic solvent in step d) and NaBH (OAc)$_3$ in dichloroethane in step c).

The preferred coupling agent in step e) is O-(Benzotriazol-1-yl)N,N,N',N'-tetramethyluronio hexafluorophosphate, diisopropyl ethyl amine as base, dimethyllformammide/dichloromethane as solvents.

According to the disclosure, the compounds are obtained using a simple process, easy to scale-up and avoiding lengthy and expensive preparation steps, obtaining high yield of a stable pharmaceutical grade compound.

The compounds of the disclosure as such or a pharmaceutically acceptable salt thereof could be used in medicine, in particular as antagonists of the Orexin 1 receptor.

They could be used in combination with an pharmaceutically acceptable carrier and, optionally, with suitable excipients, to obtain pharmaceutical compositions. The term "pharmaceutically acceptable carrier" means solvents, carrier agents, diluting agents and the like which are used in the administration of compounds of the disclosure.

Such pharmaceutical compositions can be administered by parenteral, oral, buccal, sublingual, nasal, rectal, topical or transdermal administration.

Compositions of this disclosure suitable for the oral administration will be conveniently discrete units such as tablets, capsules, cachet, powders or pellets, or as liquid suspension.

The tablets can contain also suitable excipients routinely used in pharmaceutical field such as pre-gelatinised starch, microcrystalline cellulose, sodium glycolate starch, talc, lactose, magnesium stearate, sucrose, stearic acid, mannitol.

Compositions for parenteral administration conveniently include sterile preparations.

Compositions for topical administration may conveniently be formulated as creams, pastes, oils, ointments, emulsions, foams, gels, drops, spray solutions and transdermal patches.

The compounds of the disclosure could be used for manufacturing a medicament for the treatment of pathologies which require the use of an antagonist of the OX1 receptor, such as the treatment of obesity and sleep disorders, compulsive disorders, drugs and alcohol dependencies, schizophrenia.

The disclosure will be now detailed by means of the following examples relating to the preparation of some disclosure compounds and to the evaluation of their activity against OX1 receptor and OX2 receptor.

In the procedure that follows, after the starting materials, reference to a description is typically provided. The starting material may not necessarily have been prepared from the description referred to. The stereochemistry of the Examples have been assigned on the assumption that the absolute configuration centers are retained.

Reagents used in the following examples were commercially available from various suppliers (for example Sigma-Aldrich, Acros or Apollo scientific) and used without further purifications. Solvents were used in dry form. Reaction in anhydrous environment were run under a positive pressure of dry $N_2$.

Microwave reactions were run on a Biotage Initiator 2.5 instrument.

Proton Nuclear Magnetic Resonance ($^1$H NMR) spectra were recorded on Bruker Avance 400 MHz instrument. Chemical shifts are reported in ppm (δ) using the residual solvent line as internal standard. Splitting patterns are designated as: s, singlet; d, doublet; t, triplet; q, quartet; m, multiplet; b, broad signal. When more than one conformer was detected the chemical shifts of the most abundant one is usually reported.

Mass spectra (MS) were run on a Ion Trap Thermo LCQ classic spectrometer, operating in positive ES(+) and negative ES(−) ionization mode.

HPLC spectra were performed using a Waters Alliance 2965 apparatus and UV-Vis detector Waters 2996. The cromatographic method (using Phenomenex Luna C18, 150*4.6, 5μ) was the following: 35 min of elution at 30° C., mobile phase composed of different acetonitrile/methanol/$KH_2PO_4$ (20 mM pH 2.5) mixtures, flow rate of 0.6 ml/min.

HPLC spectra for chiral purity determinations were performed using a Agilent 1200 apparatus and a UV detector DAD G1315D. The cromatographic method (using a Phenomenex LUX 5u cellulose-1, 250*4.6 mm) was the following: 30 min of elution at 30° C., mobile phase 90% n-hexane 10% ethanol+0.1% DEA, flow rate of 0.5 ml/min.

UPLC spectra were performed on a Waters Acquity UPLC-SQD instrument using an Acquity UPLC-BEH C18 column (1.7 μM, 50×2.1 mm).

Purifications by means of preparative chiral HPLC were performed using a

Shimadzu Preparative Liquid Chromatograph LC-8A apparatus and a UV detector SPD-20A. The cromatographic methods (using a Phenomenex LUX 5u cellulose-1, AXIA 250*21.20 mm) were the following:

A: mobile phase 90% n-hexane 10% ethanol+0.1% DEA, flow rate of 10 ml/min.

B: mobile phase 60% n-hexane 40% ethanol+0.1% DEA, flow rate of 10 ml/min.

C: mobile phase 93% n-hexane 7% isopropanol+0.1% DEA, flow rate of 10 ml/min.

D: mobile phase 95% n-hexane 5% isopropanol+0.1% DEA, flow rate of 10 ml/min.

E: mobile phase 80% n-hexane 20% ethanol+0.1% DEA, flow rate of 10 ml/min.

Flash silica gel chromatography was carried out on silica gel 230-400 mesh (supplied by Merck AG Darmstadt, Germany); in a number of preparations, Biotage automatic flash chromatography systems (Sp1 and Isolera systems) were performed, using Biotage silica cartridges.

Thin layer chromatography was carried out using Merck TLC plates Kieselgel 60E-254, visualized with UV light, aqueous permanganate solution, iodine vapours.

Example 1

Preparation of Intermediate 1: 6-azaspiro[2.5]octane hydrobromide

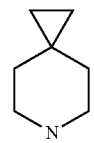

Benzyl 6-azaspiro[2-5]octane-6-carboxylate (9 g, 36 mmol), whose preparation has already been described for example in WO2008084300, was dissolved in HBr35% in AcOH (10 ml) at 0° C. and maintained under stirring for 3 hours. The solution was treated with 200 ml of hexane. After having decanted the solvent, 80 ml of $Et_2O$ were added. The solid obtained was filtered, washed with ether and hexane (50 ml), then dried under vacuum to obtain 6.3 g of intermediate 1 (white cream solid).

MS (ESI) m/z: 112 [M+H]$^+$ $^1$HNMR (DMSO-$d_6$) δ ppm 8.35 (m, 2H) 3.07 (m, 4H) 1.50-1.54 (m, 4H) 0.38 (s, 4H).

Example 2

Preparation of Intermediate 2: tert-butyl 6-azaspiro[2.5]octane-6-carboxylate

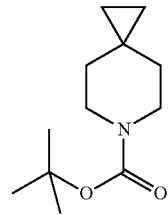

To a suspension of 6-azaspiro[2.5]octane hydrobromide (Intermediate 1, 3.4 g, 17.6 mmol) in dichloromethane (50 ml), which was cooled to 0° C., triethylamine (5.14 ml, 3.9 mmol) was added then a solution of tert-butyl dicarbonate (4.24 g, 19.4 mmol) in dichloromethane (20 ml) was added in 20 minutes. The clear solution was maintained under stirring at room temperature for 18 hours, then dichloromethane (50 ml) was added and the organic solution was washed with water (2×20 ml), HCl 0.5N (20 ml) then water (2×20 ml). The organic solvent was anhydrified ($Na_2SO_4$) and evaporated to give 3.7 g of intermediate 2 (light yellow solid).

¹HNMR (CDCl₃) δ ppm 3.43 (m, 4H) 1.46 (s, 9H) 1.32 (m, 4H) 0.32 (s, 4H).

Example 3

Preparation of Intermediate 3: (±) tert-butyl 5-formyl-6-azaspiro[2.5]octane-6-carboxylate

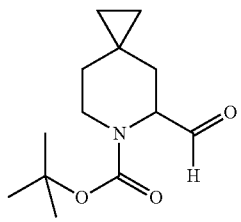 [SMILES: CC(C)(C)OC(=O)N1CCC2(CC2)CC1C=O]

tert-butyl 6-azaspiro[2.5]octane-6-carboxylate (Intermediate 2, 1 g, 4.73 mmol) dissolved in 20 ml of Et₂O was cooled to −60° C., then N,N,N',N'-tetramethyl ethylendiamine (0.71 ml, 4.73 mmol) and secBuLi 1.4M in hexane (4.05 ml, 5.68 mmol) were added. After 10 minutes at −60° C., the temperature was raised to −20° C. for 30 minutes, then the reaction was cooled to −78° C. and dimethylformamide (0.55 ml, 7.09 mmol, dissolved in 5 ml of Et₂O) was added. After 30 minutes a saturated aqueous solution of NH₄Cl (8 ml) was slowly added, then reaction was allowed to reach room temperature. Reaction was extracted with Et₂O (3×50 ml), the organic solvent was dried (Na₂SO₄) and evaporated to obtain a crude that was purified by silica gel chromatography (petroleum ether/ethylacetate from 95/5 to 85/15). (±) tert-butyl 5-formyl-6-azaspiro[2.5]octane-6-carboxylate was obtained as light yellow solid (400 mg).

MS (ESI) m/z 262 [M+Na]⁺.

¹HNMR (CDCl₃) δ ppm 9.65 (s, 1H) 4.61 (m, 1H) 4.02 (m, 1H) 3.10 (m, 1H) 2.08 (m, 1H) 1.80 (m, 1H) 1.51 (m, 1H) 1.49 (s, 9H) 0.88 (m, 1H) 0.35-0.42 (m, 4H).

Example 4

Preparation of Intermediate 4: (±)tert-butyl 5-((6-methylpyridin-2-ylamino)methyl)-6-azaspiro[2.5]octane-6-carboxylate

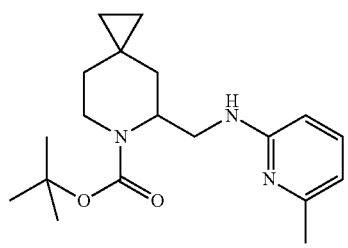 [SMILES: Cc1cccc(NCC2CC3(CCN2C(=O)OC(C)(C)C)CC3)n1]

(±) tert-butyl 5-formyl-6-azaspiro[2.5]octane-6-carboxylate (Intermediate 3, 400 mg, 1.67 mmol) was dissolved in dichloroethane (5 ml), then acetic acid (5 eq) and 2-amino 6 picoline (217 mg, 2.0 mmol) were added. After 3 hours at room temperature NaBH(OAc)₃ (560 mg, 2.63 mmol) was added and the reaction was maintained under stirring at room temperature for 18 hours. The reaction was poured in aqueous NaHCO₃ and extracted with ethylacetate. The organic layers were combined, dried (Na₂SO₄) and concentrated under vacuum; the obtained was purified by silica gel column chromatography (petroleum ether/ethyl acetate=8/2 to 1/1). 360 mg of intermediate 4 were obtained as colourless oil.

MS (ESI) m/z: 354 [M+Na]⁺. ¹HNMR (CDCl₃) δ ppm 7.32 (m, 1H) 6.44 (d, 1H) 6.24 (d, 1H) 4.65 (m, 1H) 4.55 (m, 1H) 4.10 (m, 1H) 3.37 (m, 1H) 3.05 (m, 1H) 2.37 (s, 3H) 1.8-2.1 (m, 2H) 1.49 (s, 9H) 1.15 (m, 1H) 0.85 (m, H) 0.25-0.48 (m, 4H).

Example 5

Preparation of Intermediate 5: (±)tert-butyl 5-((5-chloropyridin-2-ylamino)methyl)-6-azaspiro[2.5]octane-6-carboxylate

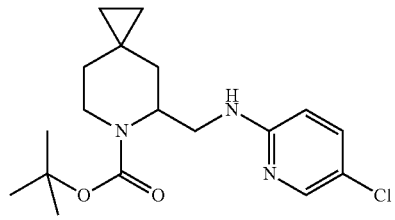 [SMILES: CC(C)(C)OC(=O)N1CCC2(CC2)CC1CNc1ccc(Cl)cn1]

(±) tert-butyl 5-formyl-6-azaspiro[2.5]octane-6-carboxylate (Intermediate 3, 450 mg, 1.88 mmol) was dissolved in dichloroethane (5 ml), then acetic acid (5 eq) and 2-amino 5 chloropyridine (290 mg, 2.25 mmol) were added. After 3 hours at room temperature NaBH(OAc)₃ (636 mg, 3.0 mmol) was added and the reaction was maintained under stirring at room temperature for 18 hours. The reaction was poured in aqueous NaHCO₃ and extracted with ethyl acetate. The organic layers were combined, dried (Na₂SO₄) and concentrated under vacuum; crude product was purified by silica gel column chromatography using Petroleum ether/Ethyl acetate=8/2. 240 mg of Intermediate 5 were obtained as colourless oil.

¹HNMR (CDCl₃) δ ppm 8.03 (d, 1H) 7.33 (dd, 1H) 6.33 (d, 1H) 4.7 (m, 1H) 4.57 (m, 1H) 4.13 (m, 1H) 3.85 (m, 1H) 3.36 (m, 1H) 2.99 (m, 1H) 2.16 (m, 1H) 1.88-1.95 (m, 1H) 1.42 (s, 9H) 0.99 (m, 1H) 0.82 (m, H) 0.45-0.50 (m, 2H) 0.28-0.32 (m, 2H).

Example 6

Preparation of Intermediate 6: (±) tert-butyl 5-((5-trifluoromethylpyridin-2-ylamino)methyl)-6-azaspiro[2.5]octane-6-carboxylate

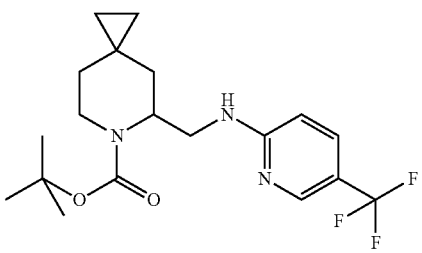 [SMILES: CC(C)(C)OC(=O)N1CCC2(CC2)CC1CNc1ccc(C(F)(F)F)cn1]

(±) tert-butyl 5-formyl-6-azaspiro[2.5]octane-6-carboxylate (Intermediate 3, 450 mg, 1.88 mmol) was dissolved in dichloroethane (5 ml), then acetic acid (5 eq) and 2-amino 5 trifluoromethylpyridine (365 mg, 2.25 mmol) were added. After 3 hours at room temperature NaBH(OAc)$_3$ (636 mg, 3.0 mmol) was added and the reaction was maintained under stirring at room temperature for 18 hours. The reaction was poured in aqueous NaHCO$_3$ and extracted with ethylacetate. The organic layers were combined, dried (Na$_2$SO$_4$) and concentrated under vacuum; the crude was purified by silica gel column chromatography, using a gradient dichloromethane to dichloromethane/Ethyl acetate=95/5). 200 mg of Intermediate 6 as yellow oil were obtained.

MS (ESI) m/z: 408 [M+Na]$^+$ $^1$HNMR (CDCl$_3$) δ ppm 8.35 (s, 1H) 7.6 (d, 1H) 6.5 (d, 1H) 5.85 (m, 1H) 5.40 (d, 1H) 5.15 (m, 1H) 3.75 (m, 1H) 3.51 (m, 1H) 2.25-2.45 (m, 2H) 1.40-1.75 (m, 10H) 0.3-0.55 (m, 4H).

Example 7

Preparation of Intermediate 7: (±) N-(6 azaspiro[2.5] octan-5-ylmethyl)-6-methylpyridin-2-amine

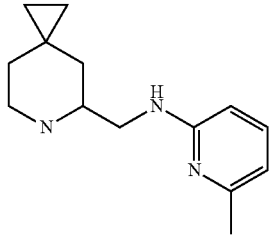 [SMILES: Cc1cccc(NCC2CC3(CCN2)CC3)n1]

(±) tert-butyl 5-((6-methylpyridin-2-ylamino)methyl)-6-azaspiro[2.5]octane-6-carboxylate (intermediate 4, 350 mg, 1.05 mmol) was dissolved in dichloromethane (10 ml) and cooled to 0° C., then trifluoroacetic acid (2 ml) was added. After 1 hour at 0° C. and 2 hours at room temperature the solution was evaporated, the residue re-dissolved in dichloromethane was washed with saturated NaHCO$_3$ aqueous solution. The organic layers were dried (Na$_2$SO$_4$) and concentrated under vacuum; the crude was purified by silica gel column chromatography (CHCl$_3$/MeOH=8/2). 65 mg of Intermediate 7 as light yellow oil were obtained.

MS (ESI) m/z: 232 [M+H]$^+$ $^1$HNMR (CDCl$_3$) δ ppm 7.32 (m, 1H) 6.46 (d, 1H) 6.32 (d, 1H) 5.75 (m, 1H) 3.45-3.65 (m, 4H) 3.05 (m, 1H) 2.42 (s, 3H) 2.06-2.18 (m, 1H) 1.0-1.29 (m, 2H) 0.36-0.52 (m, 4H).

Example 8

Preparation of Intermediate 8: (±) (6 azaspiro[2.5] octan-5-ylmethyl)-5-choropyridin-2-amine

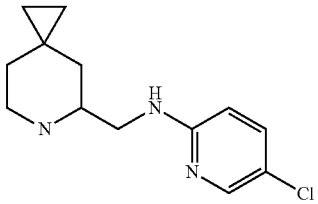 [SMILES: Clc1ccc(NCC2CC3(CCN2)CC3)nc1]

(±) tert-butyl 5-((5-chloropyridin-2-ylamino)methyl)-6-azaspiro[2.5]octane-6-carboxylate (intermediate 5, 240 mg, 0.68 mmol) was dissolved in dichloromethane (10 ml) and cooled to 0° C., then trifluoroacetic acid (2 ml) was added. After 1 hour at 0° C. and 2 hours at room temperature the solution was evaporated, the residue dissolved in dichloromethane was washed with saturated NaHCO$_3$ aqueous solution. The combined organic layers were dried (Na$_2$SO$_4$) and concentrated under vacuum; the crude was purified by silica gel column chromatography (gradient of dichloromethane to dichloromethane/MeOH=9/1). 150 mg of Intermediate 8 as light yellow oil were obtained.

$^1$HNMR (CDCl$_3$) δ ppm 7.96 (d, 1H) 7.30 (m, 1H) 6.42 (d, 1H) 6.25 (m, 1H) 3.74 (m, 1H) 3.37-3.55 (m, 3H) 2.93 (m, 1H) 2.20 (m, 1H) 2.0-2.66 (m, 1H) 1.20 (m, 1H) 1.04 (m, 1H) 0.42-0.58 (m, 4H).

Example 9

Preparation of Intermediate 9: (±) N-(6 azaspiro[2.5] octan-5-ylmethyl)-5-(trifluoromethyl)pyridin-2-amine

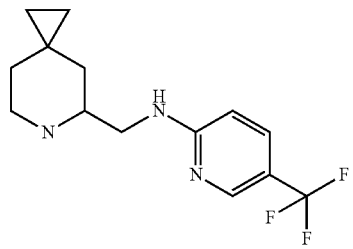 [SMILES: FC(F)(F)c1ccc(NCC2CC3(CCN2)CC3)nc1]

(±) tert-butyl 5-((5-trifluoromethylpyridin-2-ylamino)methyl)-6-azaspiro[2.5]octane-6-carboxylate (intermediate 5, 200 mg, 0.520 mmol) was dissolved in dichloromethane (10 ml) and cooled to 0° C., then trifluoroacetic acid (2 ml) was added. After 1 hour at 0° C. and 18 hours at room temperature the solution was evaporated, the residue dissolved in dichloromethane was washed with saturated NaHCO$_3$ aqueous solution. The combined organic layers were dried (Na$_2$SO$_4$) and concentrated under vacuum; the obtained crude was purified by silica gel column chromatography (gradient from dichloromethane/ethylacetate=9/1 to dichloromethane/MeOH=9/1). 60 mg of Intermediate 9 were obtained as light yellow oil.

MS (ESI) m/z: 286 [M+H]$^+$.

Example 10

Preparation of Intermediate 10: methyl 2-(6-azaspiro [2.5]octan-5-ylmethylamino)-5-chlorobenzoate

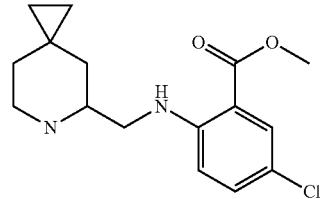 [SMILES: COC(=O)c1cc(Cl)ccc1NCC1CC2(CCN1)CC2]

To a solution of (±) tert-butyl 5-formyl-6-azaspiro[2.5] octane-6-carboxylate (intermediate 3) (160 mg, 0.669 mmole) in dichloroethane (10 ml), methyl 2-amino-5-chlorobenzoate (149 mg, 0.802 mmole) and glacial AcOH (0.191 ml, 3.343 mmole) were added. The reaction mixture was left to room temperature for 3 hours, then sodium triacetoxyborohydride (227 mg, 1.070 mmole) was added and the reaction mixture was stirred at the same temperature overnight. The mixture was diluted with dichloromethane and washed with NaHCO$_3$ saturated solution (2×). The organic phase was separated on separating cartridge and evaporated. the obtained residue (273 mg, 0.669 mmole) was dissolved in 3:1 trifluoroacetric acid:dichloromethane mixture (1.2:0.4 ml), by cooling in an ice bath. The reaction mixture was then stirred for 2 hours at room temperature. Solvents were evaporated, then the residue was dissolved in dichloromethane and the solution was washed with NaHCO$_3$ saturated solution (2×). After evaporation of the organic phase the residue was purified by SPE-Si cartridge (5 g) eluting with a mixture dichloromethane: MeOH (from dichloromethane to dichloromethane: MeOH 95:5). 78 mg of intermediate 10 were obtained.

1H NMR: (CDCl3) δ ppm 7.87-7.86 (d, 2H), 7.3-7.27 (dd, 1H) 6.68-6-66 (d, 1H) 3.87 (s, 3H) 3.25-3.21 (m, 2H) 3.15-3.11 (m, 1H) 3.06-3.0 (m, 1H) 2.86-2.79 (dt, 1H) 2.74 (bs, 1H) 1.98-1.91 (dt, 1H) 1.78-1.72 (t, 1H) 0.97-0.93 (m, 1H) 0.88-0.83 (m, 1H) 0.41-0.35 (m, 2H) 0.32-0.28 (m, 2H)

Example 11

Preparation of Intermediate 12: (S)-2-[tert-butoxycarbonyl-(2-methoxycarbonyl-ethyl)-amino]-succinic acid 4-methyl ester

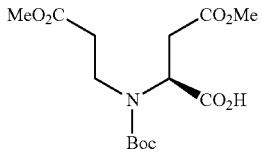

To a solution of (S)-2-amino-succinic acid 4-methyl ester hydrochloride (intermediate 11, 250 g, 1.36 mol) in water (600 ml) cooled to 0° C. was added triethylamine (474 ml, 3.4 mol) and meth acrylate (368 ml, 4.09 mol). The mixture was stirred vigorously and warmed to room temperature. After washing with petroleum ether (2×2 L), tert-butanol (200 ml) and Boc$_2$O (370 g, 1.70 mol) were added and vigorous stirred continued for 16 hours. The mixture was washed with petroleum ether (2×2 L). The aqueous solution was cooled to 0° C. and the value of pH was adjusted to 3.0 with concentrated HCl. The product was extracted with ethyl acetate (3×1 L) and the organic extracts were combined, washed with saturated NaCl (14 dried (Na$_2$SO$_4$) and evaporated to give 420 g (yield: 92%) of (S)-2-[tert-butoxycarbonyl-(2-methoxycarbonyl-ethyl)-amino]-succinic acid 4-methyl ester.

$^1$HNMR (CDCl$_3$) δ ppm 5.45 (s, 1H), 4.44 (m, 1H), 3.80-3.87 (m, 1H), 3.71 (s, 3H), 3.68 (s, 3H), 3.45-3.53 (m, 1H), 3.20 (m, 1H), 2.57-2.90 (m, 3H), 1.43 (s, 9H)

Example 12

Preparation of Intermediate 13: (S)-4-oxo-piperidine-1,2-dicarboxylic acid 1-tert-butyl ester tert-butylamine salt

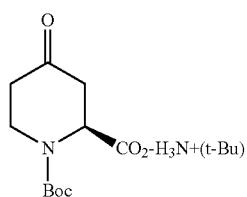

To a solution of (S)-2-[tert-Butoxycarbonyl-(2-methoxycarbonyl-ethyl)-amino]-succinic acid 4-methyl ester (intermediate 12, 420 g, 1.35 mol) in THF (2 L) under nitrogen cooled to 0° C. was added NaOMe/MeOH (1.5 L, 2.7M) in half an hour. The resulting yellow solution was stirred at 85° C. for 3 hours (after 1 hour a suspension was obtained). THF (1.5 L) was distilled off under the reduced pressure and water (2 L) was added. The resulting mixture was stirred at 110° C. for 20 hours. The mixture was washed with ethyl acetate (2×1 L). The aqueous solution was cooled to 0° C. and the value of pH was adjusted to 2.5 with concentrated HCl. The product was extracted with ethyl acetate (3×1 L) and the organic extracts were combined, washed with saturated NaCl (1 L), dried (Na$_2$SO$_4$) and filtered. The filtrate was cooled to 0° C. and tert-butylamine (145 ml, 1.35 mol) was added with stirring. The yellow solid was collected by filtration and dried, then boiled in isopropyl alcohol (1.5 L). The suspension was cooled to 5° C. and collected by filtration to give 180 g of intermediate 3 (light white solid, yield:45%).

$^1$HNMR (D$_2$O) δ ppm 8.94 (s, 1H), 5.10 (m, 1H), 4.06 (m, 1H), 3.70 (m, 1H), 2.86 (m, 2H), 2.55 (m, 2H), 1.47 (s, 9H)

$[α]_D^{25}$-14.4 (c1.0, H$_2$O)

Example 13

Preparation of Intermediate 14: (S)-4-oxo-piperidine-1,2-dicarboxylic acid 2-benzyl ester 1-tert-butyl ester

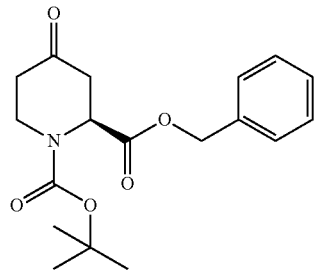 [SMILES: CC(C)(C)OC(=O)N1CCC(=O)C[C@H]1C(=O)OCc1ccccc1]

To a suspension of (S)-4-oxo-piperidine-1,2-dicarboxylic acid 1-tert-butyl ester tert-butylamine salt (intermediate 13, 300 g, 0.95 mol) in ethyl acetate (2.5 L) stirred at 0° C. was slowly added aqueous HCl 0.5N (3 L) saturated with NaCl. After complete dissolution was observed, the organic layer was decanted, and washed with saturated NaCl, dried (Na$_2$SO$_4$) and evaporated to yield 200 g of acid derivative. To a solution of acid derivative (200 g, 0.82 mol) in anhydrous dichloromethane (1.5 L) was added benzyl alcohol (88.9 g, 0.82 mol), N,N'-dicyclohexylcarbodiimide (186 g, 0.91 mol), 4-dimethylaminopyridine (11 g, 0.09 mol) at 0° C., then warmed to room temperature, and stirred at room temperature for 10 hours. The mixture was filtered and the liquid phase was evaporated to obtain a crude that was purified by silica gel chromatography (petroleum ether/ethyl acetate from 10/1 to 5/1). (S)-4-Oxo-piperidine-1,2-dicarboxylic acid 2-benzyl ester 1-tert-butyl ester was obtained as colourless oil (210 g), yield:73%.

$^1$HNMR (CDCl$_3$) δ ppm 7.34-7.41 (m, 5H), 5.20 (s, 2H), 4.91 (m, 1H), 4.08 (m, 1H), 3.70 (m, 1H), 2.82 (m, 2H), 2.51 (m, 2H), 1.45 (d, 9H)

Example 14

Preparation of Intermediate 15: (S)-4-methylene-piperidine-1,2-dicarboxylic acid 2-benzyl ester 1-tert-butyl ester

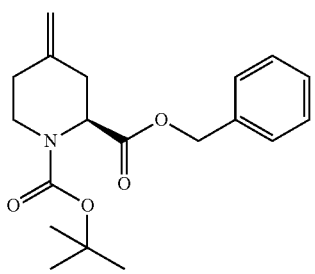 [SMILES: C=C1CCN(C(=O)OC(C)(C)C)[C@H](C(=O)OCc2ccccc2)C1]

To a suspension of methyl(triphenyl)phosphonium bromide (248 g, 0.69 mol) in anhydrous toluene (1 L) was added sodium hexamethyldisilazide (258 ml, 0.69 mmol) at 0° C., after addition was completed, the reaction mixture was warmed to room temperature, and stirred at room temperature for 1 hour, then cooled to 0° C. and the solution of (S)-4-oxo-piperidine-1,2-dicarboxylic acid 2-benzyl ester 1-tert-butyl ester (intermediate 14, 210 g, 0.63 mol) in anhydrous toluene (0.5 L) was added. The resulting mixture was warmed to room temperature, and stirred at room temperature for 1 hour, added water (500 ml), extracted with ethyl acetate. The combined organic extracts were dried ($Na_2SO_4$), filtered and evaporated to obtain a crude that was purified by silica gel chromatography (petroleum ether/ethyl acetate from 10/1 to 5/1). (S)-4-Methylene-piperidine-1,2-dicarboxylic acid 2-benzyl ester 1-tert-butyl ester was obtained as colourless oil (120 g), yield:57.4%.

$^1$HNMR ($CDCl_3$) δ ppm 7.29-7.41 (m, 5H), 4.73-5.25 (m, 5H), 4.14 (m, 1H), 3.06 (m, 1H), 3.80 (m, 1H), 2.47 (m, 1H), 2.13 (m, 2H), 1.35 (d, 9H)

Example 15

Preparation of Intermediate 16: (S)-6-aza-spiro[2.5]octane-5,6-dicarboxylic acid 5-benzyl ester 6-tert-butyl ester

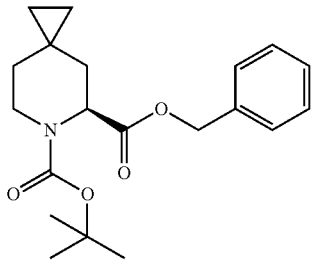 [SMILES: CC(C)(C)OC(=O)N1CCC2(CC2)C[C@H]1C(=O)OCc1ccccc1]

To a solution of (S)-4-methylene-piperidine-1,2-dicarboxylic acid 2-benzyl ester 1-tert-butyl ester (intermediate 15 prepared by Method A, 120 g, 0.36 mol) in anhydrous THF (1 L) was added diazomethane in ether (500 ml) [which was prepared from methyl-3-nitro-1-nitroxoguanide (213 g) in 40% KOH (1 L)] at −25° C. to −35° C. slowly under the protection of nitrogen and warmed to room temperature slowly (about 4 hours) and stirred at room temperature for 10 hours. The mixture is filtered and the liquid phase was evaporated to obtain a crude that was purified by silica gel chromatography (petroleum ether/ethyl acetate from 10/1 to 5/1). (S)-6-Aza-spiro[2.5]octane-5,6-dicarboxylic acid 5-benzyl ester 6-tert-butyl ester was obtained as colourless oil (110 g), yield:88%.

$^1$HNMR ($CDCl_3$) δ ppm 7.36 (m, 5H), 5.14-5.33 (m, 2H), 4.90 (m, 1H), 3.98 (m, 1H), 3.17 (m, 1H), 2.19 (m, 1H), 1.92 (m, 1H), 1.42 (d, 9H), 0.80 (m, 1H), 0.10-0.30 (m, 4H)

Example 16

Preparation of Intermediate 17: (S)-6-aza-spiro[2.5]octane-5,6-dicarboxylic acid 6-tert-butyl ester

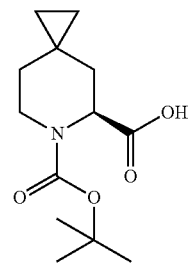 [SMILES: CC(C)(C)OC(=O)N1CCC2(CC2)C[C@H]1C(=O)O]

To a solution of (S)-6-aza-spiro[2.5]octane-5,6-dicarboxylic acid 5-benzyl ester 6-tert-butyl ester (intermediate 16, 110 g, 0.32 mol, ee:66%) in anhydrous methanol (1 L) was added $Pd/BaSO_4$ (50 g) under hydrogen, the reaction mixture was stirred at room temperature for overnight. The resulting mixture was filtered and the liquid phase was evaporated to give 68 g of (S)-6-aza-spiro[2.5]octane-5,6-dicarboxylic acid 6-tert-butyl ester (light white solid, yield:85%) which was recrystallized with PE/EtOAc (4:1) to give 38 g of (S)-6-aza-spiro[2.5]octane-5,6-dicarboxylic acid 6-tert-butyl ester.

$^1$HNMR (CDCl3) δ ppm 12.67 (s, 1H), 4.60 (m, 2H), 3.85 (m, 1H), 3.10 (m, 1H), 2.08 (m, 1H), 1.79 (m, 1H), 1.40 (d, 9H), 0.84 (m, 1H), 0.28-0.32 (m, 4H)

Example 17

Preparation of Intermediate 18: (S)-5-hydroxymethyl-6-aza-spiro[2.5]octane-6-carboxylic acid tert-butyl ester

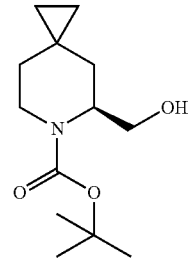 [SMILES: CC(C)(C)OC(=O)N1CCC2(CC2)C[C@H]1CO]

To a solution of (S)-6-aza-spiro[2.5]octane-5,6-dicarboxylic acid 6-tert-butyl ester (intermediate 17, 35 g, 0.122 mol) in anhydrous THF (300 ml) was added $BH_3$/THF (1M, 360 ml, 0.365 mol) under nitrogen at 0° C. After the addition was completed, the reaction mixture was warmed to room temperature and stirred at room temperature for overnight. The resulting mixture was evaporated to obtain a crude that was purified by silica gel chromatography (petroleum ether/ethyl acetate from 10/1 to 5/1). (S)-5-Hydroxymethyl-6-aza-spiro [2.5]octane-6-carboxylic acid tert-butyl ester was obtained as colourless oil (31 g), yield:86%.

$^1$HNMR (CDCl3) δ ppm 4.40 (m, 1H), 4.01 (m, 1H), 3.66 (m, 1H), 3.06 (m, 1H), 2.03 (m, 1H), 1.87 (m, 1H), 1.50 (s, 9H), 1.02 (d, 1H), 0.85 (d, 1H), 0.27-0.43 (m, 4H);

MS Calcd.: 241; MS Found: 142 ([M−100+1]$^+$).

Alternatively Intermediate 18 was prepared from Intermediate 16. To a suspension of lithium aluminium hydride (0.57 g, 15 mmol) in anhydrous THF (30 ml) was added the solution of (S)-6-aza-spiro[2.5]octane-5,6-dicarboxylic acid 5-benzyl ester 6-tert-butyl ester (intermediate 16, 3.45 g, 10 mmol) in THF(20 ml) at 0° C., after the addition was completed, the reaction mixture was stirred at 0° C. for 2 hours. The resulting mixture was quenched with Na$_2$SO$_4$.10H$_2$O, filtered and the filtration was dried (Na$_2$SO$_4$) and evaporated to obtain a crude that was purified by silica gel chromatography (petroleum ether/ethyl acetate from 10/1 to 5/1). (S)-5-Hydroxymethyl-6-aza-spiro[2.5]octane-6-carboxylic acid tert-butyl ester was obtained as colourless oil (2.0 g), yield:83%.

Example 18

Preparation of Intermediate 19: (S) tert-butyl 5-formyl-6-azaspiro[2.5]octane-6-carboxylate

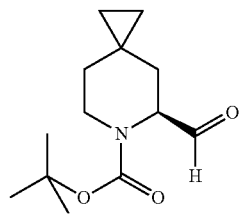 [SMILES: CC(C)(C)OC(=O)N1CCC2(CC2)C[C@H]1C=O]

To (S)-tert-butyl 5-(hydroxymethyl)-6-azaspiro[2.5]octane-6-carboxylate (Intermediate 18, 20 g, 82.0 mmol) dissolved in 80 ml of DCM, TEMPO (2.6 g, 16 mmol) and BAIB (29.3 g, 90 mmol) were added. After 2 hours at 25° C., the reaction is diluted with DCM (150 ml), washed with an aqueous solution of Na$_2$S$_2$O$_3$ then with water, dried (Na$_2$SO$_4$) and evaporated to obtain a crude that was purified by silica gel chromatography (petroleum ether to petroleum ether/ethylacetate 95/5). (S) tert-butyl 5-formyl-6-azaspiro[2.5]octane-6-carboxylate was obtained as light yellow solid (7 g).

$^1$HNMR (CDCl3) δ ppm 9.66 (s, 1H), 4.68 (m, 1H), 3.97 (m, 1H), 3.13 (m, 1H), 2.07 (m, 1H), 1.83 (m, 1H), 1.50 (m, 10H), 0.88 (m, 1H), 0.35-0.50 (m, 2H), 0.20-0.30 (m, 2H)

Example 19

Preparation of Intermediates 20-24

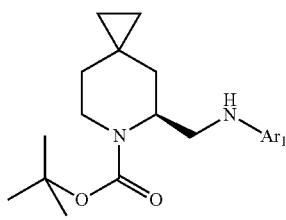

General Procedure 1:

(S) tert-butyl 5-formyl-6-azaspiro[2.5]octane-6-carboxylate (Intermediate 19, 1 eq) was dissolved in dichloroethane (2.5-5 ml/mmol), then acetic acid (5 eq) and the corresponding 2-amino pyridine (1.2 eq) were added. After 1-3 hours at room temperature NaBH(OAc)$_3$ (1.6 eq) was added and the reaction was maintained under stirring at room temperature for 18 hours. The reaction was poured in aqueous NaHCO$_3$ and extracted with ethyl acetate. The organic layers were combined, dried (Na$_2$SO$_4$) and concentrated under vacuum; crude product was purified by silica gel column chromatography using Petroleum ether/Ethyl acetate=8/2 to 1/1 or DCM/MeOH=98/2 to 9/1. Intermediates 20-24 were obtained as oils.

According to general procedure 1 the following intermediates were prepared:

| Intermediate | Name | Yield |
|---|---|---|
| 20 | (S)-tert-butyl 5-(((5-chloropyridin-2-yl)amino) methyl)-6-azaspiro[2.5]octane-6-carboxylate | 66 |
| 21 | (S)-tert-butyl 5-(((5-(trifluoromethyl)pyridin-2-yl) amino)methyl)-6-azaspiro[2.5]octane-6-carboxylate | 17 |
| 22 | (S)-tert-butyl 5-(((6-methylpyridin-2-yl)amino) methyl)-6-azaspiro[2.5]octane-6-carboxylate | 80 |
| 23 | (S)-tert-butyl 5-(((6-chloropyridin-2-yl)amino) methyl)-6-azaspiro[2.5]octane-6-carboxylate | 58 |
| 24 | (S)-tert-butyl 5-(((6-(trifluoromethyl)pyridin-2-yl) amino)methyl)-6-azaspiro[2.5]octane-6-carboxylate | 54 |

Intermediates 20-24 Characterization:

| Intermediate | Ar1 | $^1$H-NMR | MS |
|---|---|---|---|
| 20 | 5-Cl pyridin-2-yl | $^1$HNMR (CDCl$_3$) δ ppm 8.01 (d, J = 2.5 Hz, 1H) 7.37 (dd, J = 9 Hz, 2.5 Hz, 1H) 6.40 (d, J = 9 Hz, 1H) 5.55 (m, 1H) 4.04 (m, 1H) 3.82 (m, 1H) 3.38 (m, 1H) 3.0 (m, 1H) 2.12-2.16 (m, 1H) 1.92 (m, 1H), 1.43 (s, 9H), 1.02 (m, 1H), 0.84 (m, 1H), 0.33-0.49 (m, 4H) | ESI+ m/z 352 [M + 1]$^+$ |
| 21 | 5-CF$_3$ pyridin-2-yl | — | ESI+ m/z 386 [M + 1]$^+$ |
| 22 | 6-methyl pyridin-2-yl | — | ESI+ m/z 332 [M + 1]$^+$ |
| 23 | 6-Cl pyridin-2-yl | — | ESI+ m/z 419 [M + 1]$^+$ |
| 24 | 6-CF$_3$ pyridin-2-yl | — | ESI+ m/z 286 [M + 1]$^+$ − BOC |

Example 20

Preparation of Intermediate 25: (S)-5-(1,3-dioxo-1,3-dihydro-isoindol-2-ylmethyl)-6-aza-spiro[2.5]octne-6-carboxylic acid tert-butyl ester

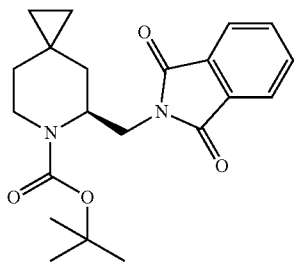 [SMILES: CC(C)(C)OC(=O)N1CCC2(CC2)C[C@H]1CN1C(=O)c2ccccc2C1=O]

To a solution of (S)-5-hydroxymethyl-6-aza-spiro[2.5]octane-6-carboxylic acid tert-butyl ester (intermediate 18, 10 g, 42 mmol) in THF (300 ml) was added triphenyl phosphine (13 g, 50 mmol), phthalimide (6.2 g, 42 mmol) and diethyl azodicarboxylate (21.75 g, 50 mmol) at 0° C. under the protection of nitrogen. After the completion of addition, the reaction mixture was warmed to room temperature, and stirred at room temperature for 10 hours. The resulting mixture was evaporated to obtain crude that was purified by silica gel chromatography (petroleum ether/ethyl acetate from 10/1 to 5/1). (S)-5-(1,3-Dioxo-1,3-dihydro-isoindol-2-ylmethyl)-6-aza-spiro[2.5]octne-6-carboxylic acid tert-butyl ester was obtained as light white solid (13 g, yield:83.6%).

$^1$HNMR (400 MHz, CDCl$_3$) δ ppm 7.73-7.92 (m, 5H), 4.79 (m, 1H), 4.51 (m, 1H), 4.08 (m, 1H), 3.48 (m, 1H), 3.33 (m, 1H), 2.21 (m, 1H), 1.93 (m, 1H), 1.25 (m, 1H), 1.09 (s, 9H), 0.88 (m, 1H), 0.33-0.61 (m, 4H)

Example 21

Preparation of Intermediate 26: (S)-5-aminomethyl-6-aza-spiro[2.5]octane-6-carboxylic acid tert-butyl ester

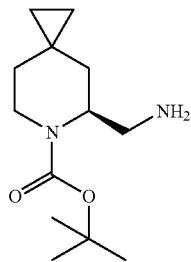 [SMILES: CC(C)(C)OC(=O)N1CCC2(CC2)C[C@H]1CN]

To a solution of (S)-5-(1,3-dioxo-1,3-dihydro-isoindol-2-ylmethyl)-6-aza-spiro[2.5]octne-6-carboxylic acid tert-butyl ester (intermediate 25, 12 g, 32.4 mmol) in ethanol (150 ml) was added hydrazine hydrate (8.1 g, 162 mmol). After the completion of addition, the reaction mixture was stirred at 80° C. for 5 hours. The resulting mixture was filtered, and the filtrate was evaporated to obtain crude that was purified by silica gel chromatography (petroleum ether/ethyl acetate from 10/1 to 1/1). (S)-5-Aminomethyl-6-aza-spiro[2.5]octane-6-carboxylic acid tert-butyl ester was obtained as colorless oil (6.88 g, yield 86%).

$^1$HNMR (400 MHz, CDCl$_3$) δ ppm 4.28 (m, 1H), 4.06 (m, 1H), 3.20 (m, 1H), 2.96 (m, 1H), 1.79 (m, 1H), 2.10 (m, 1H), 1.89 (m, 1H), 1.49 (s, 9H), 0.95 (d, 1H), 0.80 (d, 1H), 0.27-0.44 (m, 4H);

Example 22

Preparation of Intermediates 27-33

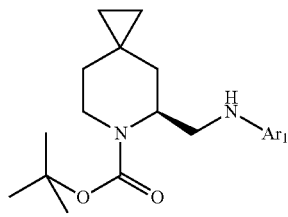

General Procedure 2

To the solution of (S)-5-aminomethyl-6-aza-spiro[2.5]octane-6-carboxylic acid tert-butyl ester (intermediate 26, 2 mmol) in isopropanol (50 ml) and N,N-diisopropylethylamine (3 mmol) was added Ar1-X (where X=2Cl, 2F or 2Br; 1.1 mmol). After the completion of addition, the reaction mixture was stirred until conversion of the staring material and, depending on Ar1-X, in a temperature range −20° to 90° C. The resulting mixture was evaporated to obtain a crude that was purified by silica gel chromatography (petroleum ether/ethyl acetate from 10/1 to 3/1).

According to general procedure 2 the following intermediates were prepared:

| Inter. | Ar1 | Name | X | Temperature (° C.) | Yield |
|---|---|---|---|---|---|
| 27 | | (S)-tert-butyl 5-(((5-methylpyrimidin-2-yl)amino)methyl)-6-azaspiro[2.5]octane-6-carboxylate | Br | 90 | 36 |

| Inter. | Ar1 | Name | X | Temperature (°C.) | Yield |
|---|---|---|---|---|---|
| 28 | | (S)-tert-butyl 5-(((4-methylpyrimidin-2-yl)amino)methyl)-6-azaspiro[2.5]octane-6-carboxylate | Cl | 90 | 54 |
| 29 | | (S)-tert-butyl 5-(((4,6-dimethylpyrimidin-2-yl)amino)methyl)-6-azaspiro[2.5]octane-6-carboxylate | Cl | 90 | 47 |
| 30 | | (S)-tert-butyl 5-(((4,6-difluoropyrimidin-2-yl)amino)methyl)-6-azaspiro[2.5]octane-6-carboxylate | F | −20 then RT | 58 |
| 31 | | (S)-tert-butyl 5-(((6-fluoropyridin-2-yl)amino)methyl)-6-azaspiro[2.5]octane-6-carboxylate | F | 90 | 32 |
| 32 | | (S)-tert-butyl 5-(((5-fluoropyridin-2-yl)amino)methyl)-6-azaspiro[2.5]octane-6-carboxylate | F | 90 | 50 |
| 33 | | (S)-tert-butyl 5-(((5-fluoropyrimidin-2-yl)amino)methyl)-6-azaspiro[2.5]octane-6-carboxylate | Cl | 90 | 50 |

Example 23

Preparation of Intermediates 34-45

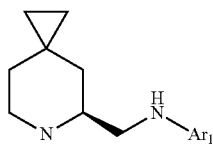

General Procedure 3:

A selection of Intermediates 20-24 and 27-33 (1 eq) were dissolved in dichloromethane (10 ml/mmol) and cooled to 0° C., then trifluoroacetic acid (2 ml/mmol) was added. After 1 hour at 0° C. and 2 hours at room temperature the solution was evaporated, the residue re-dissolved in dichloromethane was washed with saturated NaHCO₃ aqueous solution. The organic layers were dried (Na₂SO₄) and concentrated under vacuum. The crude was purified by silica gel column chromatography (CHCl₃/MeOH=8/2). Intermediates were obtained as light yellow oils.

General Procedure 4:

To the solution of a selection of intermediates 20-24 and 27-33 in ethyl acetate was added HCl(g)/EtOAc (4.0M) at 0° C. After the completion of addition, the reaction mixture was stirred at 0° C. for 1 hour. The resulting solids were collected by filtration, and washed with petroleum ether and dried to give intermediates as hydrochlorides.

According to general procedure 3 or 4 the following intermediates were prepared:

| Intermediate | Name | Procedure | Yield |
|---|---|---|---|
| 34 | (S)-N-(6-azaspiro[2.5]octan-5-ylmethyl)-5-chloropyridin-2-amine | 3 | 98 |
| 35 | (S)-N-(6-azaspiro[2.5]octan-5-ylmethyl)-5-fluoropyridin-2-amine | 4 | 75 |
| 36 | (S)-N-(6-azaspiro[2.5]octan-5-ylmethyl)-5-(trifluoromethyl)pyridin-2-amine | 3 | 90 |
| 37 | (S)-N-(6-azaspiro[2.5]octan-5-ylmethyl)-6-methylpyridin-2-amine | 3 | 70 |
| 38 | (S)-N-(6-azaspiro[2.5]octan-5-ylmethyl)-6-chloropyridin-2-amine | 3 | 87 |
| 39 | (S)-N-(6-azaspiro[2.5]octan-5-ylmethyl)-6-(trifluoromethyl)pyridin-2-amine | 3 | 88 |
| 40 | (S)-N-(6-azaspiro[2.5]octan-5-ylmethyl)-5-methylpyrimidin-2-amine | 4 | 100 |
| 41 | (S)-N-(6-azaspiro[2.5]octan-5-ylmethyl)-4-methylpyrimidin-2-amine | 4 | 60 |
| 42 | (S)-N-(6-azaspiro[2.5]octan-5-ylmethyl)-4,6-dimethylpyrimidin-2-amine | 4 | 90 |
| 43 | (S)-N-(6-azaspiro[2.5]octan-5-ylmethyl)-4,6-difluoropyrimidin-2-amine | 4 | 85 |
| 44 | (S)-N-(6-azaspiro[2.5]octan-5-ylmethyl)-6-fluoropyridin-2-amine | 4 | 85 |
| 45 | (S)-N-(6-azaspiro[2.5]octan-5-ylmethyl)-5-fluoropyrimidin-2-amine | 4 | 56 |

Intermediates 34-45 Characterization:

| Intermediate | Ar1 | Starting intermediate | ¹H-NMR | MS |
|---|---|---|---|---|
| 34 | 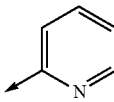 | 20 | ¹HNMR (CDCl₃) δ ppm 7.94 (d, 1H) 7.32 (m, 1H) 6.48 (d, 1H) 6.22 (m, 1H) 3.74 (m. 1H) 3.37-3.50 (m, 3H) 2.95 (m, 1H) 2.25 (m, 1H) 2.08-2.66 (m, 1H) 1.23 (m, 1H) 1.07 (m, 1H) 0.41-0.55 (m, 4H). | ESI+ m/z 254 [M + 1]⁺ |
| 35 | 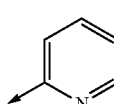 | 32 | ¹HNMR (CDCl₃) δ ppm 9.38 (s, 1H), 9.20 (s, 1H), 8.06 (s, 1H), 7.79 (d, 1H), 7.00 (d, 1H), 3.60 (m, 2H), 3.35 (m, 2H), 2.91 (m, 1H), 2.13 (m, 1H), 1.95 (m, 1H), 1.28 (m, 1H), 1.03 (m, 1H), 0.35-0.46 (m, 4H); | ESI+ m/z 236 [M + 1]⁺ |
| 36 | 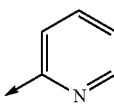 | 21 | — | ESI+ m/z 287 [M + 1]⁺ |
| 37 | 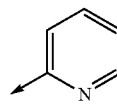 | 22 | ¹HNMR (CDCl₃) δ ppm 7.32 (m, 1H) 6.46 (d, 1H) 6.32 (d, 1H) 5.75 (m, 1H) 3.45-3.65 (m, 4H) 3.05 (m, 1H) 2.42 (s, 3H) 2.06-2.18 (m, 1H) 1.0-1.29 (m, 2H) 0.36-0.52 (m, 4H). | |
| 38 | 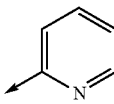 | 23 | ¹HNMR (CDCl₃) δ ppm 7.30-7.34 (m, 1H), 6.56-6.58 (m, 1H), 6.33-6.35 (m, 1H), 5.76 (m, 1H), 3.53-3.58 (m, 1H), 3.41-3.47 (m, 1H), 3.24-3.32 (m, 1H), 2.91-2.98 (m, 1H), 2.06-2.13 (m, 1H), 1.91-1.97 (m, 1H), 1.06-1.09 (m, 1H), 0.95-0.98 (m, 1H), 0.34-0.49 (m, 4H); | ESI+ m/z 252 [M + 1]⁺ |
| 39 | 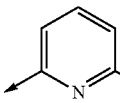 | 24 | ¹HNMR (CDCl₃) δ ppm 7.48-7.52 (m, 1H), 6.92-6.94 (m, 1H), 6.60-6.62 (m, 1H), 5.69 (m, 1H), 3.54-3.59 (m, 1H), 3.37-3.42 (m, 1H), 3.17-3.26 (m, 1H), 2.86-2.69 (m, 1H), 1.99-2.06 (m, 1H), 1.83-1.89 (m, 1H), 1.02-1.06 (m, 1H), 0.92-0.95 (m, 1H), 0.32-0.46 (m, 4H); | ESI+ m/z 287 [M + 1]⁺ |
| 40 | 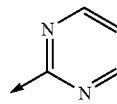 | 27 | ¹HNMR (CDCl₃) δ ppm 9.09 (s, 2H), 8.39 (d, 2H), 8.02 (s, 1H), 3.65 (m, 1H), 3.54 (m, 1H), 3.36 (m, 1H), 3.29 (m, 1H), 2.89 (m, 1H), 2.15 (s, 3H), 1.92 (m, 2H), 1.91 (m, 2H), 1.18 (m, 1H), 1.05 (m, 1H), 0.35-0.45 (m, 4H); | ESI+ m/z 233 [M + 1]⁺ |
| 41 | 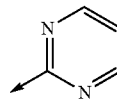 | 28 | ¹HNMR (CDCl₃) δ ppm 9.18 (s, 2H), 8.36 (d, 1H), 6.85 (s, 1H), 3.73 (m, 1H), 3.64 (m, 1H), 3.38 (m, 1H), 3.30 (m, 1H), 2.89 (m, 1H), 2.44 (m, 3H), 2.06 (m, 1H), 1.95 (m, 1H), 1.20 (m, 1H), 1.05 (m, 1H), 0.35-0.47 (m, 4H) | ESI+ m/z 233 [M + 1]⁺ |
| 42 | 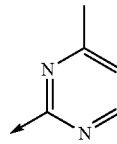 | 29 | ¹HNMR (CDCl₃) δ ppm 9.12-9.23 (m, 2H), 8.24 (s, 1H), 6.81 (s, 1H), 3.81 (m, 1H), 3.65 (m, 1H), 3.32 (m, 1H), 2.91 (m, 1H), 2.43 (m, 1H), 1.92-2.11 (m, 2H), 1.04-1.24 (m, 3H), 0.36-0.48 (m, 4H) | ESI+ m/z 247 [M + 1]⁺ |
| 43 | 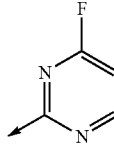 | 30 | ¹HNMR (CDCl₃) δ ppm 8.95 (s, 2H), 8.28 (t, 2H), 6.32 (s, 1H), 329-3.58 (m, 4H), 2.93 (m, 1H), 2.02 (m, 1H), 1.89 (m, 1H), 1.15 (m, 1H), 1.03 (s, 1H), 0.33-0.47 (m, 4H); | ESI+ m/z 255 [M + 1]⁺ |
| 44 | 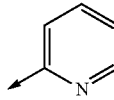 | 31 | ¹HNMR (CDCl₃) δ ppm 9.28 (s, 2H), 7.54 (q, 1H), 7.19 (s, 4H), 6.45 (dd, 1H), 6.16 (dd, 1H), 3.54 (m, 1H), 3.42 (m, 1H), 3.27 (m, 1H), 2.11 (m, 1H), 1.97 (m, 1H), 1.17 (m, 1H), 1.02 (m, 1H), 0.35-0.46 (m, 4H); | ESI+ m/z 236 [M + 1]⁺ |
| 45 | 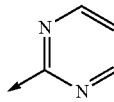 | 33 | ¹HNMR (CDCl₃) δ ppm 9.07 (s, 2H), 8.42 (s, 2H), 7.48 (s, 1H), 3.43-3.60 (m, 2H), 3.29 (m, 2H), 2.89 (m, 1H), 2.08 (m, 1H), 1.89 (m, 1H), 1.01-1.17 (m, 2H), 0.33-0.44 (m, 4H); | ESI+ m/z 237 [M + 1]⁺ |

Example 24

Preparation of Intermediates 46-50

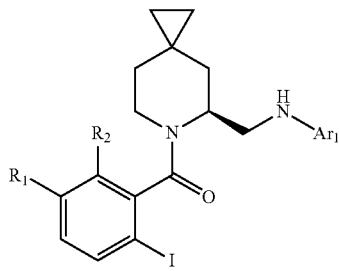

General Procedure 5

Intermediates 34-45 (1 eq) were dissolved in dry dichloromethane (10 ml/mmol) at 0° C. with TEA (3 eq), the corresponding 2-Iodo benzoyl chloride dissolved in dry dichloromethane was added. After 2 hours the mixture was poured in aqueous $NaHCO_3$ and extracted with dichloromethane. The organic layers were combined, dried ($Na_2SO_4$) and concentrated under vacuum; crude product was purified by silica gel column chromatography (Hexane/AcOEt 9/1).

According to general procedure 5 the following intermediates were prepared:

| Intermediate | Name | Yield |
|---|---|---|
| 46 | (S)-(5-(((5-chloropyridin-2-yl)amino)methyl)-6-azaspiro[2.5]octan-6-yl)(2-iodophenyl)methanone | 98 |
| 47 | (S)-(5-(((6-chloropyridin-2-yl)amino)methyl)-6-azaspiro[2.5]octan-6-yl)(2-iodo-5-methylphenyl)methanone | 98 |
| 48 | (S)-(2-iodo-5-methylphenyl)(5-(((6-(trifluoromethyl)pyridin-2-yl)amino)methyl)-6-azaspiro[2.5]octan-6-yl)methanone | 93 |
| 49 | (S)-(5-(((5-chloropyridin-2-yl)amino)methyl)-6-azaspiro[2.5]octan-6-yl)(5-fluoro-2-iodophenyl)methanone | 98 |
| 50 | (S)-(5-(((5-chloropyridin-2-yl)amino)methyl)-6-azaspiro[2.5]octan-6-yl)(2-fluoro-6-iodophenyl)methanone | 98 |

Intermediates 46-50 Characterization:

| Int. | Ar1 | R1 | R2 | Starting intermediate | $^1$H-NMR | MS |
|---|---|---|---|---|---|---|
| 46 | 5-Cl-pyridin-2-yl | H | H | 34 | — | ESI+ m/z 482 [M + 1]$^+$ |
| 47 | 6-Cl-pyridin-2-yl | Me | H | 38 | $^1$HNMR (CDCl$_3$) δ ppm 7.62-7.70 (m, 1H), 7.21-7.40 (m, 2H), 6.81-7.06 (m, 1H), 6.51-6.62 (m, 1H), 6.28-6.43 (m, 1H), 5.16-5.26 (m, 1H), 4.47-5.01 (m, 1H), 3.63-4.07 (m, 2H), 3.42-3.56 (m, 1H), 3.02-3.35 (m, 1H), 2.21-2.37 (m, 4H), 1.83-2.07 (m, 1H), 1.09-1.28 (m, 1H), 0.78-0.98 (m, 1H), 052-0.63 (m, 2H), 0.31-0.41 (m, 2H) | ESI+ m/z 496 [M + 1]$^+$ |
| 48 | 6-CF$_3$-pyridin-2-yl | Me | H | 39 | $^1$HNMR (CDCl$_3$) δ ppm 7.65-7.70 (m, 1H), 7.45-7.55 (m, 1H), 6.55-7.08 (m, 3H), 6.65-6.35 (m, 1H), 4.75-5.38 (m, 2H), 3.65-4.20 (m, 2H), 3.43-3.58 (m, 1H), 3.08-3.35 (m, 1H), 2.15-2.35 (m, 4H), 1.80-2.0 (m, 1H), 1.05-1.25 (m, 1H), 0.75-1.0 (m, 1H), 0.50-0.65 (m, 2H), 0.30-0.42 (m, 2H) | ESI+ m/z 530 [M + 1]$^+$ |
| 49 | 5-Cl-pyridin-2-yl | F | H | 34 | $^1$HNMR (CDCl$_3$) δ ppm 8.04-8.06 (m, 1H), 7.69-7.85 (m, 1H), 7.32-7.41 (m, 1H), 6.70-7.01 (m, 2H), 6.23-6.47 (m, 1H), 5.19 (m, 1H), 4.41-4.93 (m, 1H), 3.79-4.12 (m, 2H), 3.03-3.65 (m, 3H), 2.23-2.38 (m, 4H), 1.85-1.92 (m, 1H), 1.07-1.28 (m, 1H), 0.80-1.02 (m, 1H), 0.34-0.61 (m, 4H) | ESI+ m/z 500 [M + 1]$^+$ |
| 50 | 5-Cl-pyridin-2-yl | H | F | 34 | $^1$HNMR (CDCl$_3$) δ ppm 7.70-8.04 (m, 1H), 7.59-7.67 (m, 1H), 7.30-7.36 (m, 1H), 6.86-7.16 (m, 2H), 6.28-6.49 (m, 1H), 5.16-5.29 (m, 1H), 4.59-4.97 (m, 1H), 3.70-4.14 (m, 1H), 3.30-3.61 (m, 2H), 2.29-3.09 (m, 2H), 1.99-2.30 (m, 2H), 1.18-1.32 (m, 1H), 0.85-1.05 (m, 1H), 0.33-061 (m, 4H) | ESI+ m/z 500 [M + 1]$^+$ |

Example 25

Preparation of Intermediate 52: (2S,4R)-4-(tert-butyl-dimethyl-silanyloxy)-pyrrolidine-1,2-dicarboxylic acid 1-tert-butyl ester 2-methyl ester

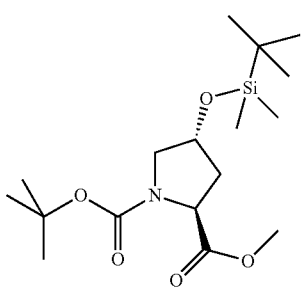 [SMILES: COC(=O)[C@@H]1C[C@@H](O[Si](C)(C)C(C)(C)C)CN1C(=O)OC(C)(C)C]

Imidazole (21.7 g, 320 mmol) and tert-butyldimethylsilyl chloride (26.2 g, 170 mol) were added to a solution of (2S,4R)-4-hydroxy-pyrrolidine-1,2-dicarboxylic acid 1-tert-butyl ester 2-methyl ester (intermediate 51, 38.7 g, 160 mmol) in dichloromethane (700 ml) at 0° C., the mixture was maintained under stirring at room temperature for 4 hours. The mixture was filtered, the liquid phase was then washed with HCl 0.5N (500 ml), saturated NaHCO₃ aqueous (500 ml) then brine (2×500 ml). The organic solvent was dried (Na$_2$SO$_4$) and evaporated to give 58 g of intermediate 52 (yellow solid, yield: 100%).

¹HNMR (400 MHz, CDCl3) δ ppm 4.34-4.46 (m, 2H), 3.75 (m, 3H), 3.58-3.65 (m, 1H), 3.32-3.44 (m, 1H), 2.20 (m, 1H), 2.04 (m, 1H), 1.48-1.43 (d, 9H), 0.92 (s, 9H), 0.05 (s, 6H).

Example 26

Preparation of Intermediate 53: (2S,4R)-4-(tert-butyl-dimethyl-silanyloxy)-2-hydroxymethyl-pyrrolidine-1-carboxylic acid tert-butyl ester

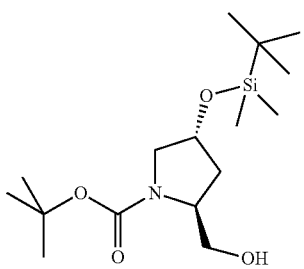 [SMILES: CC(C)(C)OC(=O)N1C[C@H](O[Si](C)(C)C(C)(C)C)C[C@H]1CO]

To a suspended solution of lithium aluminium hydride (7.2 g, 190 mmol) in THF (200 ml) under nitrogen (2S,4R)-4-(tert-Butyl-dimethyl-silanyloxy)-pyrrolidine-1,2-dicarboxylic acid 1-tert-butyl ester 2-methyl ester (intermediate 52, 58 g, 160 mmol) in THF (300 ml) was added dropwise at 0° C. The solution was maintained under stirring at 0° C. for 2 hours, then Na$_2$SO$_4$.10H$_2$O was added and the mixture was filtered, the filtrate was concentrated to give 51.4 g of intermediate 53 (yellow oil, yield: 96%).

¹HNMR (400 MHz, CDCl₃) δ ppm 4.95 (m, 1H), 4.30 (m, 1H), 4.15 (m, 1H), 3.71 (m, 1H), 3.57 (m, 1H), 3.45 (m, 1H), 3.36 (m, 1H), 1.98 (m, 1H), 1.49 (s, 9H), 0.89 (s, 9H), 0.06 (s, 6H)

Example 27

Preparation of Intermediate 54: (2S,4R)-4-(tert-butyl-dimethyl-silanyloxy)-2-(4-nitro-benzoyloxymethyl)-pyrrolidine-1-carboxylic acid tert-butyl ester

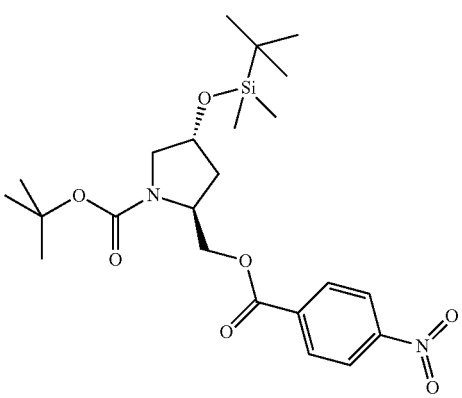 [SMILES: CC(C)(C)OC(=O)N1C[C@H](O[Si](C)(C)C(C)(C)C)C[C@H]1COC(=O)c1ccc([N+](=O)[O-])cc1]

(2S,4R)-4-(Tert-butyl-dimethyl-silanyloxy)-2-hydroxymethyl-pyrrolidine-1-carboxylic acid tert-butyl ester (intermediate 53, 51.4 g, 155 mmol) dissolved in 500 ml of dichloromethane was cooled to 0° C., then p-nitrobenzoic acid (28.5 g, 171 mmol), N,N'-dicyclohexylcarbodiimide (35.2 g, 171 mmol) and 4-dimethylaminopyridine (1.90 g, 1.60 mmol) were added. The mixture was maintained under stirring at room temperature for 18 hours, then filtrated; the filtrate was concentrated to obtain crude that was purified by silica gel chromatography (petroleum ether/ethyl acetate from 15/1 to 10/1). (2S,4R)-4-(tert-Butyl-dimethyl-silanyloxy)-2-(4-nitro-benzoyloxymethyl)-pyrrolidine-1-carboxylic acid tert-butyl ester was obtained as white solid (70 g, yield: 94%).

¹HNMR (400 MHz, CDCl₃) δ ppm 8.32 (d, 2H), 8.23 (d, 2H), 4.44-4.56 (m, 4H), 3.42-3.58 (m, 2H), 2.08 (m, 1H), 1.96 (m, 1H), 1.48 (s, 9H), 0.89 (s, 9H), 0.08 (s, 6H)

Example 28

Preparation of Intermediate 55: (2S,4R)-4-hydroxy-2-(4-nitro-benzoyl oxymethyl)-pyrrolidine-1-carboxylic acid tert-butyl ester

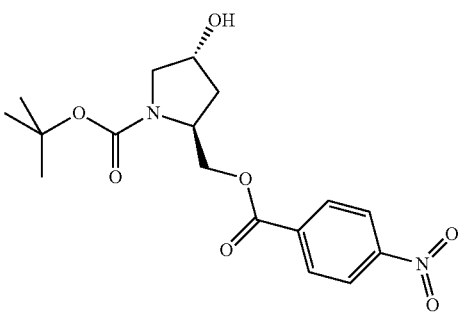 [SMILES: CC(C)(C)OC(=O)N1C[C@H](O)C[C@H]1COC(=O)c1ccc([N+](=O)[O-])cc1]

To the solution of (2S,4R)-4-(tert-Butyl-dimethyl-silanyloxy)-2-(4-nitro-benzoyl oxymethyl)-pyrrolidine-1-carboxylic acid tert-butyl ester (intermediate 54, 35 g, 72.9 mmol) in 300 ml of pyridine was added 70% pyridine hydrofluoride (200 ml) dropwise at 0° C. After 2 hours at room temperature, then temperature was cooled to 0° C. and 1500 ml of water was added, then reaction was allowed to reach room temperature. Reaction was extracted with ethyl acetate (2×1.5 L), the organic solvent was washed with 1N HCl (2.0 L), saturated NaHCO₃ aqueous (2.0 L) and brine (2.0 L), dried (Na₂SO₄) and evaporated to give 23 g of intermediate 55 (yellow solid, yield: 92%).

¹HNMR (400 MHz, CDCl₃) δ ppm 8.32 (d, 2H), 8.20 (d, 2H), 4.34-4.59 (m, 4H), 3.48-3.70 (m, 2H), 1.99-2.20 (m, 3H), 1.46 (s, 9H)

Example 29

Preparation of Intermediate 56: (S)-2-(4-nitro-benzoyloxymethyl)-4-oxo-pyrrolidine-1-carboxylic acid tert-butyl ester

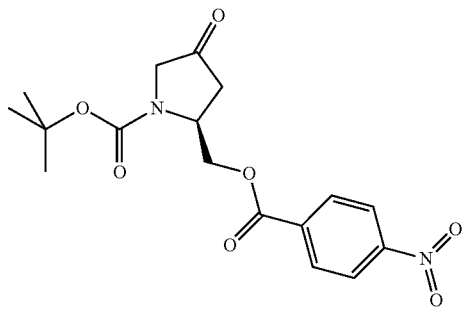 [SMILES: CC(C)(C)OC(=O)N1CC(=O)C[C@H]1COC(=O)c1ccc([N+](=O)[O-])cc1]

To a solution of oxalyl chloride (23.5 ml, 246 mmol) in dichloromethane (400 ml), which was cooled to −75° C., dimethyl sulfoxide (35 ml, 492 mmol) in dichloromethane (60 ml) was added in 20 minutes. After 30 minutes at −70° C., a solution of (2S,4R)-4-hydroxy-2-(4-nitro-benzoyloxymethyl)-pyrrolidine-1-carboxylic acid tert-butyl ester (intermediate 55, 45 g, 123 mmol) in dichloromethane (300 ml) was added dropwise. After 2 hours at −70° C., N,N-diisopropylethylamine (60 ml) was added in 10 minutes. After 25 minutes at −60° C. and 30 minutes at room temperature dichloromethane (200 ml) was added. The organic solvent was washed with 0.5N HCl (500 ml), water (500 ml) and brine (500 ml), dried (Na₂SO₄) and evaporated to obtain a crude that was purified by silica gel chromatography (petroleum ether/ethyl acetate from 5/1 to 3/1). (S)-2-(4-Nitro-benzoyloxymethyl)-4-oxo-pyrrolidine-1-carboxylic acid tert-butyl ester was obtained as white solid (28.5 g, yield: 70%.

¹HNMR (400 MHz, CDCl₃) δ ppm 8.32 (d, 2H), 8.12 (d, 2H), 4.69-4.84 (m, 2H), 4.38 (m, 1H), 4.01 (m, 1H), 3.71 (m, 1H), 2.94 (m, 1H), 2.56 (m, 1H), 1.51 (s, 9H)

Example 30

Preparation of Intermediate 57: (S)-4-methylene-2-(4-nitro-benzoyloxymethyl)-pyrrolidine-1-carboxylic acid tert-butyl ester

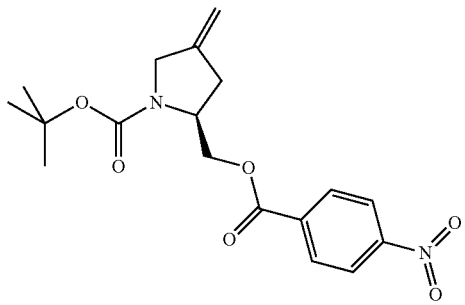 [SMILES: C=C1C[C@@H](COC(=O)c2ccc([N+](=O)[O-])cc2)N(C(=O)OC(C)(C)C)C1]

Methytriphenylphosphonium bromide (38 g, 106 mmol) dissolved in 300 ml of toluene was cooled to 0° C., then added sodium hexamethyldisilazide (48.3 ml, 93.7 mmol) was added dropwise. After 2 hours at room temperature, The temperature was cooled to 0° C., a solution of (S)-2-(4-nitrobenzoyloxymethyl)-4-oxo-pyrrolidine-1-carboxylic acid tert-butyl ester (intermediate 56, 15.5 g, 42.6 mmol) in 300 ml of toluene was added. After 10 minutes 500 ml of water was slowly added, then reaction was allowed to reach room temperature. The organic solvent was washed with brine (500 ml), dried (Na₂SO₄) and evaporated to obtain crude that was purified by silica gel chromatography (petroleum ether/ethyl acetate from 15/7 to 7/1). (S)-4-Methylene-2-(4-nitro-benzoyloxymethyl)-pyrrolidine-1-carboxylic acid tert-butyl ester was obtained as yellow solid (6.82 g, yield 46%).

¹HNMR (400 MHz, CDCl₃) δ ppm 8.29 (d, 2H), 8.23 (d, 2H), 5.07 (s, 2H), 4.35-4.50 (m, 3H), 4.16 (m, 1H), 3.93 (m, 1H), 2.89 (m, 1H), 2.52 (m, 1H), 1.48 (s, 9H)

Example 31

Preparation of Intermediate 58: (S)-6-(4-nitro-benzoyloxymethyl)-5-aza-spiro[2.4]heptane-5-carboxylic acid tert-butyl ester

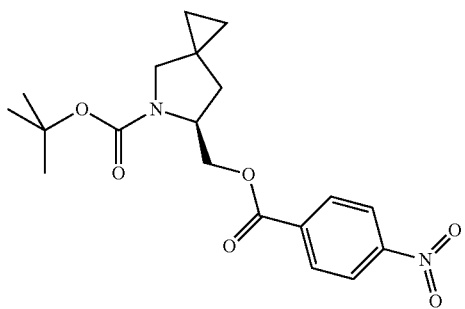 [SMILES: CC(C)(C)OC(=O)N1CC2(CC2)C[C@H]1COC(=O)c1ccc([N+](=O)[O-])cc1]

Methyl-3-nitro-1-nitroxoguanide (90 g) was added slowly to a solution of KOH (66 g) in water (130 ml) and Et₂O (250 ml) at 0° C. After 30 minutes at 0° C., the organic phase was separated to get the solution of diazomethane.

(S)-4-Methylene-2-(4-nitro-benzoyloxymethyl)-pyrrolidine-1-carboxylic acid tert-butyl ester (intermediate 57, 11.3 g, 31.2 mmol) was dissolved in 120 ml of THF was added palladiumdiacetate (3.0 g). After 2 hours at room temperature, the temperature was cooled to −60° C.; the solution of diazomethane was added slowly. The mixture was maintained under stirring at −60° C. to 0° C. for 3 hours and warmed to room temperature overnight. The mixture was filtrated, than the liquid phase was concentrated to give 9.0 g of intermediate 58 (yellow oil, yield: 79%).

$^1$HNMR (400 MHz, CDCl$_3$) δ ppm 8.30 (d, 2H), 8.25 (d, 2H), 4.30-4.60 (m, 3H), 3.55 (m, 1H), 3.11 (m, 1H), 2.29 (m, 1H), 1.47 (s, 9H), 0.88 (m, 1H), 0.66 (m, 4H)

Example 32

Preparation of Intermediate 59: (S)-6-hydroxymethyl-5-aza-spiro[2.4]heptane-5-carboxylic acid tert-butyl ester

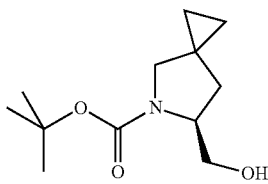 [SMILES: CC(C)(C)OC(=O)N1CC2(CC2)C[C@H]1CO]

(S)-6-(4-Nitro-benzoyloxymethyl)-5-aza-spiro[2.4]heptane-5-carboxylic acid tert-butyl ester (intermediate 58, 8.9 g, 23.7 mmol) dissolved in 200 ml of methanol was cooled to 0° C., then 2N NaOH aqueous (100 ml) was added. The mixture was maintained under stirring at room temperature for 1 hour, and then concentrated. Ethyl acetate (200 ml) was added and the organic solvent was washed with water (200 ml) and brine (200 ml), dried (Na$_2$SO$_4$) and evaporated to obtain a crude that was purified by silica gel chromatography (petroleum ether/ethyl acetate 5/1) to give 5.0 g of crude product, then purified by preparative HPLC to give 3.25 g of intermediate 59 (colorless oil, yield: 62%).

$^1$HNMR (400 MHz, CDCl$_3$) δ ppm 4.73 (m, 1H), 3.78 (m, 1H), 3.55 (m, 1H), 3.33 (m, 1H), 2.95 (m, 1H), 2.11 (m, 1H), 1.64 (m, 1H), 1.40 (s, 9H), 0.53 (m, 4H);

MS Calcd.: 227; MS Found: 228 ([M+1]$^+$).

Example 33

Preparation of Intermediate 60: (S)-tert-butyl 6-formyl-5-azaspiro[2.4]heptane-5-carboxylate

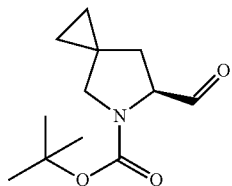 [SMILES: CC(C)(C)OC(=O)N1CC2(CC2)C[C@H]1C=O]

To (S)-tert-butyl 6-(hydroxymethyl)-5-azaspiro[2.4]heptane-5-carboxylate (Intermediate 59, 2.2 g, 9.7 mmol) dissolved in 10 ml of DCM, TEMPO (306 mg, 1.9 mmol) and BAIB (3.43 mg, 10.6 mmol) were added. After 2 hours at 25° C., the reaction is diluted with DCM (150 ml), washed with an aqueous solution of Na$_2$S$_2$O$_3$ then with water, dried (Na$_2$SO$_4$) and evaporated to obtain a crude that was purified by silica gel chromatography (petroleum ether to petroleum ether/ethylacetate 95/5). (S)-tert-butyl 6-formyl-5-azaspiro[2.4]heptane-5-carboxylate was obtained as light yellow solid (1.8 g).

$^1$HNMR (DMSO-d6) δ ppm 9.52 (s, 1H) 4.21 (m, 1H) 3.20-3.40 (m, 2H) 2.11 (m, 1H) 1.50-1.80 (m, 1H) 1.36-1.41 (m, 9H) 0.50-0.65 (m, 4H)

Example 34

Preparation of Intermediate 61: (S)-tert-butyl 6-(((5-chloropyridin-2-yl)amino)methyl)-5-azaspiro[2.4]heptane-5-carboxylate

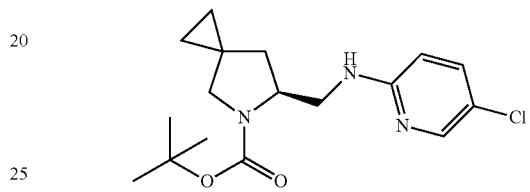

(S)-tert-butyl 6-formyl-5-azaspiro[2.4]heptane-5-carboxylate (Intermediate 60, 700 mg, 3.1 mmol) was dissolved in dichloroethane (15 ml), then acetic acid (0.9 ml, 15.5 mmol) and 5-chloro pyridine (400 mg, 3.1 mmol) were added. After 2 hours at room temperature NaBH(OAc)$_3$ (1.05 g, 4.97 mmol) was added and the reaction was maintained under stirring at room temperature for 18 hours. The reaction was poured in aqueous NaHCO$_3$ and extracted with DCM. The organic layers were combined, dried (Na$_2$SO$_4$) and concentrated under vacuum; crude product was purified by silica gel column chromatography using Petroleum ether/Ethyl acetate=95/5 to 85/15. (S)-tert-butyl 6-(((5-chloropyridin-2-yl)amino)methyl)-5-azaspiro[2.4]heptane-5-carboxylate was obtained as colourless oil (600 mg). MS (ESI) m/z: 338 [M+H]$^+$ Example 35

Preparation of Intermediate 62: (S)-tert-butyl 6-(((6-methylpyridin-2-yl)amino)methyl)-5-azaspiro[2.4]heptane-5-carboxylate

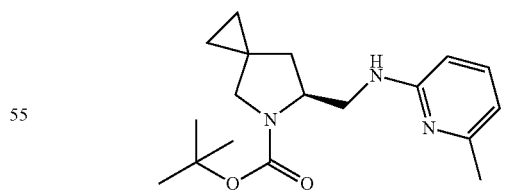

(S)-tert-butyl 6-formyl-5-azaspiro[2.4]heptane-5-carboxylate (Intermediate 60, 700 mg, 3.1 mmol) was dissolved in dichloroethane (15 ml), then acetic acid (0.9 ml, 15.5 mmol) and 6-methyl pyridine (336 mg, 3.1 mmol) were added. After 2 hours at room temperature NaBH(OAc)$_3$ (1.05 g, 4.97 mmol) was added and the reaction was maintained under stirring at room temperature for 18 hours. The reaction was poured in aqueous NaHCO$_3$ and extracted with DCM.

The organic layers were combined, dried (Na₂SO₄) and concentrated under vacuum; crude product was purified by silica gel column chromatography using Petroleum ether/Ethyl acetate=95/5 to 85/15. (S)-tert-butyl 6-(((6-methylpyridin-2-yl)amino)methyl)-5-azaspiro[2.4]heptane-5-carboxylate was obtained as colourless oil (600 mg).

Example 36

Preparation of Intermediate 63: (S)—N-(5-azaspiro [2.4]heptan-6-ylmethyl)-5-chloropyridin-2-amine

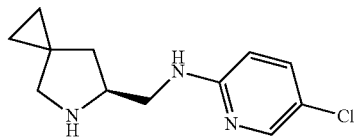 [SMILES: Clc1ccc(NC[C@@H]2CC3(CC3)CN2)nc1]

(S)-tert-butyl6-(((5-chloropyridin-2-yl)amino)methyl)-5-azaspiro[2.4]heptane-5-carboxylate Intermediate 60, 600 mg, 1.77 mmol) was dissolved in dichloromethane (10 ml) and cooled to 0° C., then trifluoroacetic acid (4 ml) was added. After 1 hour at 0° C. and 3 hours at room temperature the solution was evaporated, the residue re-dissolved in dichloromethane was washed with saturated NaHCO₃ aqueous solution. The organic layers were dried (Na₂SO₄) and concentrated under vacuum. The crude was purified by silica gel column chromatography (CHCl₃/MeOH=8/2). (S)—N-(5-azaspiro[2.4]heptan-6-ylmethyl)-5-chloropyridin-2-amine was obtained as light yellow oil (400 mg).

MS (ESI) m/z: 238 [M+H]⁺

¹HNMR (CDCl₃) δ ppm 8.02 (d, J=3 Hz, 1H) 7.35 (dd, J=8 Hz, 3 Hz, 1H) 6.39 (d, J=8 Hz, 1H) 5.05 (m, 1H) 3.60-3.63 (m, 1H) 3.40-3.48 (m, 1H) 3.20-3.30 (m, 1H) 2.85-2.90 (m, 1H) 1.85-1.95 (m, 1H) 1.52-1.61 (m, 1H) 0.50-0.60 (m, 4H)

Example 37

Preparation of Intermediate 64: (S)—N-(5-azaspiro [2.4]heptan-6-ylmethyl)-6-methylpyridin-2-amine

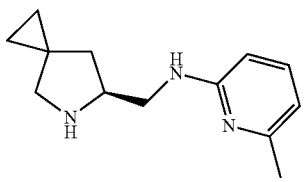 [SMILES: Cc1cccc(NC[C@@H]2CC3(CC3)CN2)n1]

S)-tert-butyl 6-(((6-methylpyridin-2-yl)amino)methyl)-5-azaspiro[2.4]heptane-5-carboxylate (Intermediate 60, 600 mg, 1.89 mmol) was dissolved in dichloromethane (10 ml) and cooled to 0° C., then trifluoroacetic acid (4 ml) was added. After 1 hour at 0° C. and 3 hours at room temperature the solution was evaporated, the residue re-dissolved in dichloromethane was washed with saturated NaHCO₃ aqueous solution. The organic layers were dried (Na₂SO₄) and concentrated under vacuum. The crude was purified by silica gel column chromatography (CHCl₃/ MeOH=8/2). (S)—N-(5-azaspiro[2.4]heptan-6-ylmethyl)-6-methylpyridin-2-amine was obtained as light yellow oil (225 mg).

MS (ESI) m/z: 218 [M+H]⁺

¹HNMR (CDCl₃) δ ppm 7.37-7.41 (m, 1H) 6.55 (d, J=8 Hz, 1H) 6.45 (d, J=8 Hz, 1H) 5.62 (s, 1H) 4.25-4.31 (m, 1H) 3.76-3.80 (m, 1H) 3.60-3.66 (m, 1H) 3.28 (d, J=12 Hz, 1H) 3.07 (d, J=12 Hz, 1H) 1.89-2.01 (m, 2H) 0.59-0.81 (m, 4H)

Example 38

Preparation of Intermediate 65: (S)-tert-butyl 6-((1, 3-dioxoisoindolin-2-yl)methyl)-5-azaspiro[2.4]heptane-5-carboxylate

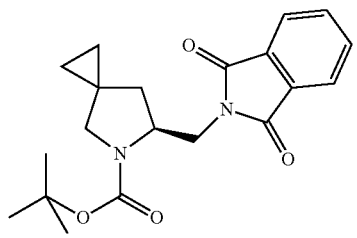 [SMILES: CC(C)(C)OC(=O)N1CC2(CC2)C[C@H]1CN1C(=O)c2ccccc2C1=O]

In a round bottomed flask under nitrogen atmosphere triphenylphosphine (947 mg, 3.61 mmol) and phthalimide (541 mg, 3.67 mmol) were added to a solution of (S)-tert-butyl 6-(hydroxymethyl)-5-azaspiro[2.4]heptane-5-carboxylate (Intermediate 59, 498 mg, 2.19 mmol) in 10 ml of dry THF. The mixture was cooled with an ice bath and a solution of DEAD 40% wt in toluene was dropwise added (1.6 ml, 3.51 mmol).

The reaction was allowed to warm up to room temperature overnight. The next morning the mixture was quenched with a small amount of MeOH; the solvent was then removed and the obtained residue was purified by flash chromatography on a 50 g silica cartridge, eluting with a step gradient: cyclohexane 100% in 2 column volumes, cyclohexane/AcOEt 95/5 in 2 column volumes, linear gradient up to 85/15 in 10 column volumes and then isocratic 85/15 in 4 column volumes.

The collected fractions were then evaporated to give 758 mg of (S)-tert-butyl 6-((1,3-dioxoisoindolin-2-yl)methyl)-5-azaspiro[2.4]heptane-5-carboxylate as a clear oil (yield 97%).

MS (ESI) m/z 357 [M+H]⁺; 379 [M+Na]⁺

¹HNMR (CDCl₃) δ ppm 7.83-7.91 (m, 2H) 7.69-7.78 (m, 1H) 4.29-4.52 (m, 1H) 4.0-4.13 (m, 1H) 3.77-3.87 (m, 1H) 3.46-3.61 (m, 1H) 3.09 (m, 1H) 2.21-2.31 (m, 1H) 1.26-1.40 (m, 9H) 0.55-0.89 (m, 4H)

Example 39

Preparation of Intermediate 66: (S)-tert-butyl 6-(aminomethyl)-5-azaspiro[2.4]heptane-5-carboxylate

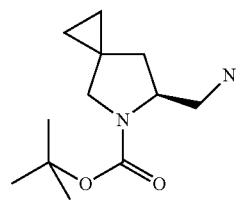 [SMILES: CC(C)(C)OC(=O)N1CC2(CC2)C[C@H]1CN]

(S)-tert-butyl 6-((1,3-dioxoisoindolin-2-yl)methyl)-5-azaspiro[2.4]heptane-5-carboxylate (Intermediate 65, 752 mg, 2.11 mmol) was dissolved in 20 ml of ethanol. Hydrazine monohydrate (550 ul, 11.32 mmol) was added and the mixture was stirred at room temperature overnight.

Copious amount of a white precipitate formed, which was filtered and washed thoroughly with diethyl ether. The liquid phase was evaporated to dryness and the residue was taken up again in diethyl ether. The resulting suspension was then filtered again, further washing all the solids with ether. All the collected liquid phases were evaporated to give 420 mg of (S)-tert-butyl 6-(aminomethyl)-5-azaspiro[2.4]heptane-5-carboxylate as a clear viscous oil (yield 88%).

MS (ESI) m/z 227 [M+H]$^+$; 249 [M+Na]$^+$ $^1$HNMR (CDCl$_3$) δ ppm 4.38-4.26 (m, 1H) 3.42-3.66 (m, 1H) 2.87-3.09 (m, 3H) 2.14-2.19 (m, 1H) 1.48 (s, 9H) 1.24-1.32 (m, 1H) 0.58-0.75 (m, 4H)

Example 40

Preparation of Intermediate 67: (S)-tert-butyl 6-(((4,6-dimethylpyrimidin-2-yl)amino)methyl)-5-azaspiro[2.4]heptane-5-carboxylate

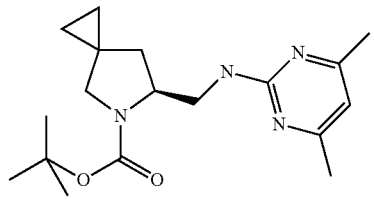 [SMILES: Cc1cc(C)nc(NC[C@@H]2CC3(CC3)CN2C(=O)OC(C)(C)C)n1]

In a microwave vial (S)-tert-butyl 6-(aminomethyl)-5-azaspiro[2.4]heptane-5-carboxylate (Intermediate 66, 61 mg, 0.27 mmol) and 2-chloro-4,6-dimethylpyrimidine (61 mg, 0.43 mmol) were dissolved in 1 ml of isopropyl alcohol. DIPEA (0.1 ml, 0.57 mmol) was added and the vial was sealed and heated to 120° C. in two cycles of 30 minutes each by microwave irradiation.

The solvent was then removed and the residue purified by flash chromatography on a 10 g silica cartridge, eluting with a step gradient: cyclohexane/AcOEt in 2 column volumes, then linear gradient to 65/35 in 16 column volumes and finally isocratic 65/35 in 3 column volumes.

Removal of the solvent yielded 37 mg of (S)-tert-butyl 6-(((4,6-dimethylpyrimidin-2-yl)amino)methyl)-5-azaspiro[2.4]heptane-5-carboxylate as a clear crust (yield 41%).

MS (ESI) m/z 333 [M+H]$^+$; 355 [M+Na]$^+$ $^1$HNMR (CDCl$_3$) δ ppm 6.30-6.32 (m, 1H) 5.37-5.72 (m, 1H) 4.11-4.20 (m, 1H) 3.60-3.85 (m, 2H) 3.44-3.58 (m, 1H) 3.09-3.12 (m, 1H) 2.30 (s, 6H) 2.14-2.20 (m, 1H) 1.50 (s, 9H) 0.85-0.95 (m, 1H) 0.50-0.76 (m, 4H)

Example 41

Preparation of Intermediate 68: (S)-tert-butyl 6-(((5-chloropyrimidin-2-yl)amino)methyl)-5-azaspiro[2.4]heptane-5-carboxylate

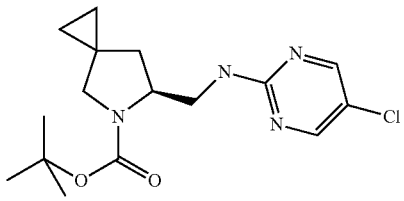 [SMILES: CC(C)(C)OC(=O)N1CC2(CC2)C[C@H]1CNc1ncc(Cl)cn1]

In a microwave vial (S)-tert-butyl 6-(aminomethyl)-5-azaspiro[2.4]heptane-5-carboxylate (Intermediate 66, 66 mg, 0.29 mmol) and 2,5-dichloropyrimidine (65 mg, 0.44) were dissolved in 1 ml of isopropyl alcohol. DIPEA (100 ul, 0.58 mmol) was added; the vial was sealed and heated to 120° C. for 20 minutes by microwave irradiation.

The solvent was then removed and the residue purified by flash chromatography on a 10 g silica cartridge, eluting with a step gradient: cyclohexane/AcOEt in 2 column volumes, then linear gradient to 80/20 in 10 column volumes and finally isocratic 80/20 in 2 column volumes.

Removal of the solvent yielded 60 mg of (S)-tert-butyl 6-(((5-chloropyrimidin-2-yl)amino)methyl)-5-azaspiro[2.4]heptane-5-carboxylate as a white solid (yield 61%).

MS (ESI) m/z 339-341 (Cl pattern) [M+H]$^+$; 361-363 [M+Na]$^+$ $^1$HNMR (CDCl$_3$) δ ppm 8.21 (s, 2H) 5.62-6.5 (m, 1H) 4.20-4.30 (m, 1H) 3.53-3.62 (m, 2H) 3.07-3.49 (m, 2H) 2.24-2.29 (m, 1H) 1.61 (m, 1H) 1.49 (m, 9H) 0.56-0.70 (m, 4H)

Example 42

Preparation of Intermediate 69: (S)—N-(5-azaspiro[2.4]heptan-6-ylmethyl)-4,6-dimethylpyrimidin-2-amine

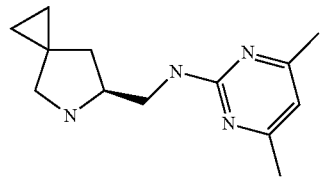 [SMILES: Cc1cc(C)nc(NC[C@@H]2CC3(CC3)CN2)n1]

(S)-tert-butyl 6-(((4,6-dimethyl pyrimidin-2-yl)amino)methyl)-5-azaspiro[2.4]heptane-5-carboxylate (Intermediate 68, 18 mg, 0.054 mmol) was dissolved in 0:5 ml of dry DCM under nitrogen atmosphere. TFA (0.2 ml) was added and the solution shaken at room temperature for 2 hours.

The reaction mixture was loaded on a 1 g SCX cartridge, which was then washed with MeOH, followed by a solution of ammonia 2.0 M in MeOH. The basic fractions were collected and evaporated to give 9 mg of (S)—N-(5-azaspiro[2.4]heptan-6-ylmethyl)-4,6-dimethylpyrimidin-2-amine as a colourless residue (yield 71%).

MS (ESI) m/z 233 [M+H]+

¹HNMR (CDCl₃) δ ppm 6.32 (s, 1H) 5.36 (m, 1H) 3.61-3.67 (m, 2H) 3.41-3.47 (m, 1H) 2.89 (m, 2H) 2.30 (s, 6H) 1.83-1.87 (m, 1H) 1.61-1.65 (m, 1H) 0.52-0.63 (m, 4H)

Example 43

Preparation of Intermediate 70: (S)—N-(5-azaspiro[2.4]heptan-6-ylmethyl)-5-chloropyrimidin-2-amine

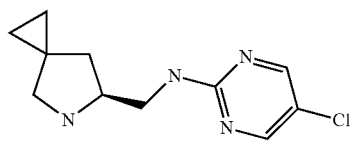 [SMILES: Clc1cnc(NC[C@@H]2CC3(CC3)CN2)nc1]

(S)-tert-butyl 6-(((5-chloropyrimidin-2-yl)amino)methyl)-5-azaspiro[2.4]heptane-5-carboxylate (Intermediate 68, 59 mg, 0.17 mmol) was dissolved in 1 ml of dry DCM under nitrogen atmosphere. TFA (0.3 ml) was added and the solution shaken at room temperature for 40 minutes.

The reaction mixture was diluted in a small amount of MeOH and loaded on a 1 g SCX cartridge, which was then washed with MeOH, followed by a solution of ammonia 2.0 M in MeOH. The basic fractions were collected and evaporated to give 37 mg of (S)—N-(5-azaspiro[2.4]heptan-6-ylmethyl)-5-chloropyrimidin-2-amine as a white solid (yield 91%).

MS (ESI) m/z 239-241 (Cl pattern) [M+H]+

¹HNMR (CDCl₃) δ ppm 8.22 (s, 2H) 5.74 (m, 1H) 3.55-3.67 (m, 2H) 3.35-3.41 (m, 1H) 2.86-2.92 (m, 2H) 1.84-1.89 (m, 1H) 1.56-1.61 (m, 1H) 0.45-0.70 (m, 4H).

Example 44

Preparation of Intermediate 71: tert-butyl 8-azaspiro[4.5]decane-8-carboxylate

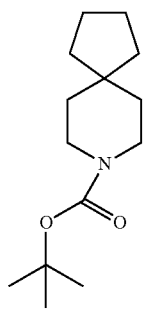 [SMILES: CC(C)(C)OC(=O)N1CCC2(CCCC2)CC1]

To a solution of 8-azaspiro[4.5]decane (which has been described in WO 9800404 A1 6.2 g, 44.5 mmol) in dichloromethane (130 ml), which was cooled to 0° C., triethylamine (7.5 ml, 53.4 mmol) was added then a solution of tert-butyl dicarbonate (10.68 g, 48.9 mmol) in dichloromethane (50 ml) was added in 20 minutes. The clear solution was maintained under stirring at room temperature for 18 hours, then dichloromethane (50 ml) was added and the organic solution was washed with water (2×20 ml), HCl 0.1N (20 ml) then water (2×20 ml). The organic solvent was anhydrified (Na₂SO₄) and evaporated to give a crude that was purified on silica gel column (Hexane/AcOEt 95/5) to give 6 g of the title compound (light yellow solid).

Example 45

Preparation of Intermediate 72: (±)tert-butyl 7-formyl-8-azaspiro[4.5]decane-8-carboxylate

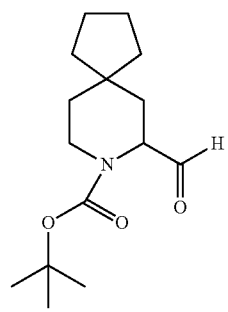 [SMILES: CC(C)(C)OC(=O)N1CCC2(CCCC2)CC1C=O]

tert-butyl 8-azaspiro[4.5]decane-8-carboxylate (Intermediate 71, 6 g, 25.07 mmol) dissolved in 150 ml of Et₂O was cooled to −78° C., then N,N,N',N'-tetramethyl ethylendiamine (9.08 ml, 60.16 mmol) and secBuLi 1.4M in hexane (42.95 ml, 60.16 mmol) were added. After 10 minutes at −60° C., the temperature was raised to −20° C. for 60 minutes, then the reaction was cooled to −78° C. and dimethylformamide (4.47 ml, 60.16 mmol, dissolved in 5 ml of Et₂O) was added. After 30 minutes a saturated aqueous solution of NH₄Cl (30 ml) was slowly added, then reaction was allowed to reach room temperature. Reaction was extracted with Et₂O (3×100 ml), the organic solvent was dried (Na₂SO₄) and evaporated to obtain 4 g of the title compound as yellow oil.

Example 46

Preparation of Intermediate 73: (±)tert-butyl 7-(((6-methylpyridin-2-yl)amino)methyl)-8-azaspiro[4.5]decane-8-carboxylate

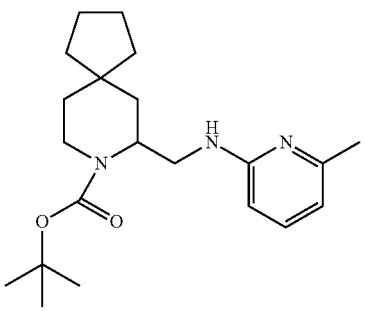 [SMILES: Cc1cccc(NCC2CC3(CCCC3)CCN2C(=O)OC(C)(C)C)n1]

(±)tert-butyl 7-formyl-8-azaspiro[4.5]decane-8-carboxylate (Intermediate 72, 2 g, 7.48 mmol) was dissolved in dichloroethane (25 ml), then acetic acid (5 eq) and 2-amino 6 picoline (810 mg, 7.48 mmol) were added. After 3 hours at room temperature NaBH(OAc)₃ (2.53 g, 11.96 mmol) was added and the reaction was maintained under stirring at room temperature for 18 hours. The reaction was poured in aqueous NaHCO₃ and extracted with ethylacetate. The organic layers were combined, dried (Na$_2$SO$_4$) and concentrated under vacuum; the crude was then purified by silica gel column chromatography (petroleum ether/ethyl acetate=9/1) to obtain 1.3 g of intermediate as colourless oil.

Example 47

Preparation of Intermediate 74: (±)tert-butyl 7-(((5-chloropyridin-2-yl)amino)methyl)-8-azaspiro[4.5]decane-8-carboxylate

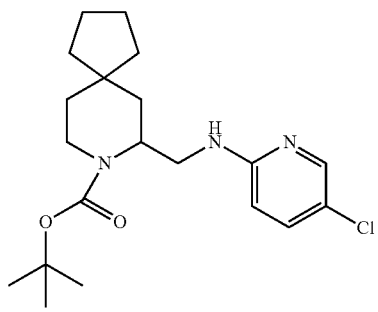 [SMILES: CC(C)(C)OC(=O)N1CCC2(CCCC2)CC1CNc1ccc(Cl)cn1]

(±)tert-butyl 7-formyl-8-azaspiro[4.5]decane-8-carboxylate (Intermediate 72, 2 g, 7.48 mmol) was dissolved in dichloroethane (25 ml), then acetic acid (5 eq) and 2-amino 5 chloropyridine (961 mg, 7.48 mmol) were added. After 3 hours at room temperature NaBH(OAc)$_3$ (2.53 g, 11.96 mmol) was added and the reaction was maintained under stirring at room temperature for 18 hours. The reaction was poured in aqueous NaHCO$_3$ and extracted with ethylacetate. The organic layers were combined, dried (Na$_2$SO$_4$) and concentrated under vacuum; the crude was purified by silica gel column chromatography (petroleum ether/ethyl acetate=9/1). 1 g of intermediate 74 were obtained as colourless oil.

Example 48

Preparation of Intermediate 75: (±)N-(8-azaspiro[4.5]decan-7-ylmethyl)-6-methylpyridin-2-amine

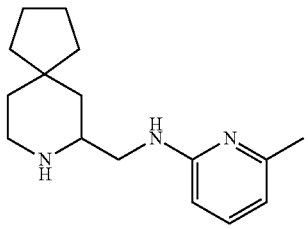 [SMILES: Cc1cccc(NCC2CC3(CCCC3)CCN2)n1]

(±)tert-butyl 7-(((6-methylpyridin-2-yl)amino)methyl)-8-azaspiro[4.5]decane-8-carboxylate (intermediate 73, 1.3 g, 3.62 mmol) was dissolved in dichloromethane (10 ml) and cooled to 0° C., then trifluoroacetic acid (30 ml) was added. After 1 hour at 0° C. and 2 hours at room temperature the solution was evaporated, the residue re-dissolved in dichloromethane was washed with saturated NaHCO$_3$ aqueous solution. The organic layers were dried (Na$_2$SO$_4$) and concentrated under vacuum to obtain 900 mg of the title compound.

MS (ESI) m/z 260 [M+H]$^+$

Example 49

Preparation of Intermediate 76: (±)N-(8-azaspiro[4.5]decan-7-ylmethyl)-5-chloropyridin-2-amine

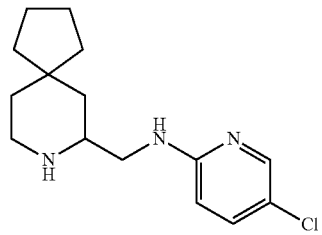 [SMILES: Clc1ccc(NCC2CC3(CCCC3)CCN2)nc1]

(±)tert-butyl 7-(((5-chloropyridin-2-yl)amino)methyl)-8-azaspiro[4.5]decane-8-carboxylate (intermediate 74, 1 g, 2.63 mmol) was dissolved in dichloromethane (10 ml) and cooled to 0° C., then trifluoroacetic acid (30 ml) was added. After 1 hour at 0° C. and 2 hours at room temperature the solution was evaporated, the residue re-dissolved in dichloromethane was washed with saturated NaHCO$_3$ aqueous solution. The organic layers were dried (Na$_2$SO$_4$) and concentrated under vacuum to obtain Obtained 600 mg of the title compound.

MS (ESI) m/z 281 [M+H]$^+$

Preparation of the Disclosure Compounds

Example 50

Compound 1: (±) (2-methyl-5-phenylthiazol-4-yl)(5-(((6-methylpyridin-2-ylamino)methyl)-6-azaspiro[2.5]octan-6-yl)methanone

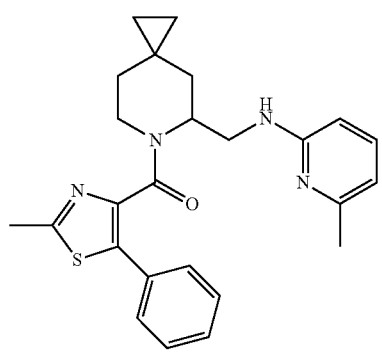 [SMILES: Cc1cccc(NCC2CC3(CCN2C(=O)c2nc(C)sc2-c2ccccc2)CC3)n1]

Intermediate 7 (30 mg, 0.129 mmol)) was dissolved in dichloromethane (2 ml), then diisopropyl ethylamine (75 µl, 0.427 mmol) and O-(benzotriazol-1-yl)-N,N,N'N'-tetramethyluronium hexafluorophosphate (69 mg, 0.18 mmol) were added. After 30 minutes at room temperature 2-methyl-5-phenylthiazole-4-carboxylic acid, whose preparation has been described in U.S. Pat. No. 3,282,927(40 mg, 0.18 mmol), was dissolved in dichloromethane (2 ml) and dimethylformamide (1 ml) and added to the reaction. After 18 hours at room temperature the mixture was poured in aqueous NaHCO$_3$ and extracted with AcOEt. The organic layers were combined, dried (Na$_2$SO$_4$) and concentrated under vacuum; the obtained crude was purified by silica gel column chromatography (petroleum ether/ethyl acetate=7/3), thus obtaining 12 mg of compound 1 as white solid.

MS (ESI) m/z 433.1 [M+H]$^+$; $^1$HNMR [the product is present as a mixture of conformers. The assignment refers to the major component] (CDCl$_3$) δ ppm 7.84 (d, 1H) 7.25-7.64 (m, 5H) 6.48 (d, 1H) 6.11 (d, 1H) 4.95-4.98 (m, 1H) 3.70-3.85 (m, 1H) 3.44-3.55 (m, 1H) 2.95-3.15 (m, 1H) 2.74 (s, 3H) 2.50 (s, 3H) 1.80-1.95 (m, 1H) 1.32-1.15 (m, 2H) 0.89-0.80 (m, 2H) 0.57-0.15 (m, 4H).

The enantiomeric mixture of (±) (2-methyl-5-phenylthiazol-4-yl)(5-((6-methylpyridin-2-ylamino)methyl)-6-azaspiro[2.5]octan-6-yl)methanone (compound 1, 30 mg) was separated by chiral preparative HPLC (preparative chromatographic conditions: Method C) to give two enantiomers:

Example 51

Compound 2: (2-methyl-5-phenylthiazol-4-yl)(5-((6-methylpyridin-2-ylamino)methyl)-6-azaspiro[2.5]octan-6-yl)methanone (Isomer A)

HPLC retention time: 36.3 min (10 mg)

Example 52

Compound 3: (2-methyl-5-phenylthiazol-4-yl)(5-((6-methylpyridin-2-ylamino)methyl)-6-azaspiro[2.5]octan-6-yl)methanone (Isomer B)

HPLC retention time: 38.6 min (6 mg)

Example 53

Compound 4: (±) (5-((5-chloropyridin-2-ylamino)methyl)-6-azaspiro[2.5]octan-6-yl)(2-methyl-5-phenylthiazol-4-yl)methanone

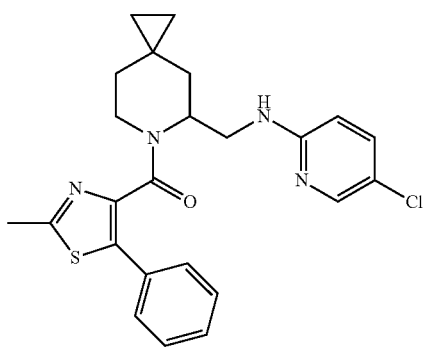 [SMILES: Cc1nc(C(=O)N2CCC3(CC3)CC2CNc2ccc(Cl)cn2)c(-c2ccccc2)s1]

Intermediate 8 (60 mg, 0.238 mmol) was dissolved in dichloromethane (2 ml), then diisopropyl ethylamine (137 µl, 0.786 mmol) and O-(benzotriazol-1-yl)-N,N,N'N'-tetramethyluronium hexafluorophosphate (126 mg, 0.33 mmol) were added. After 30 minutes at room temperature 2-methyl-5-phenylthiazole-4-carboxylic acid (73 mg, 0.33 mmol) was dissolved in dichloromethane (2 ml) and dimethylformamide (1 ml) and added to the reaction. After 18 hours at room temperature the mixture was poured in aqueous NaHCO$_3$ saturated solution and extracted with ethylacetate. The organic layers were combined, dried (Na$_2$SO$_4$) and concentrated under vacuum; crude product was purified by silica gel column chromatography (petroleum ether/ethylacetate=1/1 to ethylacetate), thus obtaining 37 mg of compound 4 as white solid.

MS (ESI) m/z 453.1 [M+H]$^+$; $^1$HNMR [the product is present as a mixture of conformers. The assignment refers to the major component] (CDCl$_3$) δ ppm 7.92 (s, 1H) 7.28-7.51 (m, 5H) 6.33 (d, 1H) 5.57 (m, 1H) 4.68-4.71 (m, 1H) 3.89-3.95 (m, 1H) 3.41-3.46 (m, 1H) 3.10-3.25 (m, 1H) 2.90-3.05 (m, 1H) 2.81 (s, 3H) 1.80-1.90 (m, 1H) 1.20-1.50 (m, 1H) 0.87 (d, 1H) 0.70 (d, 2H) 0.35-0.50 (m, 2H) 0.15-0.30 (m, 2H).

The enantiomeric mixture of (±) (5-((5-chloropyridin-2-ylamino)methyl)-6-azaspiro[2.5]octan-6-yl)(2-methyl-5-phenylthiazol-4-yl)methanone (compound 4, 75 mg) was separated by chiral preparative HPLC (preparative chromatographic conditions:method A) to give two enantiomers:

Example 54

Compound 5: (5-((5-chloropyridin-2-ylamino)methyl)-6-azaspiro[2.5]octan-6-yl)(2-methyl-5-phenylthiazol-4-yl)methanone (Isomer A)

HPLC retention time: 16 min (23 mg)

Example 55

Compound 6: (5-((5-chloropyridin-2-ylamino)methyl)-6-azaspiro[2.5]octan-6-yl)(2-methyl-5-phenylthiazol-4-yl)methanone (Isomer B)

HPLC retention time: 18 min (26 mg)

Example 56

Compound 7: (±) (2-methyl-5-phenylthiazol-4-yl)(5-((5-(trifluoromethyl)pyridin-2-ylamino)methyl)-6-azaspiro[2.5]octan-6-yl)methanone

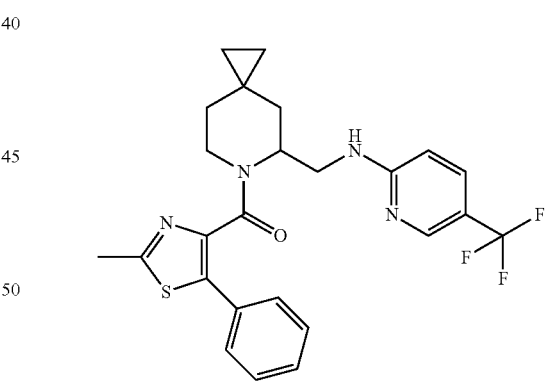

Intermediate 9 (60 mg, 0.210 mmol)) was dissolved in dichloromethane (2 ml), diisopropyl ethylamine (121 µl, 0.693 mmol) and O-(benzotriazol-1-yl)-N,N,N'N'-tetramethyluronium hexafluorophosphate (112 mg, 0.294 mmol) were added. After 30 minutes at room temperature 2-methyl-5-phenylthiazole-4-carboxylic acid (65 mg, 0.294 mmol) was dissolved in dichloromethane (2 ml) and dimethylformamide (1 ml) and added to the reaction. After 18 hours at room temperature the mixture was poured in aqueous NaHCO$_3$ saturated solution and extracted with ethylacetate. The organic layers were combined, dried (Na$_2$SO$_4$) and concentrated under vacuum; the obtained crude product was purified by silica gel column chromatography (gradient from dichloromethane/Ethyl acetate=1/1 to Ethyl acetate), thus obtaining 15 mg of compound 7 as white solid.

MS (ESI) m/z 509 [M+Na]⁺. ¹HNMR [the product is present as a mixture of conformers. The assignment refers to the major component] (CD₃OD) δ ppm 8.05 (s, 1H) 7.39-7.60 (m, 5H) 6.41 (d, 1H) 4.65 (m, 1H) 4.20 (m, 1H) 3.69-3.76 (m, 1H) 3.28-3.35 (m, 1H) 3.10-3.15 (m, 1H) 2.43 (s, 3H) 1.82 (m, 1H) 1.30-1.45 (m, 1H) 0.90-1.05 (m, 2H) 0.6-0.68 (m, 1H) 0.30-0.55 (m, 2H) 0.15-0.25 (m, 2H).

The enantiomeric mixture of (±) (2-methyl-5-phenylthiazol-4-yl)(5-((5-(trifluoromethyl)pyridin-2-ylamino)methyl)-6-azaspiro[2.5]octan-6-yl)methanone (compound 7, 8 mg) was separated by chiral preparative HPLC (preparative chromatographic conditions:Method A) to give the pure enantiomer:

Example 57

Compound 8: (2-methyl-5-phenylthiazol-4-yl)(5-((5-(trifluoromethyl)pyridin-2-ylamino)methyl)-6-azaspiro[2.5]octan-6-yl)methanone (single enantiomer)

HPLC retention time: 17.9 min (4 mg).

Example 58

Compound 9: (±) (5-((5-chloropyridin-2-ylamino)methyl)-6-azaspiro[2.5]octan-6-yl)(2-(cyclopropylmethoxy)phenyl)methanone

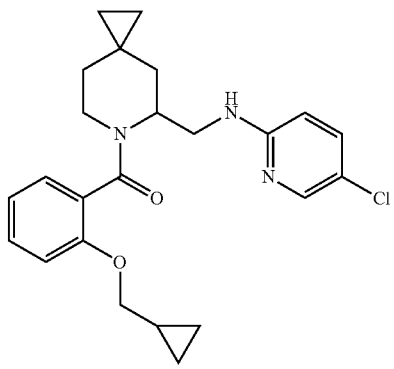 [SMILES: O=C(c1ccccc1OCC1CC1)N1CCC2(CC2)CC1CNc1ccc(Cl)cn1]

Intermediate 8 (50 mg, 0.198 mmol)) was dissolved in dichloromethane (2 ml), then diisopropyl ethylamine (115 µl, 0.65 mmol) and O-(benzotriazol-1-yl)-N,N,N'N'-tetramethyluronium hexafluorophosphate (105 mg, 0.277 mmol) were added. After 30 minutes at room temperature 2-(cyclopropylmethoxy) benzoic acid, whose preparation has been described in Journal of Medicinal Chemistry (1993), 36(10), 1387-92 (Intermediate 10, 53 mg, 0.277 mmol) was dissolved in dichloromethane (2 ml) and dimethylformamide (1 ml) and added to the reaction. After 18 hours at room temperature the mixture was poured in aqueous NaHCO₃ saturated solution and extracted with ethylacetate. The organic layers were combined, dried (Na₂SO₄) and concentrated under vacuum; the obtained crude product was purified by silica gel column chromatography (gradient Petroleum ether/Ethyl acetate=8/2 to 1/1), thus obtaining 12 mg of compound 9 as white solid.

MS (ESI) m/z: 426 [M+H]⁺. ¹HNMR [the product is present as a mixture of conformers. The assignment refers to the major component] (CDCl₃) δ ppm 8.02 (s, 1H) 6.75-7.29 (m, 6H) 6.45 (d, 1H) 5.0-5.32 (m, 2H) 3.75-4.05 (m, 4H) 3.20-3.50 (m, 1H) 2-2.40 (m, 2H) 1.1-1.45 (m, 2H) 0.73-0.76 (m, 1H) 0.2-0.7 (m, 8H).

Example 59

Compound 10: (±) (5-((5-chloropyridin-2-ylamino)methyl)-6-azaspiro[2.5]octan-6-yl)(5-(4-fluorophenyl)-2-methylthiazol-4-yl)methanone

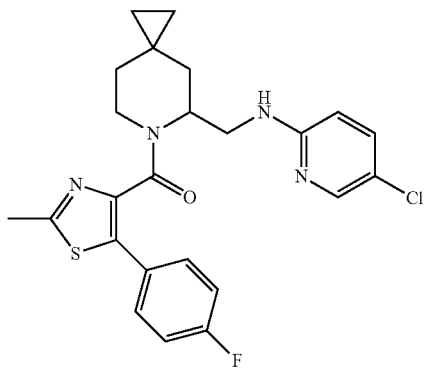 [SMILES: Cc1nc(C(=O)N2CCC3(CC3)CC2CNc2ccc(Cl)cn2)c(-c2ccc(F)cc2)s1]

To a solution of hydroxybenzotriazole (12 mg, 0.09 mmole) and 1-ethyl-3-(3-dimethylaminopropyl)carbodiimide HCl (23 mg, 0.12 mmole) in anhydrous dichloromethane (1.5 ml), 5-(4-fluorophenyl)-2-methylthiazole-4-carboxylic acid (20 mg, 0.08 mmole) was added and the resulting solution was stirred 15 min. (±) N-(6 azaspiro[2.5]octan-5-ylmethyl)-5-chloropyridin-2-amine (Intermediate 8, 20 mg, 0.08 mmole) was added and the mixture stirred for further 3 hours at room temperature. The reaction mixture was diluted with dichloromethane (2 ml) and washed with NaHCO₃ saturated solution (3×5 ml). After drying over Na₂SO₄ and filtration, the organic phase was evaporated under vacuum and the residue was purified by SPE-Si cartridge (5 g) eluting with a mixture dichloromethane:MeOH (from dichloromethane to dichloromethane:MeOH 95:5).

39.8 mg of desired compound as mixture 1:0.57 of conformers were isolated.

MS (ESI); m/z 471 [MH]⁺

¹HNMR [the product is present as a mixture of conformers. The assignment refers to the major component] (CDCl₃) δ ppm 7.9 (d, 1H) 7.50-7.42 (m, 2H) 7.28-7.25 (dd, 1H) 7.12-7.09 (t, 1H) 6.34-6.31 (d, 1H) 5.65 (m, 1H) 4.66-4.65 (m, 1H) 3.96-3.90 (m, 1H) 3.21-3.17 (m, 1H) 3.01-2.94 (dt, 1H) 2.60 (s, 3H) 2.15-2.05 (dd, 1H) 1.9-1.77 (dt, 1H) 1.46-1.42 (dd, 1H) 0.77-0.74 (d, 1H) 0.49-0.39 (m, 2H) 0.25-0.15 (m, 2H).

Example 60

Compound 11: (±)(5-((5-chloropyridin-2-ylamino)methyl)-6-azaspiro[2.5]octan-6-yl)(5-methyl-2-(2H-1,2,3-triazol-2-yl)phenyl)methanone

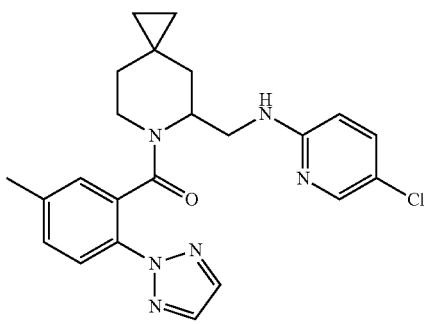 [SMILES: Cc1ccc(-n2nccn2)c(C(=O)N2CCC3(CC3)CC2CNc2ccc(Cl)cn2)c1]

To a solution of hydroxybenzotriazole (12.9 mg, 0.095 mmol) and O-(benzotriazol-1-yl)-N,N,N'N'-tetramethyluronium hexafluorophosphate HCl (23 mg, 0.12 mmol) in anhydrous dichloromethane (2 ml), 5-methyl-2-(2H-1,2,3-triazol-2-yl)benzoic acid (19.4 mg, 0.095 mmole) was added and the resulting solution was stirred for 1 h at room temperature. (±) N-(6 azaspiro[2.5]octan-5-ylmethyl)-5-chloropyridin-2-amine (Intermediate 8, 20 mg, 0.08 mmol) was added and the resulting mixture was stirred at the same temperature overnight. The mixture was washed with NaHCO₃ saturated solution (3×5 ml).

After drying over Na₂SO₄ and filtration, the organic phase was evaporated under vacuum and the residue was purified by SPE-Si cartridge (2 g) eluting with a mixture dichloromethane:MeOH (from dichloromethane to dichloromethane:MeOH 98:2).

29 mg of the desired compound as mixture of conformers were isolated.

MS (ESI); m/z 436 [MH]$^+$ $^1$HNMR [the product is present as a mixture of conformers. The assignment refers to the major component] (CDCl₃) δ ppm 8.08-8.07 (d, 1H) 7.95-7.92 (m, 1H) 7.85-7.79 (m, 2H) 7.7 (s, 2H) 7.35-7.33 (d, 1H) 6.40-6.38 (d, 1H) 5.61-5.60 (d, 1H) 5.21-5.14 (m, 1H) 3.90-3.84 (m, 1H) 3.66-3.59 (m, 1H) 3.41-3.32 (m, 1H) 3.11-3.01 (m, 1H) 2.45 (s, 3H) 2.29-2.21 (dd, 1H) 1.99-1.85 (m, 1H) 1.19-1.16 (d, 1H) 0.75-0.68 (d, 1H) 0.58-0.27 (m, 4H)

Example 61

Compound 12: (±)(5-((5-chloropyridin-2-ylamino)methyl)-6-azaspiro[2.5]octan-6-yl)(5-methyl-2-(pyrimidin-2-yl)phenyl)methanone

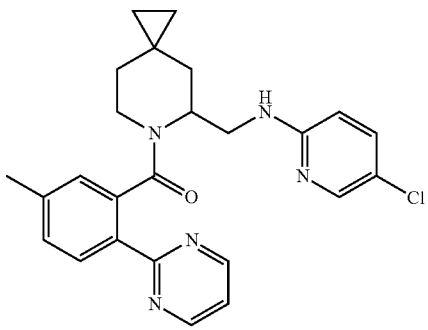 [SMILES: Cc1ccc(-c2ncccn2)c(C(=O)N2CCC3(CC3)CC2CNc2ccc(Cl)cn2)c1]

To a solution of hydroxybenzotriazole (13 mg, 0.095 mmol) and O-(benzotriazol-1-yl)-N,N,N'N'-tetramethyluronium hexafluorophosphate HCl (23 mg, 0.12 mmol) in anhydrous dichloromethane (2 ml), 5-methyl-2-(pyrimidin-2-yl)benzoic acid (20.4 mg, 0.095 mmole) was added and the resulting solution was stirred 1 h at room temperature. (±) N-(6 azaspiro[2.5]octan-5-ylmethyl)-5-chloropyridin-2-amine (Intermediate 8, 20 mg, 0.08 mmol) was added and the resulting mixture was stirred at the same temperature overnight. The reaction mixture was washed with NaHCO₃ saturated solution (3×5 ml). After drying over Na₂SO₄ and filtration, the organic phase was evaporated under vacuum and purified by SPE-Si cartridge (2 g) eluting with a mixture dichloromethane:MeOH (from dichloromethane to dichloromethane:MeOH 98:2).

10 mg of the desired compound as mixture of conformers were isolated.

MS (ESI); m/z 446 [MH]$^+$ $^1$HNMR [the product is present as a mixture of conformers. The assignment refers to the major component] (CDCl₃) δ ppm 8.80-8.77 (m, 1H) 8.64-8.6 (d, 1H) 8.36-8.31 (d, 1H) 8.08-8.04 (m, 1H) 7.43-7.17 (m, 3H) 7.08-7.03 (t, 1H) 6.36-6.31 (d, 1H) 5.79 (bs, 1H) 5.19-5.11 (m, 1H) 4.00-3.89 (m, 1H) 3.71-3.62 (m, 1H) 3.50-3.39 (m, 1H) 3.37-3.21 (m, 1H) 2.45 (s, 3H) 2.31-2.24 (dd, 1H) 1.99-1.88 (dt, 1H) 1.25-1.19 (d, 1H) 0.75-0.68 (d, 1H) 0.60-0.13 (m, 4H).

The enantiomeric mixture of (±)(5-((5-chloropyridin-2-ylamino)methyl)-6-azaspiro[2.5]octan-6-yl)(5-methyl-2-(pyrimidin-2-yl)phenyl)methanone (compound 12, 550 mg) was separated by chiral preparative HPLC (preparative chromatographic conditions: method B) to give the single enantiomer (Compounds 13):

Example 62

Compound 13: (S)-(5-(((5-chloropyridin-2-yl)amino)methyl)-6-azaspiro[2.5]octan-6-yl)(5-methyl-2-(pyrimidin-2-yl)phenyl)methanone (Isomer A) HPLC retention time: 9 min (150 mg)

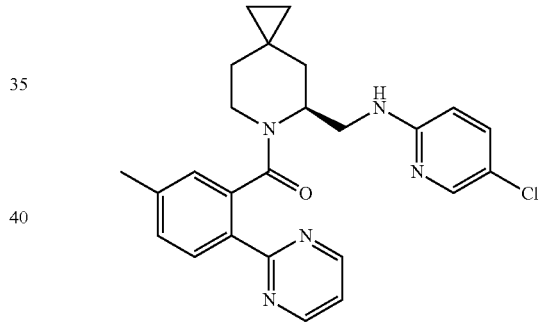

Alternatively Compound 13 was obtained by the following procedure: 5-methyl-2-(pyrimidin-2-yl)benzoic acid (428 mg, 2 mmol; prepared according to WO 2008147518), intermediate 34 (500 mg, 2 mmol) and DIPEA (0.65 ml) were dissolved in DCM (5 ml) at 0° C., then T3P (50% in DCM, 1.5 g) was added. The mixture is stirred at reflux for 8 hours then at RT overnight. The reaction was washed with NaOH 1M and water, dried (Na₂SO₄) and evaporated. The crude was purified by silica gel column chromatography (DCM to DCM/MeOH=95/05). 180 mg of the desired compound were isolated.

MS (ESI); m/z 446 [MH]$^+$ $^1$HNMR [the product is present as a mixture of conformers. The assignment refers to the major component] (CDCl₃) δ ppm 8.80-8.77 (m, 1H) 8.64-8.6 (d, 1H) 8.36-8.31 (d, 1H) 8.08-8.04 (m, 1H) 7.43-7.17 (m, 3H) 7.08-7.03 (t, 1H) 6.36-6.31 (d, 1H) 5.79 (bs, 1H) 5.19-5.11 (m, 1H) 4.00-3.89 (m, 1H) 3.71-3.62 (m, 1H) 3.50-3.39 (m, 1H) 3.37-3.21 (m, 1H) 2.45 (s, 3H) 2.31-2.24 (dd, 1H) 1.99-1.88 (dt, 1H) 1.25-1.19 (d, 1H) 0.75-0.68 (d, 1H) 0.60-0.13 (m, 4H).

Example 64

Compound 15: (±)methyl 5-chloro-2-((6-(5-(4-fluorophenyl)-2-methylthiazole-4-carbonyl)-6-azaspiro[2.5]octan-5-yl)methylamino)benzoate

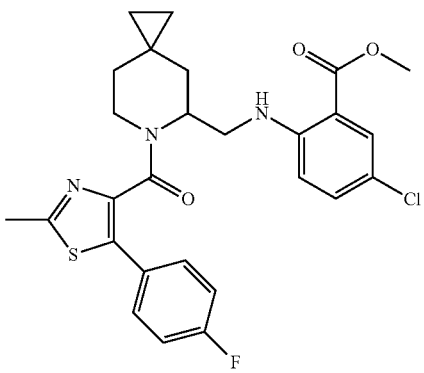

To a solution of hydroxybenzotriazole (13 mg, 0.097 mmol) and O-(benzotriazol-1-yl)-N,N,N'N'-tetramethyluronium hexafluorophosphate HCl (23 mg, 0.12 mmol) in anhydrous dichloromethane (2 ml), 5-(4-fluorophenyl)-2-methylthiazole-4-carboxylic acid (23 mg, 0.097 mmole) was added and the resulting solution was stirred 1 h at room temperature. (±) methyl 2-(6-azaspiro[2.5]octan-5-ylmethylamino)-5-chlorobenzoate (intermediate 10) (20 mg, 0.08 mmol) was added and the resulting mixture was stirred at the same temperature overnight. The mixture was washed with NaHCO₃ saturated solution (3×5 ml).

After drying over Na₂SO₄ and filtration, the organic phase was evaporated under vacuum and purified by SPE-Si cartridge (2 g) eluting with a mixture dichloromethane:MeOH (from dichloromethane to dichloromethane:MeOH 98:2). 35 mg of the desired compound were isolated.

MS (ESI); m/z 528 [MH]⁺

Examples 64-87

Preparation of Compounds 16-35, 3739

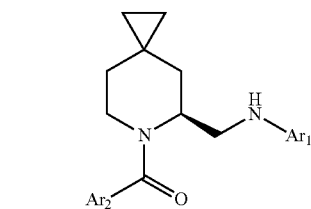

In the above formula, $Ar_1$ is Q and $Ar_2$ is R in Formula (VIa).

General Procedure 6

$Ar_2$—COOH (1 eq; prepared according to WO 2008147518 for compounds 19, 20, 26-35, 37-39 and according to U.S. Pat. No. 3,282,927 for compounds 16, 17, 18, 21-25), HOBT (1 eq) and EDCl.HCl (1.5 eq) dissolved in dichloromethane (5 ml/mmol) were stirred at 25° C. for 0.5-2 hours, then intermediates 34-45 dissolved in dichloromethane were added. After 18 hours the mixture was poured in an aqueous saturated solution of NaHCO₃ and extracted with dichloromethane. The crude was purified by silica gel column chromatography (DCM to DCM/MeOH=9/1)

General Procedure 7

$Ar_2$—COOH (1 eq; prepared according to WO 2008147518 for compounds 19, 20, 26-39 and according to U.S. Pat. No. 3,282,927 for compounds 16, 17, 18, 21-25), intermediates 34-45 (1 eq) and DIPEA (2 eq) were dissolved in dichloromethane (5 ml/mmol) at 0° C., then T3P (50% in dichloromethane, 1.2 eq) was added. The mixture is stirred at reflux for 3-5 hours then at RT overnight. The reaction was washed with NaOH 1M and water, dried (Na₂SO₄) and evaporated. The crude was purified by silica gel column chromatography (DCM to DCM/MeOH=9/1). The enantiomeric purity was calculated as enantiomeric eccess (ee %) by chiral HPLC methods.

According to general procedure 6 or 7 the following compounds were prepared:

| Comp. | Name | Procedure | Yield % |
|---|---|---|---|
| 16 | (S)-(5-(((5-fluoropyridin-2-yl)amino)methyl)-6-azaspiro[2.5]octan-6-yl)(2-methyl-5-phenylthiazol-4-yl)methanone | 6 | 63 |
| 17 | (S)-(5-(((6-chloropyridin-2-yl)amino)methyl)-6-azaspiro[2.5]octan-6-yl)(2-methyl-5-phenylthiazol-4-yl)methanone | 6 | 83 |
| 18 | (S)-(2-methyl-5-phenylthiazol-4-yl)(5-(((6-(trifluoromethyl)pyridin-2-yl)amino)methyl)-6-azaspiro[2.5]octan-6-yl)methanone | 6 | 82 |
| 19 | (S)-(5-(((6-chloropyridin-2-yl)amino)methyl)-6-azaspiro[2.5]octan-6-yl)(5-methyl-2-(2H-1,2,3-triazol-2-yl)phenyl)methanone | 6 | 80 |
| 20 | (S)-(5-methyl-2-(2H-1,2,3-triazol-2-yl)phenyl)(5-(((6-(trifluoromethyl)pyridin-2-yl)amino)methyl)-6-azaspiro[2.5]octan-6-yl)methanone | 6 | 78 |
| 21 | (S)-(2-methyl-5-phenylthiazol-4-yl)(5-(((4-methylpyrimidin-2-yl)amino)methyl)-6-azaspiro[2.5]octan-6-yl)methanone | 6 | 60 |
| 22 | (S)-(5-(((4,6-dimethylpyrimidin-2-yl)amino)methyl)-6-azaspiro[2.5]octan-6-yl)(2-methyl-5-phenylthiazol-4-yl)methanone | 6 | 63 |
| 23 | (S)-(2-methyl-5-phenylthiazol-4-yl)(5-(((5-methylpyrimidin-2-yl)amino)methyl)-6-azaspiro[2.5]octan-6-yl)methanone | 6 | 80 |
| 24 | (S)-(5-(((4,6-difluoropyrimidin-2-yl)amino)methyl)-6-azaspiro[2.5]octan-6-yl)(2-methyl-5-phenylthiazol-4-yl)methanone | 6 | 80 |
| 25 | (S)-(5-(((6-fluoropyridin-2-yl)amino)methyl)-6-azaspiro[2.5]octan-6-yl)(2-methyl-5-phenylthiazol-4-yl)methanone | 6 | 71 |
| 26 | (S)-(5-methyl-2-(2H-1,2,3-triazol-2-yl)phenyl)(5-(((5-(trifluoromethyl)pyridin-2-yl)amino)methyl)-6-azaspiro[2.5]octan-6-yl)methanone | 6 | 52 |
| 27 | (S)-(5-methyl-2-(pyrimidin-2-yl)phenyl)(5-(((5-(trifluoromethyl)pyridin-2-yl)amino)methyl)-6-azaspiro[2.5]octan-6-yl)methanone | 7 | 44 |

-continued

| Comp. | Name | Procedure | Yield % |
|---|---|---|---|
| 28 | (S)-(2-(2H-1,2,3-triazol-2-yl)phenyl)(5-(((5-chloropyridin-2-yl)amino)methyl)-6-azaspiro[2.5]octan-6-yl)methanone | 6 | 13 |
| 29 | (S)-(5-(((5-chloropyridin-2-yl)amino)methyl)-6-azaspiro[2.5]octan-6-yl)(5-fluoro-2-(2H-1,2,3-triazol-2-yl)phenyl)methanone | 6 | 56 |
| 30 | (S)-(5-(((5-chloropyridin-2-yl)amino)methyl)-6-azaspiro[2.5]octan-6-yl)(2-(pyrazin-2-yl)phenyl)methanone | 6 | 9 |
| 31 | (S)-(5-(((5-chloropyridin-2-yl)amino)methyl)-6-azaspiro[2.5]octan-6-yl)(2-fluoro-6-(2H-1,2,3-triazol-2-yl)phenyl)methanone | 6 | 17 |
| 32 | (S)-(5-(((5-chloropyridin-2-yl)amino)methyl)-6-azaspiro[2.5]octan-6-yl)(5-fluoro-2-(pyridin-2-yl)phenyl)methanone | 6 | 54 |
| 33 | (S)-(5-(((5-chloropyridin-2-yl)amino)methyl)-6-azaspiro[2.5]octan-6-yl)(5-methyl-2-(pyridin-2-yl)phenyl)methanone | 6 | 76 |
| 34 | (S)-(5-(((5-chloropyridin-2-yl)amino)methyl)-6-azaspiro[2.5]octan-6-yl)(2-fluoro-6-(pyridin-2-yl)phenyl)methanone | 6 | 32 |
| 35 | (S)-[1,1'-biphenyl]-2-yl(5-(((4,6-dimethylpyrimidin-2-yl)amino)methyl)-6-azaspiro[2.5]octan-6-yl)methanone | 6 | 50 |
| 37 | (S)-(2,5-dichlorophenyl)(5-(((4,6-dimethylpyrimidin-2-yl)amino)methyl)-6-azaspiro[2.5]octan-6-yl)methanone | 6 | 55 |
| 38 | (S)-[1,1'-biphenyl]-2-yl(5-(((5-chloropyridin-2-yl)amino)methyl)-6-azaspiro[2.5]octan-6-yl)methanone | 6 | 34 |
| 39 | (S)-[1,1'-biphenyl]-2-yl(5-(((4-methylpyrimidin-2-yl)amino)methyl)-6-azaspiro[2.5]octan-6-yl)methanone | 6 | 50 |

Compounds 16-39 Characterization:

| Comp. | Ar1 | Ar2 | $^1$H-NMR | MS | ee % |
|---|---|---|---|---|---|
| 16 | 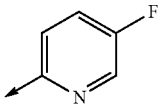 | 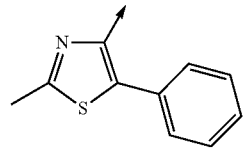 | $^1$HNMR (CDCl$_3$) δ ppm 7.87-7.95 (m, 1H), 7.51 (m, 2H), 7.40 (m, 2H), 7.33 (m, 1H), 7.12-7.28 (m, 1H), 6.32-6.54 (m, 1H), 4.71-5.41 (m, 1H), 3.85-4.03 (m, 2H), 3.46 (m, 1H), 2.94-3.23 (m, 3H), 1.84-2.12 (m, 1H), 1.28-1.46 (m, 1H), 0.88-1.15 (m, 1H), 0.59-0.76 (m, 1H), 0.41-0.52 (m, 2H), 0.17-0.82 (m, 2H) | ESI+ m/z 459 [M + Na]$^+$ | 98* Method D |
| 17 | 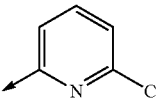 | 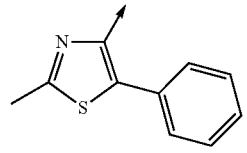 | $^1$HNMR (CDCl$_3$) δ ppm 7.25-7.55 (m, 6H), 6.52-6.59 (m, 1H), 6.23-6.40 (m, 1H), 5.13-5.53 (m, 1H), 3.90-4.76 (m, 1H), 3.86 (m, 1H), 2.93-3.47 (m, 2H), 2.61-2.75 (m, 3H), 1.79-2.2 (m, 1H), 1.29-1.45 (m, 1H), 0.87-1.14 (m, 1H), 0.57-0.74 (m, 1H), 0.33-0.50 (m, 2H), 0.17-0.29 (m, 2H) | ESI+ m/z 475 [M + Na]$^+$ | 40 |
| 18 | 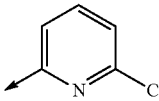 | 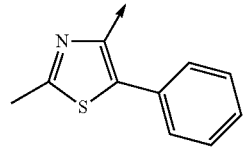 | $^1$HNMR (CDCl$_3$) δ ppm 7.30-7.55 (m, 6H), 6.85-6.95 (m, 1H), 6.50-6.70 (m, 1H), 5.25-5.70 (m, 1H), 4.65-5.15 (m, 1H), 3.92 (m, 1H), 3.50 (m, 1H), 3.25 (m, 1H), 2.2-3 (m, 1H), 2.55-2.70 (m, 3H), 1.75-2.15 (m, 1H), 0.80-1.15 (m, 1H), 0.55-0.75 (m, 1H), 0.35-050 (m, 2H), 0.15-0.30 (m, 2H) | ESI+ m/z 487 [M + Na]$^+$ | 40 |
| 19 | 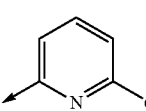 | 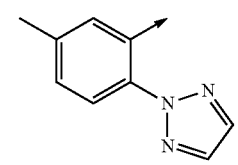 | $^1$HNMR (CDCl$_3$) δ ppm 7.75-7.97 (m, 3H), 7.30-7.40 (m, 2H), 7.08-7.26 (m, 1H), 6.37-6.65 (m, 2H), 5.17 (m, 1H), 4.27-4.83 (m, 1H), 3.79-3.90 (m, 1H), 3.40 (m, 1H), 2.96-3.11 (m, 1H), 2.34-2.45 (m, 1H), 2.11-2.30 (m, 1H), 1.92 (m, 1H), 1.18-1.32 (m, 1H), 0.70-1.07 (m, 1H), 0.44-0.62 (m, 2H), 0.16-0.40 (m, 2H) | ESI+ m/z 459 [M + Na]$^+$ | 40 |
| 20 | 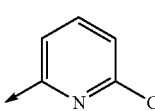 | 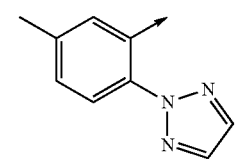 | $^1$HNMR (CDCl$_3$) δ ppm 7.97 (m, 1H), 7.72-7.86 (m, 2H), 7.45-7.58 (m, 1H), 7.15-7.36 (m, 1H), 6.89-7.03 (m, 1H), 6.62-6.82 (m, 1H), 5.79-6.37 (m, 1H), 5.18 (m, 1H), 3.71-4.82 (m, 1H), 3.19-4.37 (m, 1H), 3.86 (m, 1H), 3.36-3.58 (m, 1H), 2.99-3.13 (m, 1H), 2.25-2.45 (m, 3H), 2.09-2.17 (m, 1H), 1.93 (m, 1H), 1.08-1.35 (m, 1H), 0.55-0.76 (m, 1H), 0.19-0.52 (m, 4H) | ESI+ m/z 493 [M + Na]$^+$ | 40 |

-continued

| Comp. | Ar1 | Ar2 | ¹H-NMR | MS | ee % |
|---|---|---|---|---|---|
| 21 | 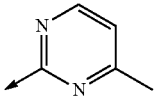 | 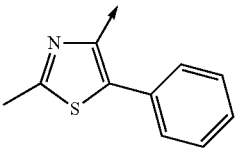 | ¹HNMR (CDCl₃) δ ppm 8.07-8.17 (m, 1H), 7.38-7.53 (m, 5H), 6.39-6.44 (m, 1H), 4.73-5.20 (m, 1H), 3.73-4.10 (m, 2H), 3.01-3.42 (m, 2H), 2.74-2.67 (m, 3H), 2.31-2.36 (m, 3H), 1.80-2.14 (m, 1H), 1.46 (m, 1H), 0.58-1.11 (m, 2H), 0.35-0.52 (m, 2H), 0.15-0.28 (m, 2H) | ESI+ m/z 434 [M + H]⁺ | 90 |
| 22 | 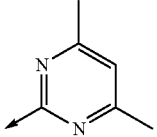 | 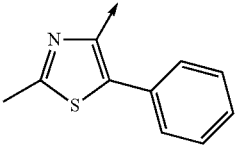 | ¹HNMR (CDCl₃) δ ppm 7.35-7.55 (m, 5H), 6.35 (m, 1H), 4.70-5.35 (m, 1H), 3.73-4.10 (m, 2H), 3.01-3.42 (m, 2H), 2.74-2.67 (m, 3H), 2.31-2.36 (m, 3H), 1.80-2.14 (m, 1H), 1.46 (m, 1H), 0.58-1.11 (m, 2H), 0.35-0.52 (m, 2H), 0.15-0.28 (m, 2H) | ESI+ m/z 448 [M + H]⁺ | 90 |
| 23 | 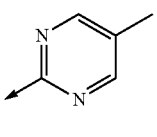 | 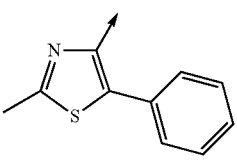 | ¹HNMR (CDCl₃) δ ppm 8.20 (s, 1H), 8.12 (s, 1H), 7.35-7.55 (m, 5H), 4.73-5.35 (m, 1H), 3.75-4.20 (m, 2H), 3.03-3.45 (m, 2H), 2.74-2.78 (m, 3H), 2.15 (s, 3H), 1.85 (m, 2H), 1.52 (m, 1H), 0.80-1.20 (m, 1H), 0.55-0.75 (m, 1H), 0.25-0.52 (m, 2H), 0.15-0.20 (m, 2H) | ESI+ m/z 434 [M + H]⁺ | 90 |
| 24 | 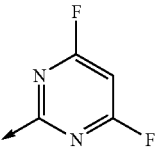 | 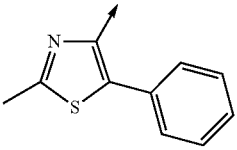 | ¹HNMR (CDCl₃) δ ppm 7.30-7.55 (m, 6H), 5.70-5.95 (m, 1H), 4.75-5.30 (m, 1H), 3.55-4.20 (m, 1H), 3.02-3.25(m, 2H), 2.75-2.79 (m, 3H), 1.55-2.20 (m, 2H), 0.60-1.15 (m, 2H), 0.40-0.60 (m, 2H), 0.35-0.45 (m, 2H), 0.20-0.32 (m, 2H) | ESI+ m/z 456 [M + H]⁺ | 90 |
| 25 | 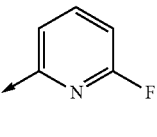 | 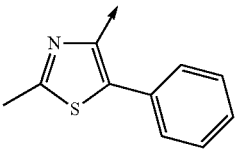 | ¹HNMR (CDCl₃) δ ppm 7.32-7.53 (m, 6H), 6.10-6.25 (m, 1H), 6.07-6.9 (m, 1H), 4.70-5.20 (m, 1H), 3.88-4.10 (m, 1H), 2.95-3.50 (m, 2H), 2.65-2.75 (m, 3H), 1.30-2.10 (m, 3H), 0.60-1.15 (m, 2H), 0.35-0.45 (m, 2H), 0.20-0.29 (m, 2H) | ESI+ m/z 437 [M + H]⁺ | 40 |
| 26 | 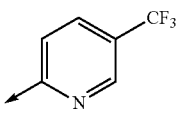 | 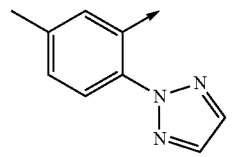 | ¹HNMR (CDCl₃) δ ppm 8.22-8.38 (m, 1H), 7.94-8.14 (m, 1H), 7.79-7.86 (m, 1H), 7.69 (m, 1H), 7.50-7.62 (m, 1H), 7.28-7.37 (m, 1H), 6.48-6.66 (m, 1H), 5.20 (m, 1H), 4.34-4.84 (m, 1H), 3.89-4.0 (m, 1H), 3.65-3.75 (m, 1H), 3.21-3.44 (m, 2H), 3.01-3.11 (m, 1H), 2.26-2.46 (m, 3H), 1.89-2.17 (m, 1H), 1.02-1.28 (m, 1H), 0.19-0.63 (m, 4H) | ESI+ m/z 493 [M + Na]⁺ | 40 |
| 27 | 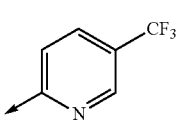 | 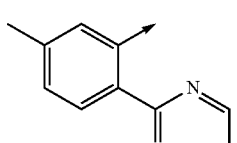 | ¹HNMR (CDCl₃) δ ppm 8.80-8.94 (m, 1H), 8.59 (d, 1H), 8.11-8.40 (m, 2H), 7.50-7.62 (m, 1H), 7.04-7.36 (m, 2H), 6.18-6.63 (m, 2H), 5.18-5.40 (m, 1H), 4.41-4.92 (m, 1H), 3.98-4.20 (m, 1H), 3.70-3.95 (m, 1H), 3.25-3.55 (m, 1H), 2.95-3.12 (m, 1H), 2.30-2.47 (m, 3H), 1.92-2.24 (m, 1H), 0.73-1.11 (m, 1H), 0.21-0.66 (m, 4H) | ESI+ m/z 504 [M + Na]⁺ | 40 |
| 28 | 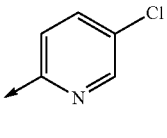 | 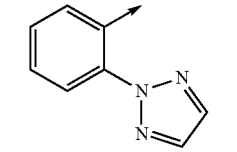 | ¹HNMR (CDCl₃) δ ppm 8.05-8.11 (m, 2H), 7.87-8.0 (m, 2H), 7.40-7.75 (m, 3H), 7.04-7.20 (m, 1H), 6.57 (m, 1H), 5.13 (m, 1H), 3.65-3.95 (m, 2H), 3.0-3.40 (m, 3H), 1.90-2.30 (m, 2H), 1.25-1.45 (m, 2H) 0.25-0.65 (m, 4H) | ESI+ m/z 423 [M + H]⁺ | 98 |
| 29 | 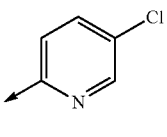 | 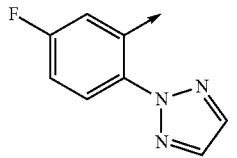 | ¹HNMR (CDCl₃) δ ppm 8.05-8.07 (m, 1H), 7.70-7.93 (m, 3H), 7.39-7.41 (m, 1H), 7.08-7.25 (m, 2H), 6.53 (m, 1H), 5.10 (m, 1H), 3.75-3.89 (m, 2H), 3.08-3.40 (m, 2H), 1.90-2.28 (m, 2H), 1.05-1.45 (m, 2H) 0.15-0.65 (m, 4H) | ESI+ m/z 441 [M + H]⁺ | 98 |

-continued

| Comp. | Ar1 | Ar2 | ¹H-NMR | MS | ee % |
|---|---|---|---|---|---|
| 30 | 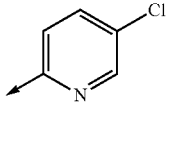 | 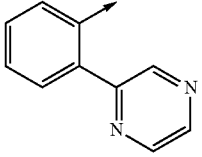 | ¹HNMR (DMSO-$d_6$) δ ppm 8.70-8.71 (m, 1H), 8.66-8.69 (m, 2H), 7.80-7.97 (m, 1H), 7.38-7.80 (m, 3H), 6.90-7.10 (m, 2H), 6.45-6.55 (m, 1H), 4.45-4.90 (m, 1H), 3.54-3.64 (m, 1H), 3.20-3.45 (m, 3H), 2.05-2.94-2.97 (m, 1H) 1.82-2.0 (m, 1H), 1.021-1.024 (m, 1H), 0.58-0.82 (m, 2H), 0.14-0.41 (m, 4H) | ESI+ m/z 434 [M + H]⁺ | 98 |
| 31 | 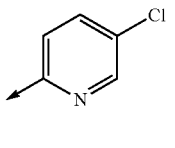 | 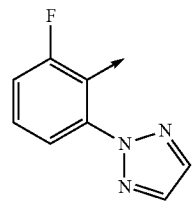 | ¹HNMR (CDCl₃) δ ppm 8.05-8.08 (m, 1H), 7.75-7.95 (m, 3H), 7.30-7.51 (m, 2H), 7.05-7.20 (m, 2H), 6.29-6.45 (m, 1H), 5.66-5.75 (m, 1H), 5.25 (m, 1H), 4.61-4.90 (m, 1H), 3.35-4.02 (m, 3H), 2.05-2.47 (m, 1H) 1.05-1.25 (m, 1H), 0.60-0.90 (m, 2H), 0.19-0.58 (m, 4H) | ESI+ m/z 441 [M + H]⁺ | 98 |
| 32 | 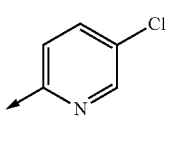 | 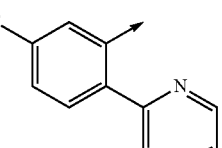 | ¹HNMR (CDCl₃) δ ppm 8.70 (m, 1H), 8.03-8.41 (m, 1H), 7.66-7.93 (m, 3H), 7.05-7.40 (m, 3H), 6.46-6.83 (m, 1H), 6.01-6.21 (m, 1H), 5.05 (m, 1H), 4.20-4.70 (m, 2H), 3.48-3.81 (m, 2H), 2.90-3.30 (m, 2H) 1.50-2.35 (m, 2H), 0.76-1.20 (m, 2H), 0.05-0.60 (m, 4H) | ESI+ m/z 451 [M + H]⁺ | 98 |
| 33 | 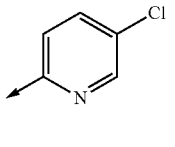 | 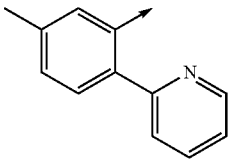 | ¹HNMR (CDCl₃) δ ppm 8.65-8.70 (m, 1H), 8.03-8.40 (m, 1H), 6.99-7.82 (m, 6H), 6.50-6.75 (m, 1H), 6.02-6.23 (m, 1H), 5.05 (m, 1H), 4.2-4.75 (m, 1H), 3.50-3.85 (m, 2H), 2.85-3.20 (m, 1H), 1.50-2.10 (m, 2H) 1.50-2.35 (m, 2H), 0.76-1.15 (m, 2H), 0.05-0.65 (m, 4H) | ESI+ m/z 447 [M + H]⁺ | 98 |
| 34 | 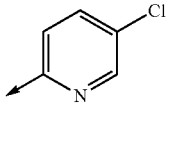 | 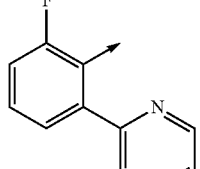 | ¹HNMR (CDCl₃) δ ppm 8.60-8.80 (m, 1H), 7.80-8.06 (m, 1H), 7.55-7.75 (m, 2H), 7.20-7.50 (m, 4H), 6.90-7.20 (m, 1H), 5.90-6.47 (m, 1H), 4.54-5.19 (m, 1H), 3.75-4.0 (m, 1H), 3.35-3.70 (m, 2H), 2.85-3.30 (m, 1H) 1.96-2.54 (m, 2H), 0.75-1.10 (m, 2H), 0.09-0.60 (m, 4H) | ESI+ m/z 451 [M + H]⁺ | 98 |
| 35 | 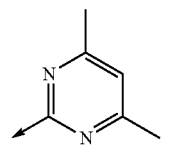 | 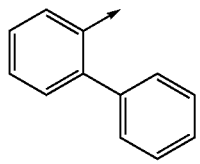 | ¹HNMR (CDCl₃) δ ppm 7.02-7.53 (m, 9H), 6.26-6.32 (m, 1H), 4.80-5.08 (m, 1H), 4.19-4.70 (m, 1H), 3.71 (m, 1H), 2.70-3.45 (m, 2H), 2.31-2.05 (m, 7H), 1.40-1.70 (m, 1H), 0.65-0.90 (m, 1H), 001-0.51 (m, 5H) | ESI+ m/z 427 [M + H]⁺ | 90 |
| 37 | 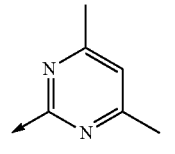 | 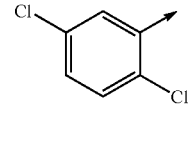 | ¹HNMR (CDCl₃) δ ppm 7.29-7.34 (m, 1H), 7.21-7.24 (m, 1H), 6.67-7.06 (m, 1H), 6.30-6.38 (m, 1H), 5.24 (m, 1H), 4.50-5.01 (m, 2H), 3.10-3.98 (m, 3H), 2.05-2.48 (m, 9H), 0.75-1.20 (m, 2H), 0.33-0.58 (m, 4H) | ESI+ m/z 420 [M + H]⁺ | 90 |
| 38 | 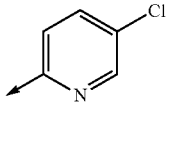 | 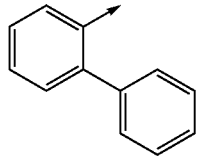 | ¹HNMR (CDCl₃) δ ppm 7.76-8.01 (m, 1H), 7.05-7.51 (m, 10H), 6.01-6.50 (m, 1H), 5.05-5.17 (m, 1H), 4.18-4.71 (m, 1H), 2.87-3.66 (m, 2H), 1.45-2.12 (m, 2H), 0.69-2.15 (m, 1H), 0.25-0.55 (m, 4H), 0.01-0.50 (m, 2H) | ESI+ m/z 433 [M + H]⁺ | 98 |

-continued

| Comp. | Ar1 | Ar2 | ¹H-NMR | MS | ee % |
|---|---|---|---|---|---|
| 39 | 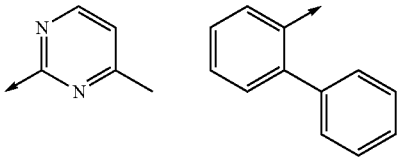 | | ¹HNMR (CDCl₃) δ ppm 7.96-8.15 (m, 1H), 7.04-7.55 (m, 9H), 6.38-6.45 (m, 1H), 5.0-5.45 (m, 1H), 4.16-4.91 (m, 1H), 2.93-3.76 (m, 2H), 2.25-2.34 (m, 3H), 1.45-2.07 (m, 2H), 0.50-1.14 (m, 2H), 0.02-0.48 (m, 5H) | ESI+ m/z 414 [M + H]⁺ | 98 |

\* Compounds were further purified by chiral HPLC to obtain enantiomeric pure products

Examples 87-93

Preparation of Compounds 40-46

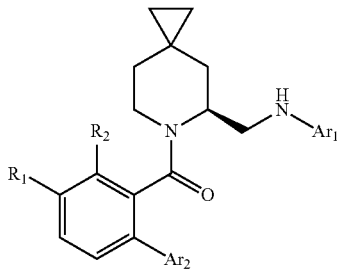

In the above formula, $Ar_1$ is Q and the group phenyl substituted with $R_1$, $R_2$, $Ar_2$ is R in formula (VIa).

General Procedure 8

Intermediates 46-50 (1 eq) was dissolved dry DMF (20 ml/mmol), then CsF (2 eq), CuI (0.2 eq), [Ph₃P]₄Pd (0.1 eq) and the corresponding Ar2-tributylstannane (1.5 eq; prepared according to *Eur. J. Org. Chem.* 2003, 1711-1721) were added. The mixture was warmed at 130° C. for 10 minutes (microwave), then poured in aqueous saturated solution of NH₄Cl and extracted with AcOEt. The organic layers were combined, dried (Na₂SO₄) and concentrated under vacuum; crude product was purified by silica gel column chromatography (DCM to DCM/MeOH 9/1). The enantiomeric purity was calculated as enantiomeric eccess (ee %) by chiral HPLC methods.

According to general procedure 8 the following compounds were prepared:

| Comp. | Name | Yield % |
|---|---|---|
| 40 | (S)-(5-(((5-chloropyridin-2-yl)amino)methyl)-6-azaspiro[2.5]octan-6-yl)(2-(pyrimidin-2-yl)phenyl)methanone | 30 |
| 41 | (S)-(5-(((6-chloropyridin-2-yl)amino)methyl)-6-azaspiro[2.5]octan-6-yl)(5-methyl-2-(pyrimidin-2-yl)phenyl)methanone | 55 |
| 42 | (S)-(5-(((6-chloropyridin-2-yl)amino)methyl)-6-azaspiro[2.5]octan-6-yl)(5-methyl-2-(pyrazin-2-yl)phenyl)methanone | 18 |
| 43 | (S)-(5-methyl-2-(pyrazin-2-yl)phenyl)(5-(((6-(trifluoromethyl)pyridin-2-yl)amino)methyl)-6-azaspiro[2.5]octan-6-yl)methanone | 5 |
| 44 | (S)-(5-(((5-chloropyridin-2-yl)amino)methyl)-6-azaspiro[2.5]octan-6-yl)(5-fluoro-2-(pyrimidin-2-yl)phenyl)methanone | 15 |
| 45 | (S)-(5-(((5-chloropyridin-2-yl)amino)methyl)-6-azaspiro[2.5]octan-6-yl)(2-fluoro-6-(pyrimidin-2-yl)phenyl)methanone | 11 |
| 46 | (S)-(5-(((5-chloropyridin-2-yl)amino)methyl)-6-azaspiro[2.5]octan-6-yl)(5-fluoro-2-(pyrazin-2-yl)phenyl)methanone | 17 |

Compounds 40-46 Characterization:

| Comp | Ar1 | Ar2 | R1 | R2 | ¹H-NMR | MS | ee % |
|---|---|---|---|---|---|---|---|
| 40 | 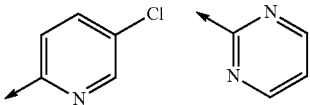 | 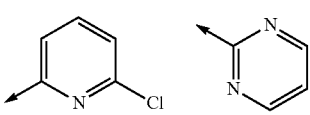 | H | H | ¹HNMR (CDCl₃) δ ppm 8.80-8.98 (m, 1H), 8.64 (d, 1H), 8.08-8.42 (m, 1H), 8.05 (m, 1H), 7.60-7.90 (m, 1H), 7.10-7.50 (m, 4H), 6.20-6.45 (m, 1H), 4.75-5.20 (m, 1H), 4.0-4.45 (m, 1H), 3.01-3.95 (m, 3H), 1.90-2.34 (m, 2H), 1.50-1.80 (m, 1H), 0.68-1.20 (m, 1H), 0.20-0.65 (m, 4H) | ESI+ m/z 434 [M + H]⁺ | 98 |
| 41 | | | Me | H | ¹HNMR (CDCl₃) δ ppm 8.79-9.0 (m, 1H), 8.71 (d, 1H), 8.13-8.36 (m, 1H), 7.70 (m, 1H), 7.47-7.59 (m, 1H), 7.25-7.40 (m, 2H), 7.10-7.20 (m, 1H), 5.86-6.64 (m, 2H), 5.22-5.96 (m, 1H), 4.64-5.17 (m, 1H), 3.91-4.40 (m, 1H), 3.45-3.73 (m, 1H), 3.01-3.40 (m, 2H), 2.34-2.46 (m, 3H), 1.91-2.29 (m, 2H), 1.22-1.66 (m, 1H), 0.19-0.74 (m, 4H) | ESI+ m/z 470 [M + Na]⁺ | 40 |

-continued

| Comp | Ar1 | Ar2 | R1 | R2 | $^1$H-NMR | MS | ee % |
|---|---|---|---|---|---|---|---|
| 42 | pyridine-Cl | pyrazine | Me | H | $^1$HNMR (CDCl$_3$) δ ppm 8.41-8.93 (m, 3H), 7.55-7.72 (m, 2H), 7.48 (m, 1H), 7.12-7.40 (m, 3H), 5.95-6.65 (m, 3H), 5.0-5.45 (m, 1H), 4.30-4.77 (m, 1H), 3.69-3.91 (m, 1H), 3.43-3.63 (m, 1H), 2.91-3.39 (m, 2H), 2.23-2.47 (m, 3H), 0.71-2.0 (m, 1H), 0.77-1.28 (m, 3H), 0.15-0.63 (m, 4H) | ESI+ m/z 470 [M + Na]$^+$ | 40 |
| 43 | pyridine-CF$_3$ | pyrazine | Me | H | $^1$HNMR (CDCl$_3$) δ ppm 8.93 (m, 1H), 8.41-8.67 (m, 2H), 7.20-7.67 (m, 4H), 6.83-7.08 (m, 1H), 6.22-6.69 (m, 1H), 5.11 (m, 1H), 4.43-4.76 (m, 1H), 3.6-3.95 (m, 1H), 3.18-3.54 (m, 2H), 2.17-2.48 (m, 3H), 1.98 (m, 1H), 0.77-1.28 (m, 1H), 0.2-0.65 (m, 4H) | ESI+ m/z 504 [M + Na]$^+$ | 98 * Method E |
| 44 | pyridine-Cl | pyrimidine | F | H | $^1$HNMR (CDCl$_3$) δ ppm 8.80-8.93 (m, 1H), 8.64 (d, 1H), 8.24-8.50 (m, 1H), 7.83-8.08 (m, 1H), 6.89-7.40 (m, 4H), 6.17-6.56 (m, 1H), 5.11-5.25 (m, 1H), 4.3-4.9 (m. 1H), 3.6-4.0 (m, 2H), 3.01-3.47 (m, 2H), 1.92-2.38 (m, 1H), 1.45-1.8 (m, 1H), 0.65-1.12 (m, 1H), 0.17-0.59 (m, 4H) | ESI+ m/z 474 [M + Na]$^+$ | 98 * Method E |
| 45 | pyridine-Cl | pyrimidine | H | F | $^1$HNMR (CDCl$_3$) δ ppm 8.82-8.92 (m, 1H), 8.69 (m, 1H), 8.17-8.28 (m, 1H), 7.81-8.02 (m, 1H), 7.51 (m, 1H), 7.01-7.35 (m, 3H), 6.28-6.57 (m, 1H), 4.79-5.32 (m, 1H), 3.90-4.18 (m, 1H), 3.35-3.77 (m, 2H), 3.06 (m, 1H), 2.27-2.56 (m, 1H), 1.84-2.19 (m, 1H), 1.18-1.29 (m, 1H), 0.73-1.10 (m, 1H), 0.17-0.70 (m, 4H) | ESI+ m/z 474 [M + Na]$^+$ | 98 |
| 46 | pyridine-Cl | pyrazine | F | H | $^1$HNMR (CDCl$_3$) δ ppm 7.55-7.78 (m, 2H), 7.13-7.37 (m, 6H), 6.95 (m, 1H), 4.71-5.07 (m, 1H), 3.6-3.95 (m, 1H), 3.20-3.55 (m, 2H), 1.99-2.18 (m, 1H), 1.67 (m, 1H), 0.85-1.30 (m, 0.16-0.65 (m, 4H) | ESI+ m/z 474 [M + Na]$^+$ | 40 |

* Compounds were further purified by chiral HPLC to obtain enantiomeric pure products

Example 89-95

Preparation of Compounds 47-53

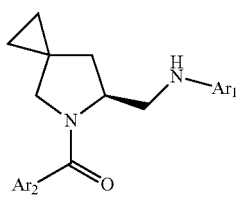

In the above formula, Ar$_1$ is Q and Ar$_2$ is R in Formula (VIa).

General Procedure 9

Ar$_2$—COOH (1 eq; prepared according to WO 2008147518 for compounds 49-51), HOBT (1 eq) and EDCl.HCl (1.5 eq) dissolved in dichloromethane (5 ml/mmol) were stirred at 25° C. for 0.5-2 hours, then intermediates 67-68 dissolved in dichloromethane were added. After 18 hours the mixture was poured in an aqueous saturated solution of NaHCO$_3$ and extracted with dichloromethane. The crude was purified by silica gel column chromatography (DCM to DCM/MeOH=9/1)

General Procedure 10

Ar$_2$—COOH (1 eq; prepared according to WO 2008147518 for compounds 49-51 and according to U.S. Pat. No. 3,282,927 for compounds 47-48), intermediates 67-68 (1 eq) and DIPEA (2 eq) were dissolved in dichloromethane (5 ml/mmol) at 0° C., then T3P (50% in DCM, 1.2 eq) was added. The mixture is stirred at reflux for 3-5 hours then at RT overnight. The reaction was washed with NaOH 1M and water, dried (Na$_2$SO$_4$) and evaporated. The crude was purified by silica gel column chromatography (DCM to DCM/MeOH=9/1).

The enantiomeric purity of all the compounds was calculated as enantiomeric eccess (ee %) by chiral HPLC methods.

According to general procedure 9, or 10 the following compounds were prepared:

| Comp. | Name | Procedure | Yield % |
|---|---|---|---|
| 49 | (S)-(6-(((5-chloropyridin-2-yl)amino)methyl)-5-azaspiro[2.4]heptan-5-yl)(5-methyl-2-(2H-1,2,3-triazol-2-yl)phenyl)methanone | 9 | 70 |
| 50 | (S)-(5-methyl-2-(2H-1,2,3-triazol-2-yl)phenyl)(6-(((6-methylpyridin-2-yl)amino)methyl)-5-azaspiro[2.4]heptan-5-yl)methanone | 9 | 90 |
| 51 | (S)-(6-(((5-chloropyridin-2-yl)amino)methyl)-5-azaspiro[2.4]heptan-5-yl)(5-methyl-2-(pyrimidin-2-yl)phenyl)methanone | 10 | 37 |

Compounds 47-53 Characterization:

| Comp. | Ar1 | Ar2 | $^1$H-NMR | MS | ee % |
|---|---|---|---|---|---|
| 49 | 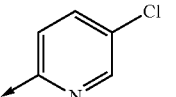 | 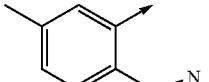 | $^1$HNMR (CDCl$_3$) δ ppm 7.99 (s, 1H), 7.69-7.85 (m, 3H), 7.30-7.39 (m, 2H), 7.18 (m, 1H), 6.86 (m, 1H), 6.69 (d, 1H), 4.68 (m, 1H), 3.71 (m, 1H), 3.59 (m, 1H), 3.11 (d, 1H), 2.40 (s, 3H), 2.19 (m, 1H), 1.59 (m, 1H), 0.37-0.69 (m, 4H) | ESI+ m/z 423 [M + H]$^+$ | 98 |
| 50 | 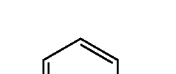 | 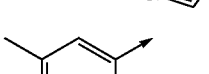 | $^1$HNMR (CDCl$_3$) δ ppm 7.85 (m, 3H), 7.30 (m, 3H), 6.48 (dd, 2H), 5.50 (m, 1H), 4.68 (m, 1H), 3.09-3.91 (m, 3H), 2.40 (s, 6H), 2.15 (m, 1H), 1.69 (m, 1H), 0.09-0.72 (m, 4H) | ESI+ m/z 403 [M + H]$^+$ | 97 |
| 51 |  |  | $^1$HNMR (CDCl$_3$) δ ppm 8.67 (m, 2H), 8.24 (d, 1H), 8.03 (d, 1H), 7.32 (m, 2H), 7.13 (m, 1H), 6.09-6.58 (d, 1H), 4.77 (m, 1H), 3.65-3.76 (m, 2H), 3.21 (d, 1H), 2.92 (m, 1H), 2.43 (s, 3H), 2.25 (m, 1H), 1.63 (m, 1H), 0.37-0.69 (m, 4H) | ESI+ m/z 456 [M + Na]$^+$ | 97 |

Example 96

Compound 54: (±)(2-methyl-5-phenylthiazol-4-yl)(7-(((6-methylpyridin-2-4amino)methyl)-8-azaspiro[4.5]decan-8-yl)methanone

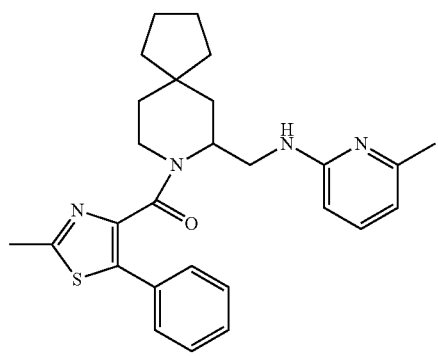

2-methyl-5-phenylthiazole-4-carboxylic acid, whose preparation has been described in U.S. Pat. No. 3,282,927(85 mg, 0.38 mmol), HOBT (52 mg, 0.38 mmol) and EDCl.HCl (110 mg, 0.578 mmol) dissolved in dichloromethane (5 ml) were stirred at 25° C. for 0.5-2 hours, then intermediate 75 (100 mg, 0.38 mmol) dissolved in dichloromethane (5 ml) was added. After 18 hours the mixture was poured in an aqueous saturated solution of NaHCO$_3$ and extracted with dichloromethane. The crude was purified by silica gel column chromatography (DCM to DCM/MeOH=9/1). Yield 36 mg of the title compound.

MS (ESI) m/z 461 [M+H]$^+$; $^1$HNMR (CDCl$_3$) δ ppm 7.20-7.51 (m, 6H) 6.02-6.46 (m, 2H) 4.63-5.07 (m, 1H) 3.60-3.97 (m, 1H) 3.25-3.51 (m, 2H) 2.83-3.07 (m, 1H) 2.61-2.74 (m, 3H) 2.34-2.39 (m, 3H) 1.76-1.11 (m, 12H) 0.71-0.92 (m, 1H).

Example 97

Compound 55: (±)(7-(((5-chloropyridin-2-yl)amino)methyl)-8-azaspiro[4.5]decan-8-yl)(2-methyl-5-phenylthiazol-4-yl)methanone

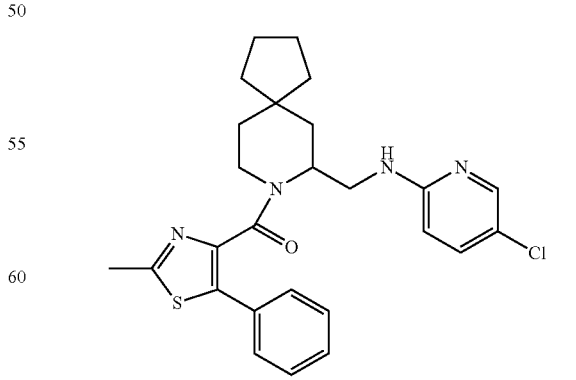

2-methyl-5-phenylthiazole-4-carboxylic acid, whose preparation has been described in U.S. Pat. No. 3,282,927(78 mg, 0.35 mmol), HOBT (48 mg, 0.35 mmol) and EDCl.HCl (102 mg, 0.53 mmol) dissolved in dichloromethane (5 ml) were stirred at 25° C. for 0.5-2 hours, then intermediate 76 (100 mg, 0.38 mmol) dissolved in dichloromethane (5 ml) was added. After 18 hours the mixture was poured in an aqueous saturated solution of $NaHCO_3$ and extracted with dichloromethane. The crude was purified by silica gel column chromatography (DCM to DCM/MeOH=9/1). Yield 52 mg of the title compound.

MS (ESI) m/z 503 [M+Na]$^+$; $^1$HNMR (CDCl$_3$) δ ppm 7.91-8.03 (m, 1H) 7.23-7.49 (m, 6H) 6.29-6.41 (m, 1H) 5.32-5.44 (m, 1H) 4.62-5.01 (m, 1H) 3.75-3.95 (m, 1H) 3.36-3.63 (m, 1H) 3.32-3.25 (m, 1H) 2.82-3.20 (m, 1H) 2.61-2.74 (m, 3H), 1.11-1.89 (m, 12H), 0.76-0.95 (m, 1H).

Example 98

Evaluation of the Effects of the Disclosure Compounds

The utility of compounds according to the present disclosure as antagonists of the orexin 1 (OX1) receptor has been determined by methodologies well known to those skilled in the art, including the "FLIPR" measurement of the intracellular calcium levels, [Ca2+]i (D. Smart, J. C. Jerman, S. J. Brough, S. L. Rushton, P. R. Murdock, F. Jewitt, N. A. Elshourbagy, C. E. Ellis, D. N. Middlemiss & F. Brown; British Journal of Pharmacology (1999) 128, 1-3).

In a typical experiment, the antagonistic activity against human OX1 and OX2 receptors is determined by using CHO and HEK-293 cells transfected with human recombinant OX1 and OX2 receptors respectively, seeded at density of 2 and 3×10$^4$ cells/well respectively in a 96 fluorometry well plate. Thus the plate was loaded with the calcium dye (Fluo-4NW/probenecid in HBSS, Hepes 20 mM, pH 7,4; Invitrogen) at 37° C. for 60 min. Afterward the temperature was equilibrated at 22° C. for 15 min and the [Ca2+]i measured directly on the plate by using a fluorescent plate reader (CeliLux Perkin Elmer).

Disclosure compounds 1-11 were dissolved in DMSO, diluted in HBSS (DMSO, 0.3% final) and added to the wells. In this assay 5 other compounds, with similar substituent structure with respect to the disclosure compounds but without the spiro ring, have been tested for comparison. After 5 min CHO cells were activated with orexin-A, 3 nM while HEK-293 cells were activated with orexin-B, 10 nM.

The compounds, dissolved in DMSO and diluted in the medium (DMSO, 0.3% final), have been analysed in the 1 nM-1 μM concentration range (every concentration in duplicate). The antagonistic activity has been expressed as pKb (co-logarithm of the apparent dissociation constant calculated by using the modified Cheng Prusoff equation).

Compounds of the following example tested according to this example gave pKbs as follows:

| Compound | pKb OX1 | pKb OX2 |
| --- | --- | --- |
| 1 | 6.8 | <5.0 |
| 2 | 8.2 | <5.0 |
| 3 | 7.4 | NA |
| 4 | 7.6 | NA |
| 5 | 7.9 | <6.0 |
| 6 | 6.8 | NA |
| 7 | 7.6 | <5.0 |
| 8 | 7.7 | <5.0 |
| 9 | 7.0 | <5.0 |
| 10 | 7.4 | NA |
| 11 | 7.5 | NA |
| 12 | 7.3 | NA |
| 13 | 7.6 | NA |
| 15 | 6.9 | <5.0 |
| 16 | 7.2 | NA |
| 17 | 7.5 | <5.0 |
| 18 | 7.3 | <5.0 |
| 19 | 6.9 | NA |
| 20 | 7.3 | NA |
| 21 | 6.9 | NA |
| 22 | 7.7 | <5.0 |
| 23 | 7.3 | NA |
| 24 | 7.0 | NA |
| 25 | 7.4 | NA |
| 26 | 7.6 | NA |
| 27 | 7.9 | NA |
| 28 | 7.6 | NA |
| 29 | 7.5 | NA |
| 30 | 7.2 | NA |
| 31 | 7.8 | NA |
| 32 | 7.2 | NA |
| 33 | 8.8 | NA |
| 34 | 7.7 | NA |
| 35 | 8.3 | 7.1 |
| 37 | 6.8 | <5.0 |
| 38 | 7.7 | NA |
| 39 | 7.9 | <5.0 |
| 40 | 7.5 | NA |
| 41 | 7.2 | NA |
| 42 | 7.6 | NA |
| 43 | 8.0 | NA |
| 44 | 7.8 | NA |
| 45 | 8.0 | NA |
| 46 | 6.8 | NA |
| 49 | 8.1 | <5.0 |
| 50 | 7.1 | <5.0 |
| 51 | 8.2 | <5.0 |
| 54 | 7.2 | <4.0 |
| 55 | 7.4 | <4.0 |
| comparison 1 | 6.9 | 7.5 |
| comparison 2 | 8.0 | 7.6 |
| comparison 3 | 9.0 | 8.5 |
| comparison 4 | 8.5 | 6.8 |
| comparison 5 | 8.5 | 8.4 |

Structure of comparison compounds:

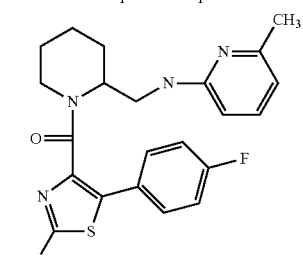

Cmp#5

| Compound | pKb OX1 | pKb OX2 |
| --- | --- | --- |
| 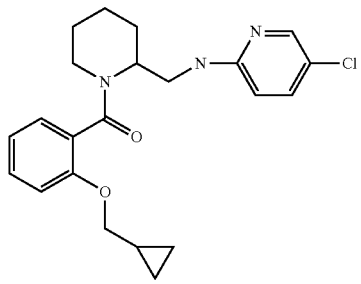 Cmp#4 | | |
| 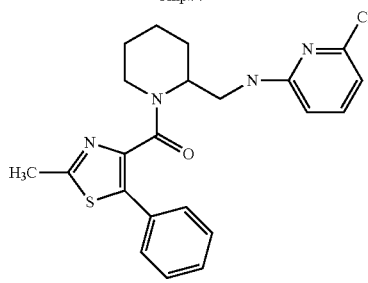 Cmp#3 | | |
| 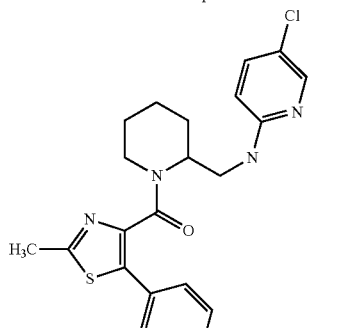 Cmp#2 | | |
| 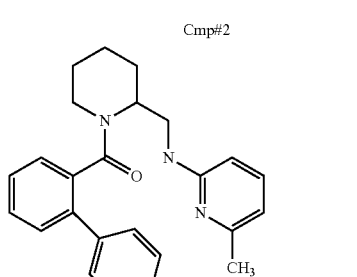 Cmp#1 | | |

NA: IC$_{50}$ vale not calculable. The concentration-response curve showed less than 25% of the effect at the highest concentration tested.
<5.0 o <6.0: IC$_{50}$ value above the highest concentration tested. The concentration-response curve showed less than 50% of the effect at the highest concentration tested.

As shown in the table, compounds of the disclosure resulted surprisingly selective against the OX1 receptor, differently from the comparison compounds which showed antagonist activity against both OX1 and OX2 receptors.

Specifically compound 2, which had a structure almost identical to comparison compound 2 apart from the spiro ring, resulted highly selective against the OX1 receptor. The same behaviour was seen between compound 1 and comparison compound 3, compound 7 and comparison compound 4 and compound 8 and comparison compound 5.

Example 99

The pharmacokinetics of compound 4 were studied in male Han Wistar rats. The rats were treated intravenously and orally (n=3 for each dose route) with a compound 2 solution at the dose of 1 mg/kg, formulated in Lactic acid 150 mM pH 4.5 in water, 5% DMSO, 10% TWEEN 80. The rats were fitted with a jugular cannula for serial sampling, a full profile was acquired for each rat. Another group of rats (n=3) was treated intravenously and sacrificed after 1 hour harvesting arterial blood and brain to assess brain penetration. Plasma and brain extracts were quantitatively analyzed using a specific and sensitive LC-MS/MS bioanalytical method. Inter-individual variations between the three rats in each group were limited (CV for pharmacokinetic parameters was below 30%).

After intravenous injection, the compound was available to the systemic circulation with average AUC values of about 740 ng·h/mL. Average values for clearance was about 320 ml/h representing 40% of rat liver blood flow that suggested moderate clearance and liver extraction. The average volume of distribution (Vss) was of 330 ml, that was twice the rat total body water, suggesting moderate compound distribution outside of the blood compartment.

After oral administration, absorption was quite fast with a clear maximum concentration reached by 30 minutes for all three animals. The average AUC was about 360 ng·h/mL representing about 50% of AUC after intravenous administration.

One hour after intravenous administration, average arterial plasmatic level was 126 ng/mL, average total brain level was 83 ng/g. Brain/plasma concentrations ratio resulted 0.66 indicating significant brain penetration of the compound.

In conclusion, compound 2 administered to rats at 1 mg/kg resulted a moderate clearance drug with moderate volume of distribution with good brain penetration characteristics. Administered as an oral solution, compound 2 presented a good absolute oral bioavailability of 50%.

What is claimed is:

1. A spiro-amino compound of Formula (VI):

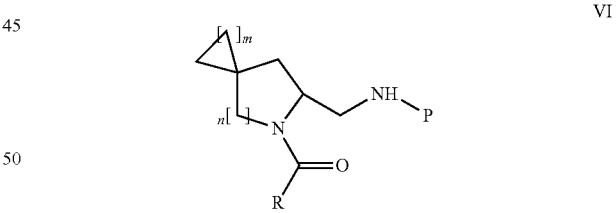

(VI)

wherein
m is 1 or 2 or 3
n is 1 or 2,
R is selected from a 5- or 6-membered aromatic ring and a 5- or 6-membered heteroaromatic ring comprising 1 to 3 heteroatoms selected from S, O and N, such ring being substituted with one or two substituents selected from the group consisting of ($C_1$-$C_3$)alkyl, halogen atom, ($C_3$-$C_5$) cycloalkyloxy, ($C_1$-$C_3$) alkyl carbonyl, phenyl optionally substituted with one or more halogen atoms, a 5- or 6-membered heterocycle comprising at least one nitrogen atom; P is a substituent Q or COQ, wherein Q is selected from the group consisting of phenyl, pyridyl, pyrimidyl, quinolyl, isoquinolyl, quinoxalyl, benzofuranyl, imidazotriazolyl, being such Q optionally substituted with one or more substituents selected from the group consisting of (C₁-C₃) alkyl, halogen, trifluoromethyl, carbammido, methylcarbammido, carboxy, methylcarboxy or a pharmaceutically acceptable salt thereof.

2. The compound according to claim 1, wherein P is Q and it is a compound of Formula (VIa):

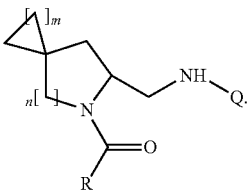

VIa

3. The compound according to claim 1, wherein P is COQ and it is a compound of Formula (VIb):

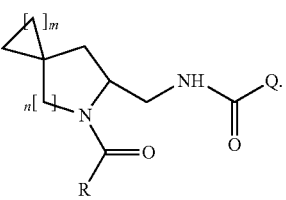

VIb

4. The compound according to claim 1, wherein n is 2 and m is 1.

5. The compound according to claim 1, wherein R is phenyl or an heterocyclic ring.

6. The compound according to claim 5, wherein when R is an heterocyclic ring this is a thiazole ring.

7. The compound according to claim 6, wherein the thiazole ring is substituted with at least one substituent selected from the group consisting of methyl, phenyl, phenyl substituted with one or more halogens.

8. The compound according to claim 5, wherein R is phenyl, optionally substituted with a substituent selected from cyclopropil (C₁-C₃) alchyloxy, triazolil, pyrimidyl.

9. The compound according to claim 1, wherein Q is a pyridyl ring, optionally substituted with one or more substituents selected from the group consisting of trifluoromethyl, carboxy, methyl and halogen.

10. The compound according to claim 2, wherein m=2 and n=2.

11. The compound according to claim 2, wherein m=3 and n=2.

12. The compound according to claim 11, wherein Q is pyridyl substituted with trifluoromethyl or pyridyl substituted with (C₁-C₃)alkyl and R is 5-membered heteroaromatic ring comprising two heteroatoms selected from S, O and N, such R being substituted with one or two substituents selected from (C₁-C₃)alkyl and halogen.

13. The compound according to claim 2, wherein m=1 and n=1.

14. The compound according to claim 13, wherein Q is pyridyl substituted with one or more halogens or pyridyl substituted with (C₁-C₃) alkyl and R is phenyl substituted with one or two substituent selected from (C₁-C₃)alkyl and a 5- or 6-membered heterocycle comprising at least one nitrogen atom.

15. A pharmaceutical composition comprising at least one compound according to claim 1 and a pharmaceutically acceptable carrier.

16. The compound according to claim 1, said compound being selected from the group consisting of:

(±)(2-methyl-5-phenylthiazol-4-yl)(5-((6-methylpyridin-2-ylamino)methyl)-6-azaspiro[2.5]octan-6-yl)methanone (R)-(2-methyl-5-phenylthiazol-4-yl)(5-(((6-methylpyridin-2-yl)amino)methyl)-6-azaspiro[2.5]octan-6-yl)methanone (S)-(2-methyl-5-phenylthiazol-4-yl)(5-(((6-methylpyridin-2-yl)amino)methyl)-6-azaspiro[2.5]octan-6-yl)methanone (±)(5-((5-chloropyridin-2-ylamino)methyl)-6-azaspiro[2.5]octan-6-yl)(2-methyl-5-phenylthiazol-4-yl)methanone (R)-(5-(((5-chloropyridin-2-yl)amino)methyl)-6-azaspiro[2.5]octan-6-yl)(2-methyl-5-phenylthiazol-4-yl)methanone (S)-(5-(((5-chloropyridin-2-yl)amino)methyl)-6-azaspiro[2.5]octan-6-yl)(2-methyl-5-phenylthiazol-4-yl)methanone (±)(2-methyl-5-phenylthiazol-4-yl)(5-((5-(trifluoromethyl)pyridin-2-ylamino)methyl)-6-azaspiro[2.5]octan-6-yl)methanone (S)-(2-methyl-5-phenylthiazol-4-yl)(5-(((5-(trifluoromethyl)pyridin-2-yl)amino)methyl)-6-azaspiro[2.5]octan-6-yl)methanone (±)(5-((5-chloropyridin-2-ylamino)methyl)-6-azaspiro[2.5]octan-6-yl)(2-(cyclopropylmethoxy)phenyl)methanone (±)(5-((5-chloropyridin-2-ylamino)methyl)-6-azaspiro[2.5]octan-6-yl)(5-(4-fluorophenyl)-2-methylthiazol-4-yl)methanone (±)(5-((5-chloropyridin-2-ylamino)methyl)-6-azaspiro[2.5]octan-6-yl)(5-methyl-2-(2H-1,2,3-triazol-2-yl)phenyl)methanone (±)(5-((5-chloropyridin-2-ylamino)methyl)-6-azaspiro[2.5]octan-6-yl)(5-methyl-2-(pyrimidin-2-yl)phenyl)methanone (S)-(5-(((5-chloropyridin-2-yl)amino)methyl)-6-azaspiro[2.5]octan-6-yl)(5-methyl-2-(pyrimidin-2-yl)phenyl)methanone (±)methyl 5-chloro-2-((6-(5-(4-fluorophenyl)-2-methylthiazole-4-carbonyl)-6-azaspiro[2.5]octan-5-yl)methylamino)benzoate (S)-(5-(((5-fluoropyridin-2-yl)amino)methyl)-6-azaspiro[2.5]octan-6-yl)(2-methyl-5-phenylthiazol-4-yl)methanone (S)-(5-(((6-chloropyridin-2-yl)amino)methyl)-6-azaspiro[2.5]octan-6-yl)(2-methyl-5-phenylthiazol-4-yl)methanone (S)-(2-methyl-5-phenylthiazol-4-yl)(5-(((6-(trifluoromethyl)pyridin-2-yl)amino)methyl)-6-azaspiro[2.5]octan-6-yl)methanone (S)-(5-(((6-chloropyridin-2-yl)amino)methyl)-6-azaspiro[2.5]octan-6-yl)(5-methyl-2-(2H-1,2,3-triazol-2-yl)phenyl)methanone (S)-(5-methyl-2-(2H-1,2,3-triazol-2-yl)phenyl)(5-(((6-(trifluoromethyl)pyridin-2-yl)amino)methyl)-6-azaspiro[2.5]octan-6-yl)methanone (S)-(2-methyl-5-phenylthiazol-4-yl)(5-(((4-methylpyrimidin-2-yl)amino)methyl)-6-azaspiro[2.5]octan-6-yl)methanone (S)-(5-(((4,6-dimethylpyrimidin-2-yl)amino)methyl)-6-azaspiro[2.5]octan-6-yl)(2-methyl-5-phenylthiazol-4-yl)methanone (S)-(2-methyl-5-phenylthiazol-4-yl)(5-(((5-methylpyrimidin-2-yl)amino)methyl)-6-azaspiro[2.5]octan-6-yl)methanone (S)-(5-(((4,6-difluoropyrimidin-2-yl)amino)methyl)-6-azaspiro[2.5]octan-6-yl)(2-methyl-5-phenylthiazol-4-yl)methanone (S)-(5-(((6-fluoropyridin-2-yl)amino)methyl)-6-azaspiro[2.5]octan-6-yl)(2-methyl-5-phenylthiazol-4-yl)methanone (S)-(5-methyl-2-(2H-1,2,3-triazol-2-yl)phenyl)(5-(((5-(trifluoromethyl)pyridin-2-yl)amino)methyl)-6-azaspiro[2.5]octan-6-yl)methanone (S)-(5-methyl-2-(pyrimidin-2-yl)phenyl)(5-(((5-(trifluoromethyl)pyridin-2-yl)amino)methyl)-6-azaspiro[2.5]octan-6-yl)methanone (S)-(2-(2H-1,2,3-triazol-2-yl)phenyl)(5-(((5-chloropyridin-2-yl)amino)methyl)-6-azaspiro[2.5]octan-6-yl)methanone (S)-(5-(((5-chloropyridin-2-yl)amino)methyl)-6-azaspiro[2.5]octan-6-yl)(5-fluoro-2-(2H-1,2,3-triazol-2-yl)phenyl)methanone (S)-(5-(((5-chloropyridin-2-yl)amino)methyl)-6-azaspiro[2.5]octan-6-yl)(2-(pyrazin-2-yl)phenyl)methanone (S)-(5-(((5-chloropyridin-2-yl)amino)methyl)-6-azaspiro[2.5]octan-6-yl)(2-fluoro-6-(2H-1,2,3-triazol-2-yl)phenyl)methanone (S)-(5-(((5-chloropyridin-2-yl)amino)methyl)-6-azaspiro[2.5]octan-6-yl)(5-fluoro-2-(pyridin-2-yl)phenyl)methanone (S)-(5-(((5-chloropyridin-2-yl)amino)methyl)-6-azaspiro[2.5]octan-6-yl)(5-methyl-2-(pyridin-2-yl)phenyl)methanone (S)-(5-(((5-chloropyridin-2-yl)amino)methyl)-6-azaspiro[2.5]octan-6-yl)(2-fluoro-6-(pyridin-2-yl)phenyl)methanone (S)-[1,1'-biphenyl]-2-yl(5-(((4,6-dimethylpyrimidin-2-yl)amino)methyl)-6-azaspiro[2.5]octan-6-yl)methanone (S)-(2,5-dichlorophenyl)(5-(((4,6-dimethylpyrimidin-2-yl)amino)methyl)-6-azaspiro[2.5]octan-6-yl)methanone (S)-[1,1'-biphenyl]-2-yl(5-(((5-chloropyridin-2-yl)amino)methyl)-6-azaspiro[2.5]octan-6-yl)methanone (S)-[1,1'-biphenyl]-2-yl(5-(((4-methylpyrimidin-2-yl)amino)methyl)-6-azaspiro[2.5]octan-6-yl)methanone (S)-(5-(((5-chloropyridin-2-yl)amino)methyl)-6-azaspiro[2.5]octan-6-yl)(2-(pyrimidin-2-yl)phenyl)methanone (S)-(5-(((6-chloropyridin-2-yl)amino)methyl)-6-azaspiro[2.5]octan-6-yl)(5-methyl-2-(pyrimidin-2-yl)phenyl)methanone (S)-(5-(((6-chloropyridin-2-yl)amino)methyl)-6-azaspiro[2.5]octan-6-yl)(5-methyl-2-(pyrazin-2-yl)phenyl)methanone (S)-(5-methyl-2-(pyrazin-2-yl)phenyl)(5-(((6-(trifluoromethyl)pyridin-2-yl)amino)methyl)-6-azaspiro[2.5]octan-6-yl)methanone (S)-(5-(((5-chloropyridin-2-yl)amino)methyl)-6-azaspiro[2.5]octan-6-yl)(5-fluoro-2-(pyrimidin-2-yl)phenyl)methanone (S)-(5-(((5-chloropyridin-2-yl)amino)methyl)-6-azaspiro[2.5]octan-6-yl)(2-fluoro-6-(pyrimidin-2-yl)phenyl)methanone (S)-(5-(((5-chloropyridin-2-yl)amino)methyl)-6-azaspiro[2.5]octan-6-yl)(5-fluoro-2-(pyrazin-2-yl)phenyl)methanone (S)-(6-(((5-chloropyridin-2-yl)amino)methyl)-5-azaspiro[2.4]heptan-5-yl)(5-methyl-2-(2H-1,2,3-triazol-2-yl)phenyl)methanone (S)-(5-methyl-2-(2H-1,2,3-triazol-2-yl)phenyl)(6-(((6-methylpyridin-2-yl)amino)methyl)-5-azaspiro[2.4]heptan-5-yl)methanone (S)-(6-(((5-chloropyridin-2-yl)amino)methyl)-5-azaspiro[2.4]heptan-5-yl)(5-methyl-2-(pyrimidin-2-yl)phenyl)methanone (±)(2-methyl-5-phenylthiazol-4-yl)(7-(((6-methylpyridin-2-yl)amino)methyl)-8-azaspiro[4.5]decan-8-yl)methanone, and (±)(7-(((5-chloropyridin-2-yl)amino)methyl)-8-azaspiro[4.5]decan-8-yl)(2-methyl-5-phenylthiazol-4-yl)methanone.

17. Compound according to claim 16, wherein said compound is (S)-(5-(((5-chloropyridin-2-yl)amino)methyl)-6-azaspiro[2.5]octan-6-yl)(5-methyl-2-(pyrimidin-2-yl)phenyl)methanone, or (S)-(5-(((5-chloropyridin-2-yl)amino)methyl)-6-azaspiro[2.5]octan-6-yl)(5-fluoro-2-(pyrimidin-2-yl)phenyl)methanone.

\* \* \* \* \*